United States Patent [19]

Grudzinskas et al.

[11] 4,235,924

[45] Nov. 25, 1980

[54] PROSTACYCLIN ANALOGS OF THE 1 SERIES AND RELATED ANALOGS WHEREIN THE CARBOXYLIC ACID FUNCTION HAS BEEN REPLACED

[75] Inventors: Charles V. Grudzinskas, Nyack; Allan Wissner, Ardsley, both of N.Y.; Sow-Mei L. Chen, Park Ridge, N.J.

[73] Assignee: American Cyanamid Company, Stamford, Conn.

[21] Appl. No.: 46,511

[22] Filed: Jun. 7, 1979

[51] Int. Cl.³ ............... A61K 31/557; C07D 307/935
[52] U.S. Cl. ............................... 424/278; 424/285; 260/340.9 P; 260/346.22; 542/426; 542/429
[58] Field of Search ............... 260/346.22, 340.9 P; 542/426, 429; 278/285

[56] References Cited

U.S. PATENT DOCUMENTS 4,125,712  11/1978  Axen ..................... 260/346.22

FOREIGN PATENT DOCUMENTS 2757919  7/1978  Fed. Rep. of Germany .

Primary Examiner—Henry R. Jiles
Assistant Examiner—Bernard Dentz
Attorney, Agent, or Firm—Richard J. Hammond

[57] ABSTRACT

This disclosure describes certain 6,9α-epoxy prostacyclines and their intermediates. These compounds are useful as bronchodilators and inflammatory mediator release inhibitors.

54 Claims, No Drawings

PROSTACYCLIN ANALOGS OF THE 1 SERIES AND RELATED ANALOGS WHEREIN THE CARBOXYLIC ACID FUNCTION HAS BEEN REPLACED

BACKGROUND OF THE INVENTION (1) Field of the Invention

This invention relates to novel 6,9α-epoxy prostenoic acids and esters and to 6,9α-epoxy-1-hydroxymethyl prostenes, the alkyl ethers and the 1-ketones thereof, as well as to the cyclopentenone intermediates and processes for their preparation. The novel compounds of this invention embrace all the possible optical isomers, diastereomers and enantiomers, racemates, and racemic mixtures.

(2) Description of the Prior Art

Prostaglandins have classically been described as chemically related 20 carbon chain hydroxy fatty acids having the basic skeleton of prostanoic acid:

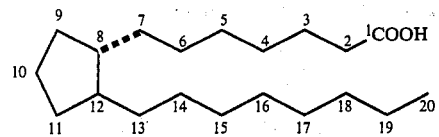

The prostaglandins having a hydroxyl group at the C-11 position and a keto group at the C-9 position are known as the PGE series, and those having a hydroxyl group in place of the keto groups are known as the PGF series and are further designated by an α or β suffix to indicate the configuration of the hydroxyl group at said position. The natural compounds are the α-Hydroxyl substituted compounds. They may contain different degrees of unsaturation in the molecule, particularly at C-5, C-13 and C-17, the unsaturation is also indicated by a suffix. Thus, for example, the PGF$_1$ and PGE$_1$ series refer to prostanoic acids having a trans olefin bond at the C-13 position, while the PGF$_2$ and PGE$_2$ series refer to prostadienoic acids having a cis-olefin bond at the C-5 position and a trans olefin bond at the C-13 position. For a review on prostaglandins and the definition of primary prostaglandins, see, for example, P. Ramwell, The Prostaglandins, pp. 5–22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al., Synthesis Vol. 1, John Wiley and Sons Inc., New York, N.Y. 1973 and P. H. Bentley, Chem. Soc. Reviews 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared [see for example, U.S. Pat. No. 3,950,406; Prostaglandins, Vol. 10, 733 (1975); Tetrahedron Letters, No. 48, 4217 (1975)].

Recently reports have also appeared wherein the C-16 carbon bearing a hydroxyl group is substituted with a methyl group [see Pappo et al., Tetrahedron Letters, No. 4, 235 (1975); Collin et al., U.S. Patent No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670).

SUMMARY

This invention relates to compounds of the formula:

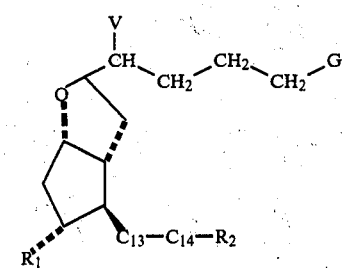

wherein V is selected from the group hydrogen, bromo, chloro and iodo, G is selected from the group —COOH, —C(O)OR, —CH$_2$OH,

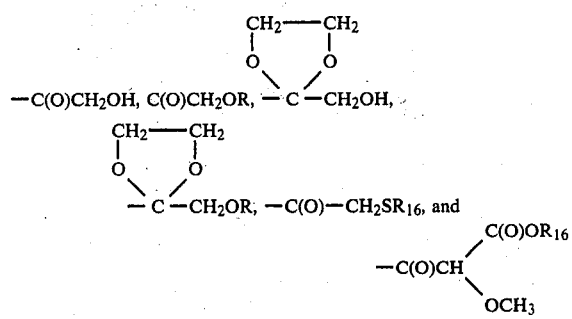

wherein R is C$_1$ to C$_6$ alkyl or optionally substituted phenyl, the substituents selected from the group C$_1$ to C$_4$ alkoxy, halo and trifluoromethyl; R$_1$ is hydrogen or hydroxy; R$_{16}$ is C$_1$ to C$_6$ alkyl; C$_{13}$-C$_{14}$ is selected from the group —CH=CH-(trans) and —CH$_2$CH$_2$—; and R$_2$ is selected from the group consisting of

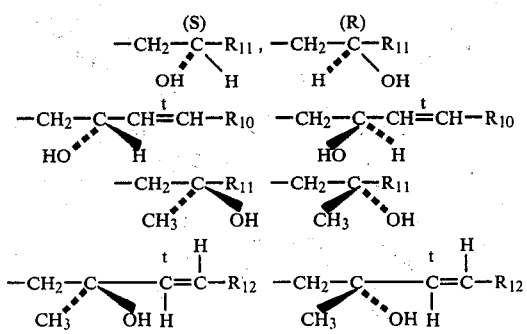

-continued

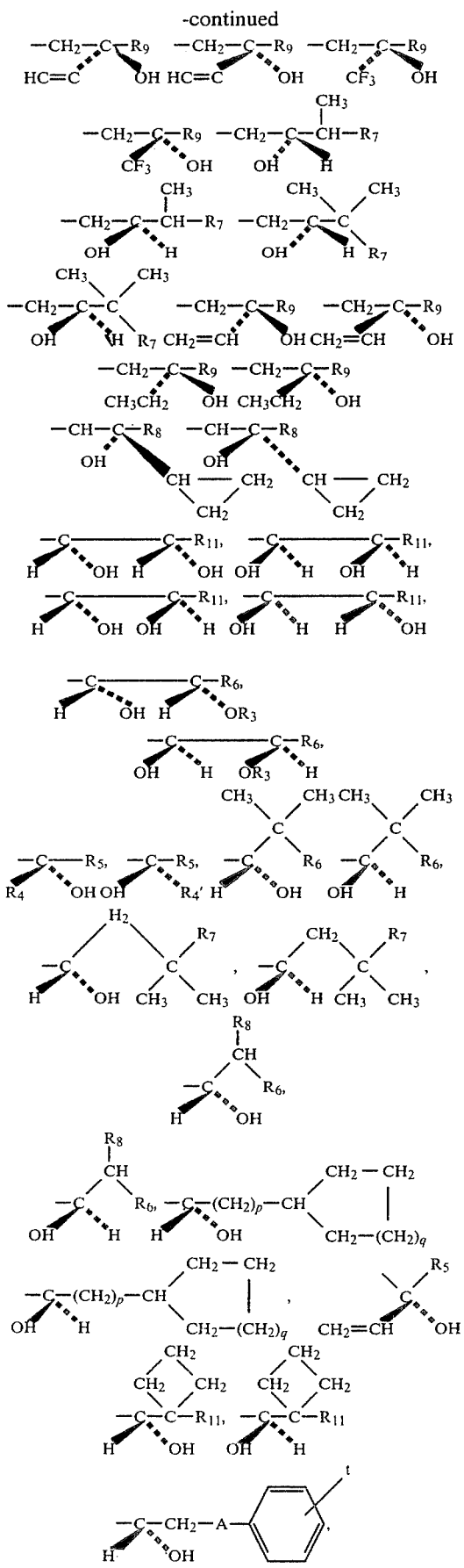

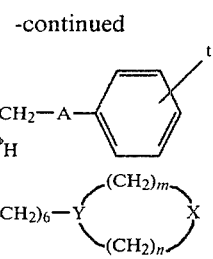

and $-(CH_2)_6-Y\begin{pmatrix}(CH_2)_m\\(CH_2)_n\end{pmatrix}X$ wherein $R_4$ is hydrogen or methyl; $R_5$ is selected from the group consisting of $C_4$-$C_7$ alkyl; $R_6$ is selected from the group consisting of $C_3$-$C_6$ alkyl; $R_7$ is selected from the group consisting of $C_2$-$C_4$ alkyl; $R_8$ is selected from the group consisting of $C_1$-$C_2$ alkyl; $R_9$ is selected from the group consisting of $C_3$-$C_6$ alkyl; $R_{10}$ is selected from the group consisting of $C_1$-$C_4$ alkyl; $R_{11}$ is selected from the group consisting of $C_3$-$C_7$ alkyl; $R_{12}$ is selected from the group consisting of $C_1$-$C_4$ alkyl; p is an integer from 0 to 3; q is 1 or 2; X is a divalent radical selected from the group consisting of:

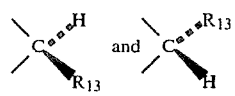

wherein $R_{13}$ is selected from the group consisting of $C_1$-$C_7$ alkyl, hydrogen, and a phenoxy group optionally substituted with a substituent selected from the group consisting of halogen, trifluoromethyl and $C_1$-$C_4$ alkyloxy; Y is a divalent radical selected from the group consisting of:

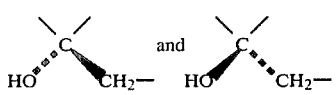

A is a divalent radical selected from $-CH_2$ and $-O-$; m is an integer from 0 to 4 inclusive; n is an integer from 0 to 4, inclusive, with the proviso that the sum of m and n has the value of 1 to 4; s is zero or the integer 1; and t is selected from the group consisting of hydrogen, chloro, fluoro, dichloro, trifluoromethyl and methoxy; to the racemic mixtures thereof; and to the mirror images thereof, as well as to pharmaceutically acceptable, non-toxic salts thereof.

The invention also relates to the method of preparing the above-described compounds, as well as to novel intermediates useful for the preparation of the prostaglandin compounds described herein. The present invention will be fully described with reference to the flowsheets and examples of this application.

DESCRIPTION OF THE PREFERRED EMBODIMENT

Compounds of the formula:

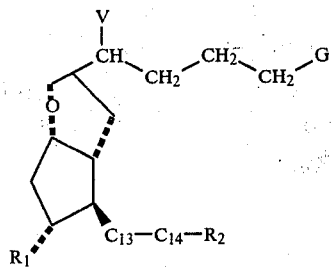

wherein V is selected from the group hydrogen, bromo, chloro and iodo; G is selected from the group —COOH, —C(O)OR, —CH₂OH,

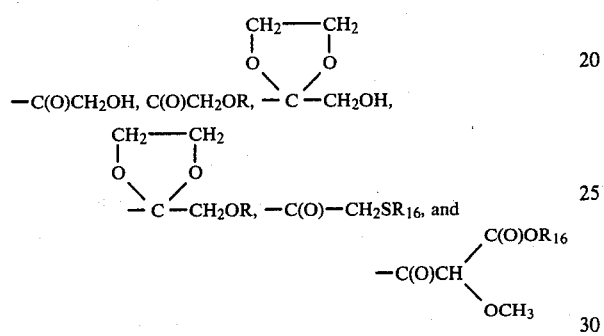

wherein R is $C_1$ to $C_6$ alkyl or optionally substituted phenyl, the substituents selected from the group $C_1$ to $C_4$ alkyl, $C_1$ to $C_4$ alkoxy, halo and trifluoromethyl; $R_1$ is hydrogen or hydroxy; $R_{16}$ is $C_1$ to $C_6$ alkyl; $C_{13}$–$C_{14}$ is selected from the group —CH=CH—(trans) and —CH₂CH₂—; and $R_2$ is selected from the group consisting of:

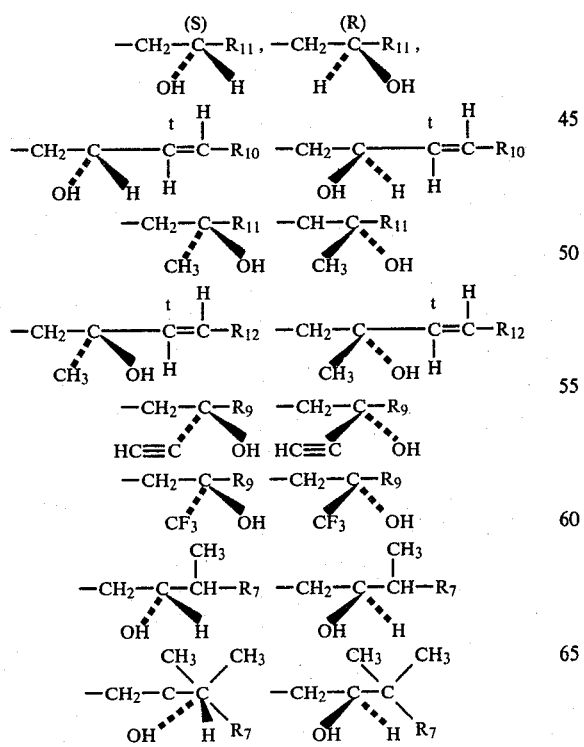

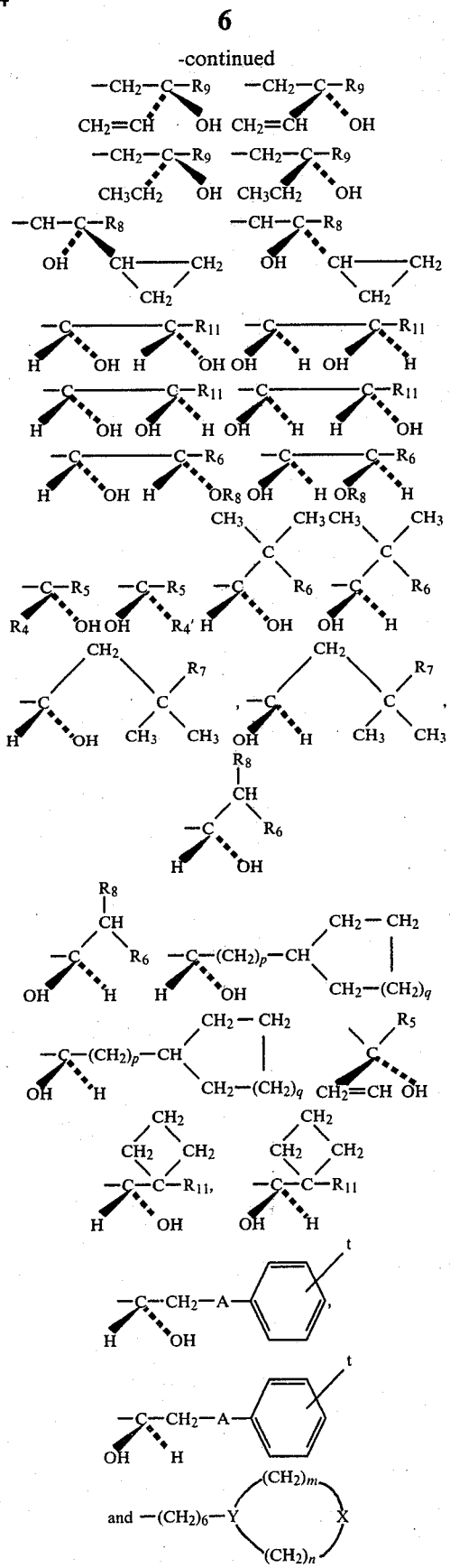

wherein $R_4$ is hydrogen or methyl; $R_5$ is selected from the group consisting of $C_4$–$C_7$ alkyl; $R_6$ is selected from the group consisting of $C_3$–$C_6$ alkyl; $R_7$ is selected from the group consisting of $C_2$-$C_4$ alkyl; $R_8$ is selected from the group consisting of $C_1$-$C_2$ alkyl; $R_9$ is selected from the group consisting of $C_3$-$C_6$ alkyl; $R_{10}$ is selected from the group consisting of $C_1$-$C_4$ alkyl; $R_{11}$ is selected from the group consisting of $C_3$-$C_7$ alkyl; $R_{12}$ is selected from the group consisting of $C_1$-$C_4$ alkyl; p is an integer from 0 to 3; q is 1 or 2; X is a divalent radical selected from the group consisting of:

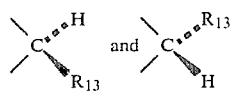

wherein $R_{13}$ is selected from the group consisting of $C_1$-$C_7$ alkyl, hydrogen, and a phenoxy group optionally substituted with a substituent selected from the group consisting of halogen, trifluoromethyl and $C_1$-$C_4$ alkyloxy; Y is a divalent radical selected from the group consisting of:

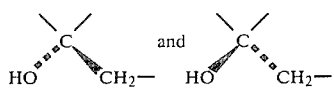

A is a divalent radical selected from —$CH_2$ and —O—; m is an integer from 0 to 4 inclusive; n is an integer from 0 to 4, inclusive, with the proviso that the sum of m and n has the value of 1 to 4; s is the integer 0 or 1; and t is selected from the group consisting of hydrogen, chloro, fluoro, dichloro, trifluoromethyl, and methoxy; the racemic mixtures thereof; and the mirror images thereof, and the pharmaceutically acceptable, non-toxic salts thereof.

The prostacyclin compounds of the present invention may subgenerically be represented by the compounds of the following formulas:

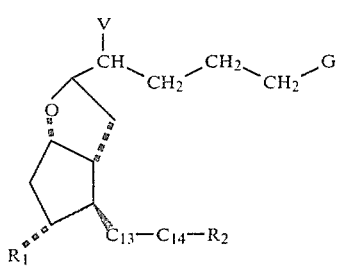

I(a)

wherein $R_2$ is selected from the group

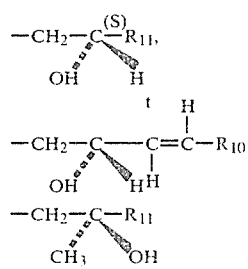

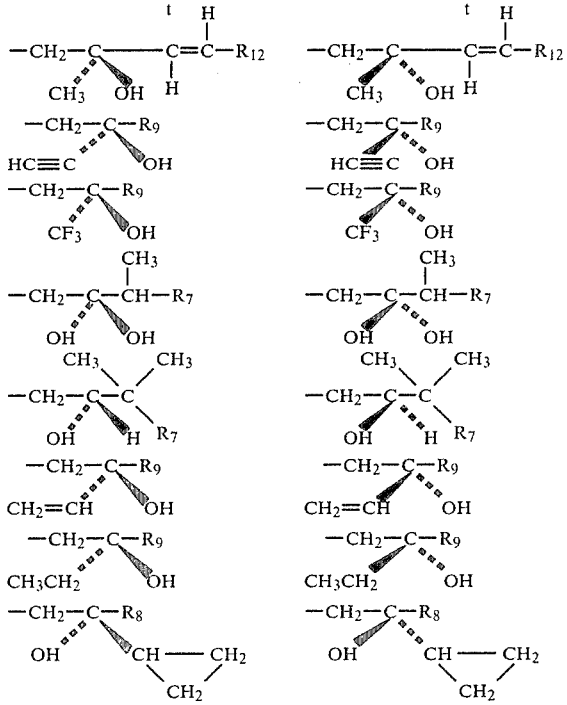

wherein $R_7$, $R_9$, $R_{10}$, $R_{11}$, $R_{12}$, G, V and $C_{13}$-$C_{14}$ are as previously defined.

In the above compounds of formula I(a) it is preferred that: G be selected from the group

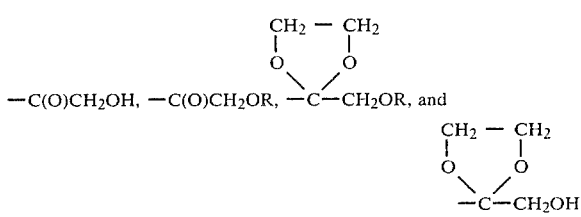

where R is as previously defined, most preferably

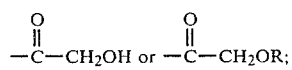

V be selected from the group hydrogen and iodo, most preferably iodo; $C_{13}$-$C_{14}$ be —CH=CH—(trans); and $R_2$ be selected from the group

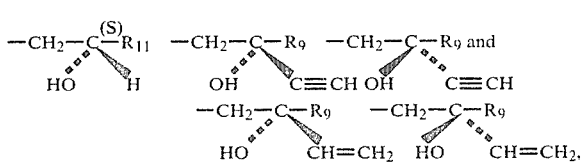

most preferably

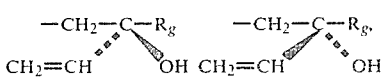

where $R_9$ and $R_{11}$ are as previously defined.

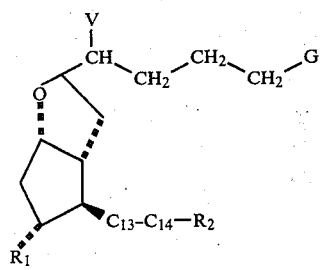  I(b)

wherein $R_2$ is selected from the group

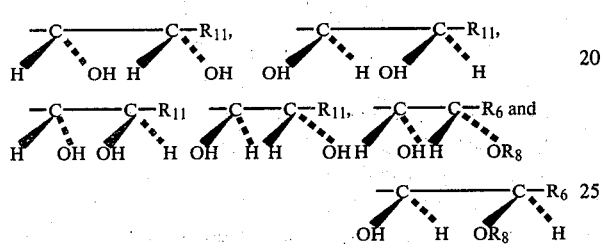

wherein $R_6$, $R_8$, $R_{11}$, G, V and $C_{13}$-$C_{14}$ are as previously defined.

In the compounds of formula I(b), it is preferred that, G be selected from the group —C(O)CH$_2$OH, —C(O)CH$_2$OR,
$$-\underset{\underset{\underset{CH_2OR}{|}}{O\diagdown\diagup O}}{\overset{\overset{CH_2-CH_2}{|}}{C}}-CH_2OR,$$

$$-\underset{\underset{\underset{CH_2OH}{|}}{O\diagdown\diagup O}}{\overset{\overset{CH_2-CH_2}{|}}{C}} \text{ or } -\overset{O}{\underset{}{\overset{\|}{C}}}-OR$$

most preferably —C(O)CH$_2$OH or C(O)CH$_2$OR; V be selected from the group hydrogen and iodo, most preferably iodo; $C_{13}$-$C_{14}$ be —CH=CH—(trans) and $R_2$ selected from the group

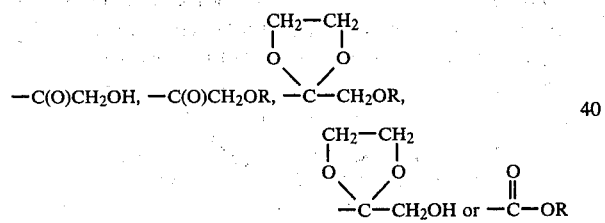

most preferably

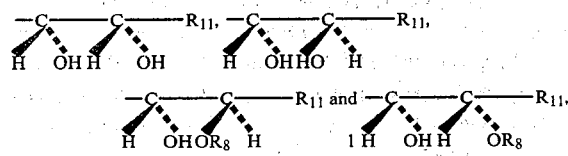

where R, $R_8$, $R_{11}$ are as previously defined.

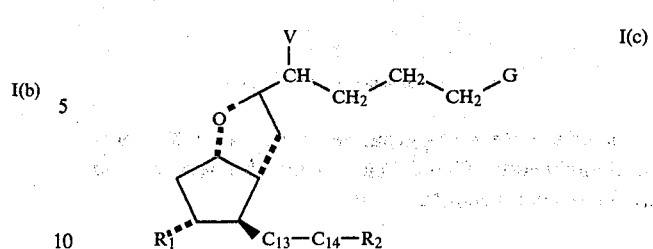  I(c)

wherein $R_2$ is selected from the group

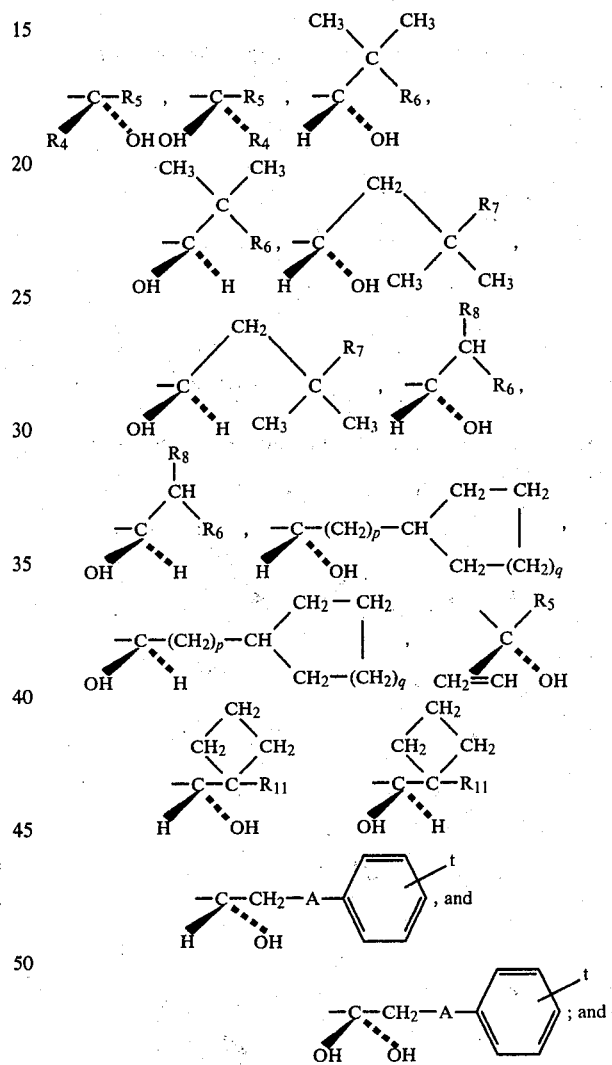

wherein $R_1$, $R_4$, $R_5$, $R_6$, $R_7$, $R_8$, $R_{11}$, p, q, t, A, G, V and $C_{13}$-$C_{14}$ are as previously defined.

In the compounds of formula I(c), it is preferred that, G be selected from the group

—C(O)CH$_2$OH, —C(O)CH$_2$OR, $$-\underset{\underset{\underset{CH_2OR}{|}}{O\diagdown\diagup O}}{\overset{\overset{CH_2-CH_2}{|}}{C}}-CH_2OR, \text{ and } -\underset{\underset{\underset{CH_2OH}{|}}{O\diagdown\diagup O}}{\overset{\overset{CH_2-CH_2}{|}}{C}}-CH_2OH$$

most preferably

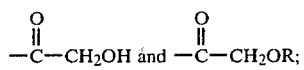

V be selected from the group hydrogen and iodo, most preferably iodo; $C_{13}$-$C_{14}$ be —CH=CH—(trans) and $R_2$ be selected from the group

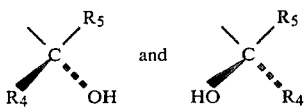

Other preferred $R_2$ moieties are those selected from the group

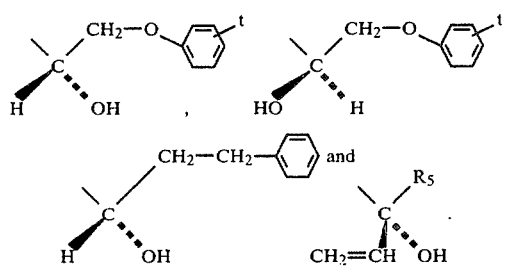

Additional preferred $R_2$ moieties are those selected from the group

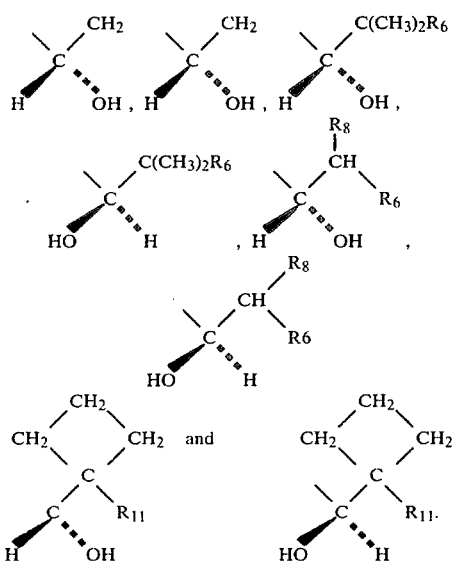

Most preferably $R_2$ is the moiety selected from the group

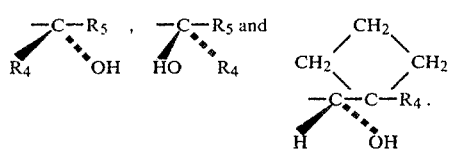

In these preferred and most preferred embodiments $R_1$, $R_4$, $R_5$, $R_6$, $R_8$, $R_{11}$, p, q, A and t are as previously defined.

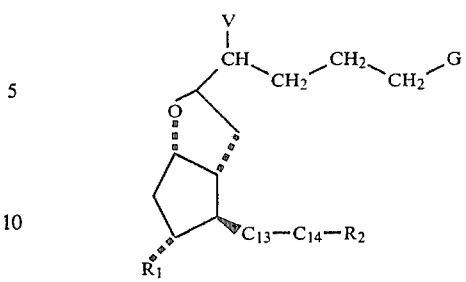

wherein $R_2$ is selected from the group

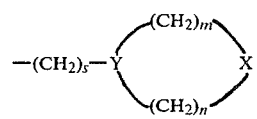

wherein V, G, $R_1$, and $C_{13}$-$C_{14}$ are as previously defined X is a divalent radical selected from the group consisting of:

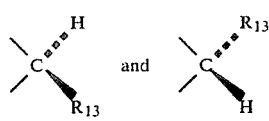

wherein $R_{13}$ is selected from the group consisting of $C_1$-$C_7$ alkyl, hydrogen, and a phenoxy group optionally substituted with a substituent selected from the group consisting of halogen, trifluoromethyl and $C_1$-$C_4$ alkyloxy; Y is a divalent radical selected from the group consisting of:

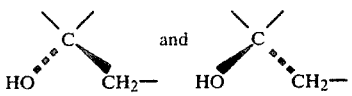

m is an integer from 0 to 4 inclusive; n is an integer from 0 to 4, inclusive; with the proviso that the sum of m and n has the value of 1 to 4; and s is the integer 0 or 1.

The compounds of this invention can be prepared by a 1,4-conjugate-addition procedure involving treatment of the ether blocked cyclopentenone such as (111) with a lithio-cuprate reagent such as (117), (118), or (119) prepared as illustrated in Flowsheets A through N.

These processes and many of the intermediates useful for the preparation of the compounds of formula I are set forth in some detail in U.S. application Ser. No. 3,953, filed January 16, 1979, filed on even date herewith, incorporated herein by references.

The 1,4-conjugate-addition procedure is described hereinbelow in Flowsheet N. The preparation of the various requisite 1-iodo-trans-1-alkenyl or 1-tributylstannyl-trans-1-alkenyl derivatives is illustrated in Flowsheets A-H and the methods of preparation of the 4-hydroxycyclopentenones embracing the 1-(hydroxymethyl)1-oxo chain is described in connection with Flowsheets I-M.

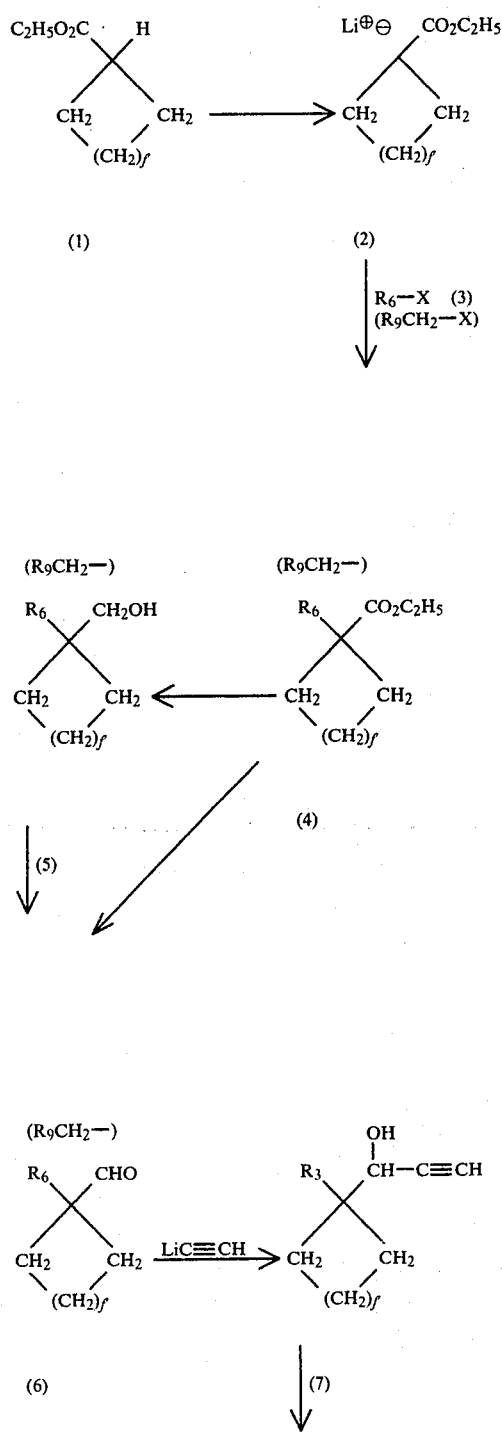

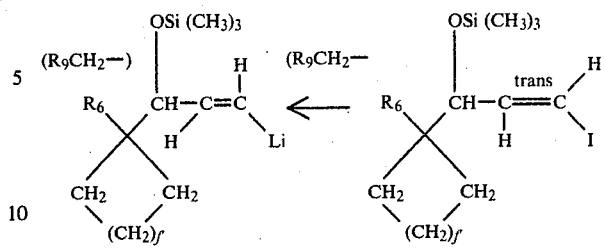

(9)  (8)

wherein f' is one or two inclusive.

In accordance with the scheme as outlined hereinabove in Flowsheet A, carbethoxycyclobutane or carbethoxycyclopentane is converted to its enolate anion (2) by treatment with a strong base such as lithium cyclohexylisopropylamide, prepared from the corresponding amine and n-butyl lithium (hexane solution) in a solvent, such as anhydrous tetrahydrofuran, at very low temperatures, such as $-78°$ C. The resulting enolate anion (2) is then alkylated with $R_6$-X (3) to provide (4), the ester group of which is reduced to alcohol (5) by reaction with 2 equivalents of diisobutyl aluminum hydride, lithium aluminum hydride or the like. Oxidation of alcohol (5) with dipyridine chromium oxide complex ["Reagents for Organic Synthesis", L. F. Fieser and M. Fieser, John Wiley and Sons, Inc., New York, 4, 215 (1974)], prepared in situ in methylene chloride solution, provides the corresponding aldehyde (6), which can also be obtained directly from ester (4) by partial reduction with one equivalent of diisobutyl aluminum hydride at $-78°$ C., but the former two-step procedure is preferrable. Reaction of aldehyde (6) with lithium acetylide ethylenediamine complex provides the 3-hydroxy-1-alkyne (7), which is converted to its trimethysilyl ether in the usual manner. The silylated derivative is then treated with disiamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-4,4-methylene-1-alkene (8). Also, the above sequence of reactions can be accomplished, as shown in Flowsheet A, using $R_9CH_2X$ where $R_9$ is a phenyl group.

FLOWSHEET B
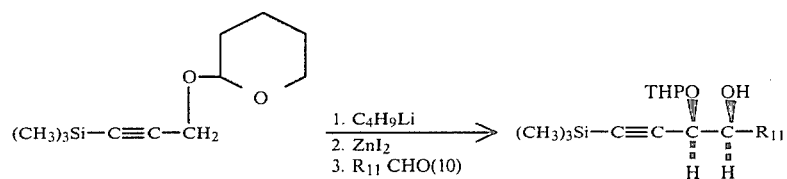
(9) → (11)
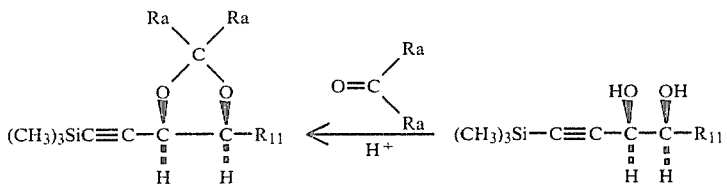
(13) ← (12)
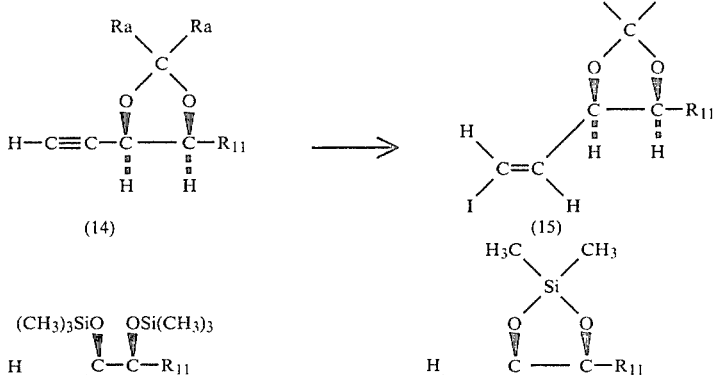
(14) → (15)
(16) (17)
(11) →
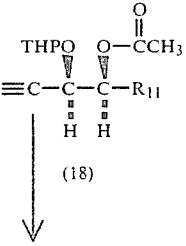
(18)
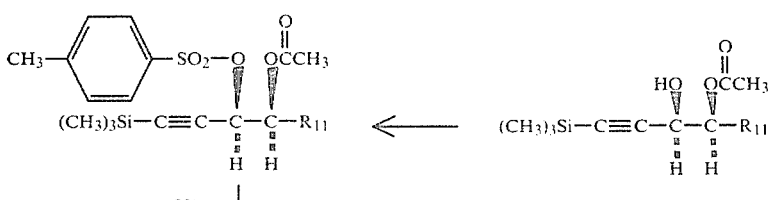
(20) ← (19)

FLOWSHEET B
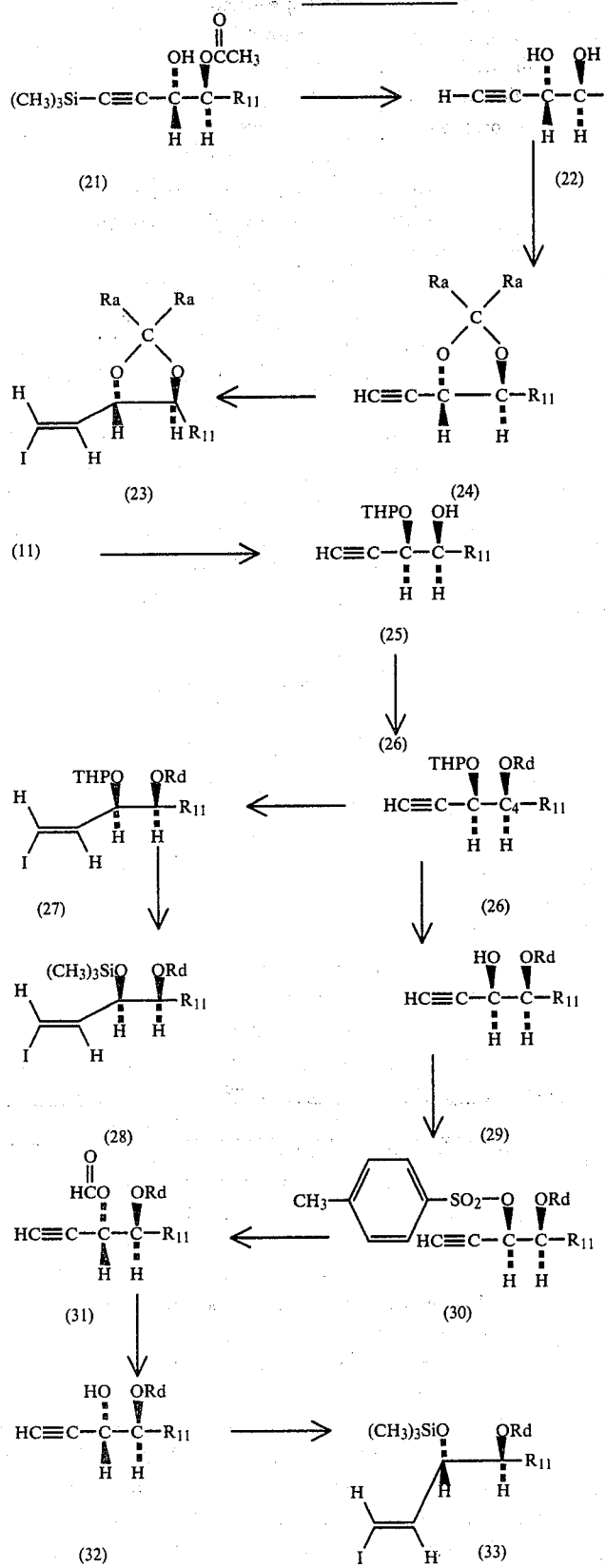
In accordance with the scheme as outlined hereinabove in Flowsheet B, 1-trimethylsilyl-3-tetrahydropyranyloxy-1-propyne (9) is treated with n-butyllithium at −78° C. and then with a freshly prepared solution of zinc iodide in anhydrous tetrahydrofuran, also at −78° C. Reaction of aldehyde (10) with the resulting reagent then provides the 4-hydroxy-3-tetrahydropyranyloxy-1-alkyne (11). This reaction is stereo specific, the product (11) being in the erythro configuration. (For additional information concerning this reaction see the examples which follow and F. Mercier, R. Epstein and S. Holland, Bull. Soc. Chim. France, 690(1972)).

The tetrahydropyranyl group in (11) is removed on weak acid treatment. The resulting erythro diol (12) can be reblocked by treating with an appropriate aldehyde or ketone

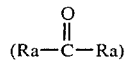

in the presence of strong acid catalyst in the usual way to give the ketal or acetal (13). Acetone is a useful ketone for this purpose and the product (13) is then a 3,4-isopropylidenedioxy-1-alkyne. It is also possible to utilize silyl blocking groups (introduced after removal of the 1-trimethylsilyl group) to ultimately give the vinyl iodides (16) or (17). Weak base treatment of (13), for example, heating for about one hour in refluxing methanol with potassium carbonate, results in desilylation to give (14). The 1-alkene (14) is converted to the corresponding 1-iodo-trans-1-alkene (15) by treatment with disamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give (15).

For the preparation of the threo derivatives, the 4-hydroxy-3-tetrahydropyranyloxy-1-alkyne (11) is acetylated to provide the corresponding 4-acetoxy derivative (18). The tetrahydropyranyl group is preferentially hydrolized with weak acid to (19), which is then tosylated in the usual manner to afford the erythro-3-tosyloxy-4-acetoxy-1-alkyne (20). Solvolysis of (20) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (21), which is then deblocked with aqueous base to give the threo-3,4-diol (22). Diol (22) is converted to an acetal or ketal (23) [or a silyl derivative as in (16) or (17)] and thence to the 1-iodo-trans-1-alkene (16) as described hereinabove wherein Ra is $C_1$ to $C_3$ alkyl.

For the preparation of the 16-alkoxyprostanoic acids of this invention, an erythro-4-hydroxy-3-tetrahydropyranyl-oxy-1-alkyne (11) is desilyated by a methanol-potassium carbonate treatment and the resulting (25) is alkylated to give the 4-alkoxy-3-tetrahydropyranyloxy-1-alkyne (26). A useful procedure for this step involves treatment of (25) with a molar equivalent of sodium hydride to give the 4-alkoxide which is then alkylated with the appropriate alkyl halide alkylating agent, for example methyl iodide. The 4-alkoxy-1-alkyne (26) is then converted to the corresponding 1-iodo-trans-1-alkene (27) as described hereinabove for the preparation of (15). If desired the tetrahydropyranyl blocking group in (27) can be hydrolyzed with weak acid and the resulting free 3-ol corresponding to (27) converted to the 3-trimethylsilyloxy derivative (28), in the usual manner, wherein $R_d$ is $C_1$ to $C_3$ alkyl.

For the threo series, the tetrahydropyranyl group in the erythro-4-alkoxy-1-alkyne (26) is cleaved and the resulting 3-hydroxy-4-alkoxy-1-alkyne (29) is tosylated to give the erythro-3-tosyloxy-4-alkoxy-1-alkyne (30). An Sn2 displacement reaction of (30) with reagents such as tetrahydroammonium formate results in inversion to the threo derivative (31), saponification of which provides threo-3-hydroxy-4-alkoxy-1-alkyne (32). Trimethylsilylation followed by the vinyl iodide conversion procedure described hereinabove furnishes the threo-1-iodo-1-alkene (33) wherein Rd is hydrogen or $C_1$ to $C_3$ alkyl.

The 15-alkyl and/or 16-alkyl derivatives of this invention can be prepared by substituting

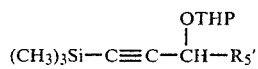

for (9) and/or

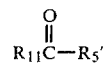

for (10) ($R_5$=alkyl of 1 to 3 carbons) in Flowsheet B.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride ethereate) and then anhydrous trimethylamine oxide. The resulting solution and an iodine solution in tetrahydrofuran are added simultaneously to a sodium hydroxide solution to give the 1-iodo-4-trimethylsilyloxy-trans-1-alkene (36), precursors for 16-hydroxyprostacyclins.

The trimethylsilyl protecting group is removed with mild acid and the resulting vinyl iodide alcohol is oxidized with pyridinium chlorochromate to provide the 1-iodo-4-oxotrans-1-alkene (37), which upon treatment with a Grignard reagent ($R_{13}MgX$) provides the 1-iodo-4-hydroxy-trans-1-alkene, which is silylated in the usual manner to provide the silyl ether (38) wherein $R_{11}'$ is a $C_3$ to $C_7$ alkyl or alkenyl group and $R_{13}'$ is vinyl, cyclopropyl or ethyl.

FLOWSHEET C

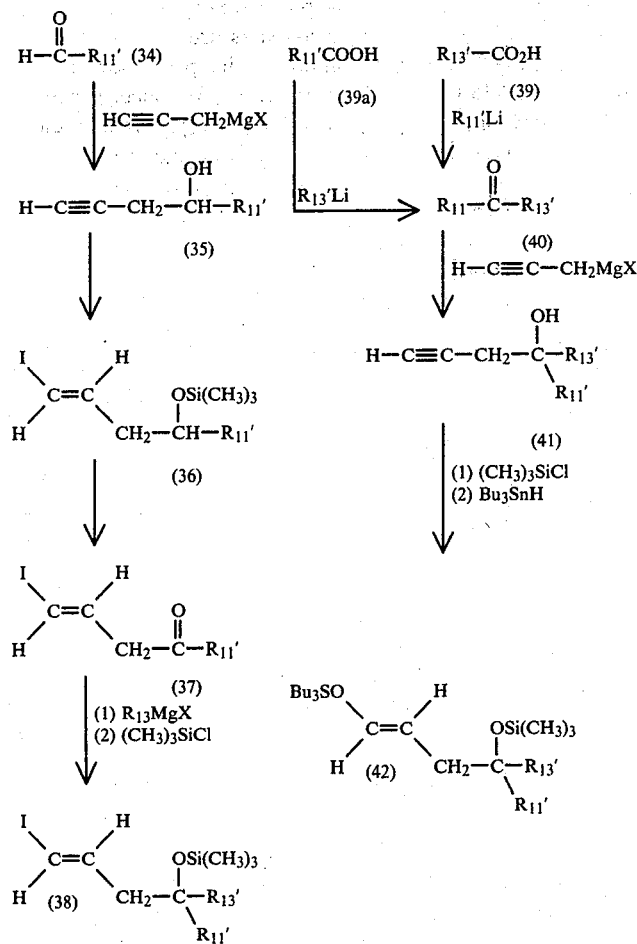

A preferred method for the preparation of vinyllithium precursor is also described in Flowsheet C. $-10°$ C. to $-78°$ C. generates the corresponding vinyllithium reagent.

FLOWSHEET D

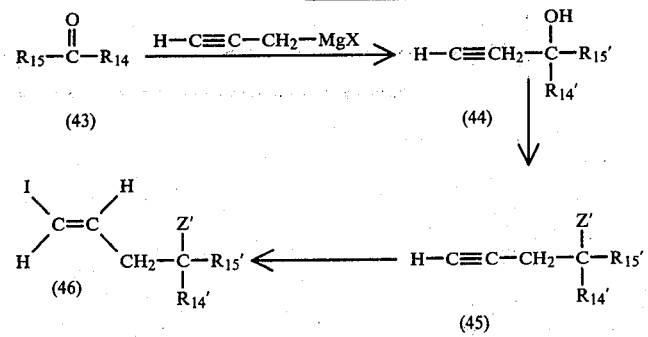

Treatment of the requisite carboxylic acid (39 or 39a) with the appropriate organolithium reagent ($R_{13}'Li$ or $R_{11}'Li$ respectively), wherein $R_{11}'$ and $R_{13}'$ are hereinabove defined, give the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of In accordance with flowsheet D hereinabove, the precursors for other 16-hydroxy prostaglandins are prepared by treating an appropriate aldehyde or ketone (43) with a propargylic magnesium halide to yield the requisite homopropargylic alcohol (44). The alcohol is protected as a tritylether (45) (for secondary alcohols) or as a trimethylsilyl ether (45) (for tertiary alcohols). These ethers are then converted to the appropriate trans-vinyliodide (46) by treatment with disiamylborane generated in situ from 2-methyl-2-butene, sodium borohydride, and boron trifluoride, followed by treatment with trimethylamine oxide and then iodine and sodium hydroxide, wherein $R_{15}'$ is hydrogen, methyl or ethyl; $Z'$ is $-O-C(C_6H_5)_3$ when $R_{15}'$ is hydrogen and $Z'$ is $-O-Si(CH_3)_3$ when $R_{15}'$ is methyl or ethyl; $R_{14}'$ is selected from the group $C_3$ to $C_5$ alkyl, $C_3$ to $C_5$-1-alkenyl and

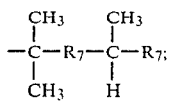

wherein $R_7$ is as described above with the proviso that when $R_{14}'$ is

then $R_{15}'$ must be hydrogen.

FLOWSHEET E

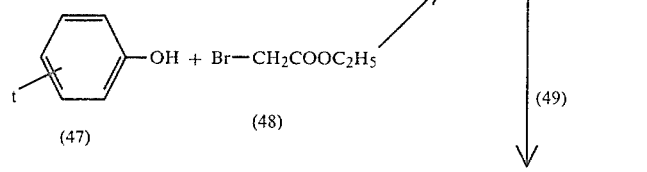

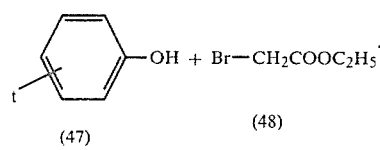

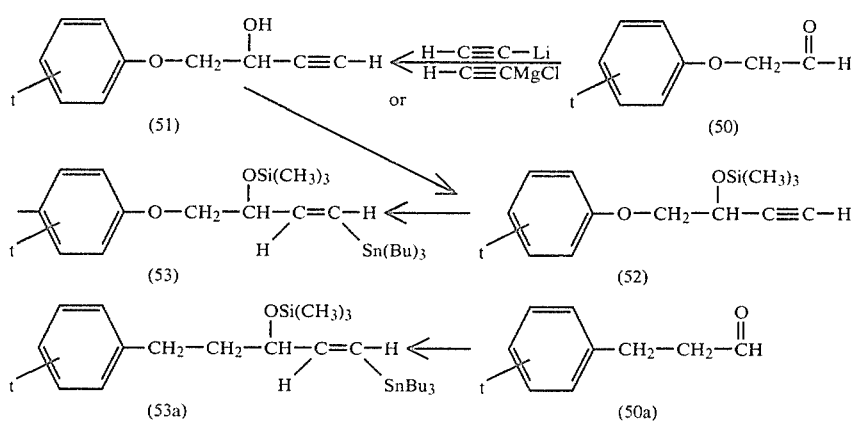

The preparation of the precursors for the synthesis of 16-aryloxy congeners is described in accordance with Flowsheet E. hereinabove. The aryl esters (49) are prepared by esterifying the commercially available acids or by treatment of ethyl bromoacetate with the appropriate phenol. The ester (49) is reduced to the aldehyde (50) which upon treatment with lithium acetylide or acetylene magnesium bromide provides the propargylic alcohol (51). Treatment of the alcohol (51) with chlorotrimethylsilane followed by tri-n-butyltin hydride furnishes the requisite vinylstannyl derivative (53). Similar treatment starting with substituted hydrocinnamaldehyde (50a) provides the respective vinylstannyl derivative (53a).

The preparation of the precursors for the synthesis of secondary 15-hydroxy congeners are described in the literature. The preparation of the precursor for 15-methyl-15-hydroxy is described in Flowsheet F hereinbelow. In accordance with Flowsheet F, an acid chloride, wherein $R_5$ is hereinabove defined, is treated with acetylene and aluminum trichloride to provide the vinylchloride (55) which upon treatment with sodium iodine furnishes the vinyliodide (56). Treatment of (56) with methylmagnesium halide followed by chlorotrimethylsilane gives the requisite protected vinyliodide (57)

FLOWSHEET F

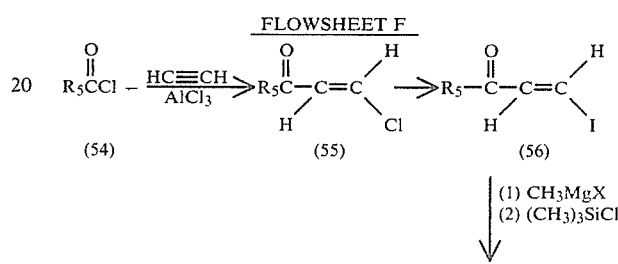

The precursors for the novel compounds of this invention which have a β chain represented by Formula K

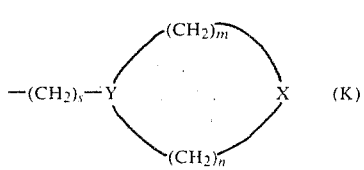

wherein s, Y, m, n, and X are herein above defined is shown in Flowsheet G and Flowsheet H.
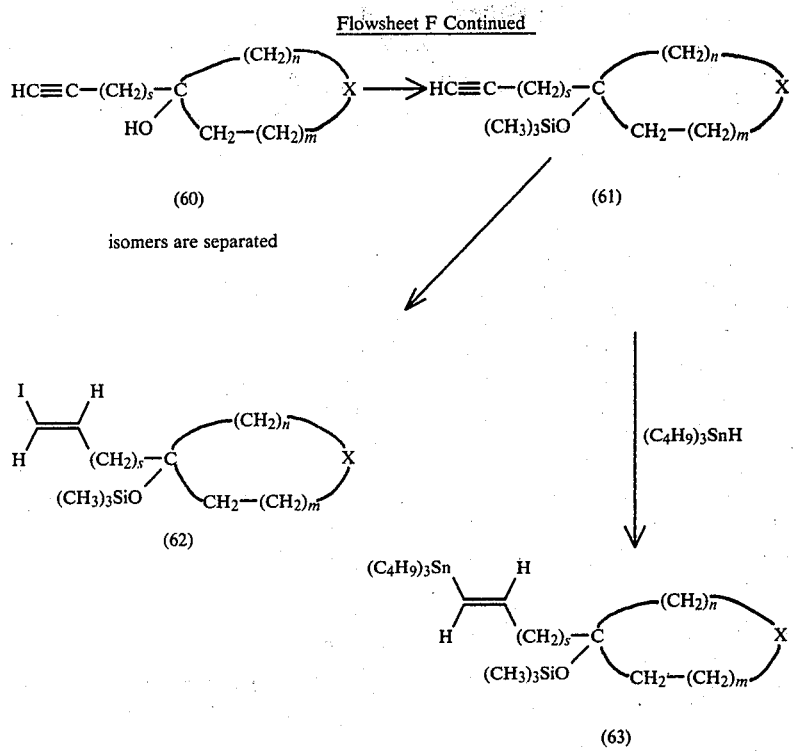
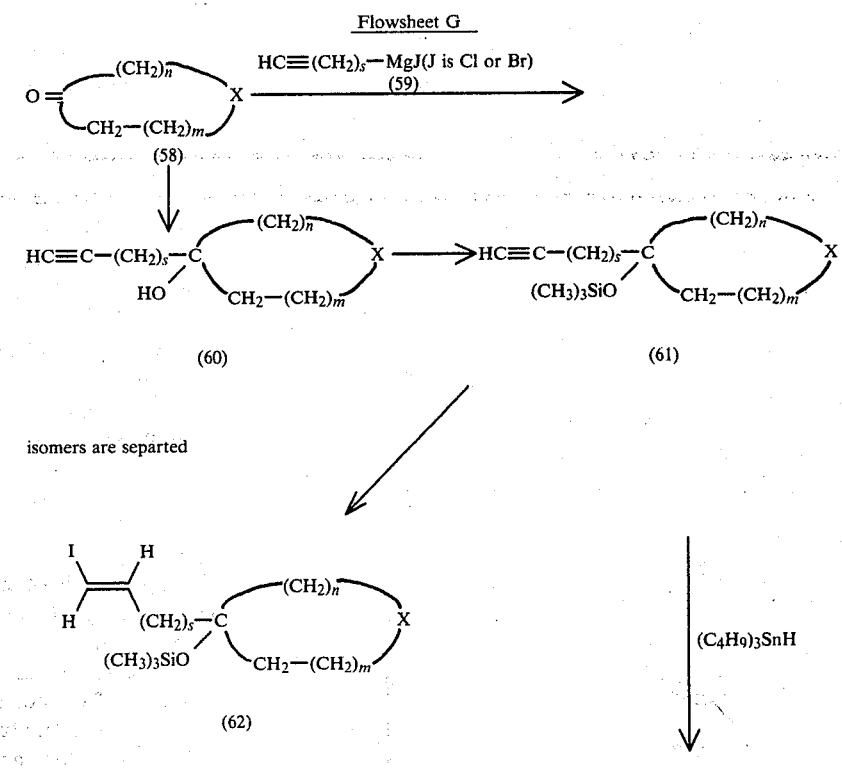

Flowsheet G -continued

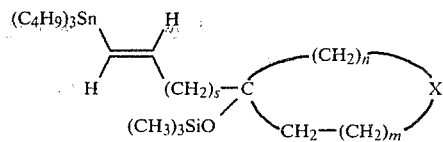

(63)

In accordance with the scheme as outlined hereinabove in Flowsheet G a ketone (58) is reacted with a Grignard reagent (59) such as acetylene magnesium chloride (59, s=0) or propargyl magnesium bromide ((59), g=1,) to give the acetylenic alcohol (60). In those cases where X is not -CH$_2$- two isomeric acetylenic alcohols are formed. These isomers can be separated by procedures well known to the art including fractional crystallization, fractional distillation and various chromatographic procedures. The individual isomers can then be carried through the remaining reactions outlined in Flowsheet G.

The acetylenic alcohol (60) is converted to its trimethylsilyl ether in the usual manner. The silylated derivative (61) is then treated with disiomaylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (62).

(63) is prepared by the addition of tri-n-butyl tin hydride to the acetylene (61) in the presence of bisazoisobutyronitrile followed by vacuum distillation at a high enough temperature (about 170° C.) to isomerize any of the cis-vinyl tin compound to the trans-vinyl tin compound.

Certain of the ketones (67) of this invention are prepared as indicated in Flowsheet H below:

FLOWSHEET H

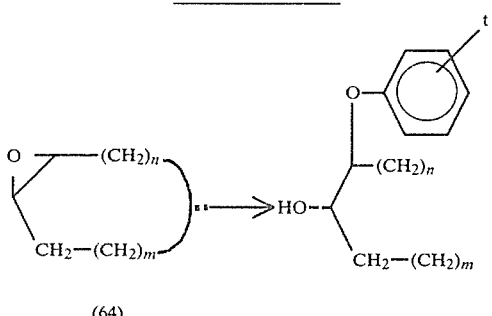

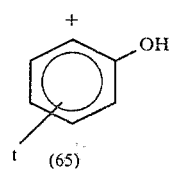

-continued
FLOWSHEET H

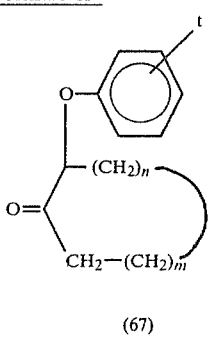

(67)

wherein n and m are as hereinabove defined and the moiety

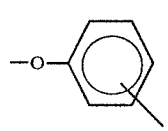

represents a phenoxy group which is optionally substituted with one or more halogen, trifluoromethyl, and C$_1$ to C$_4$ alkoxy groups.

As indicated in Flowsheet H the reaction of an epoxide (64) with a substituted or unsubstituted phenol (65) in the presence of a catalytic amount of aqueous sodium hydroxide and a phase transfer catalyst such as methyl tricapryly ammonium chloride and the like at 70°-80° C. gives the phenoxy substituted alcohol (66) which in turn is oxidized with an oxidizing reagent such as pyridinium chlorochromate in methylene chloride to give the phenoxy substituted ketone (67). This ketone (67) is then carried through the reactions shown in Flowsheet G above.

The other ketones (58) used in this invention are known in the literature or can be made by procedures well known to the art [G. Lardelli, U. Lamberti, W. T. Walles and A. P. de Jonge, Rec. Trav. Chem. Pays-Bas, 86 481 (1967); Ng. Ph. Buu-Hoi, T. B. Loc and Ng. Dat Xuong., Bull. Soc. Chem. France, 174 (1958); and G. H. Posner, Organic Reactions, 19, 1 (1972)].

The preparation of the cyclopentenones of this invention containing the hydroxyketone feature (68 a & b) where R$_1$ is hydrogen or a hydroxy group can be accomplished in several ways one of which involves the conversion of the corresponding cyclopentenone containing a carboxylate function (69 a & b) to the respective hydroxy ketone analog (68 a & b).

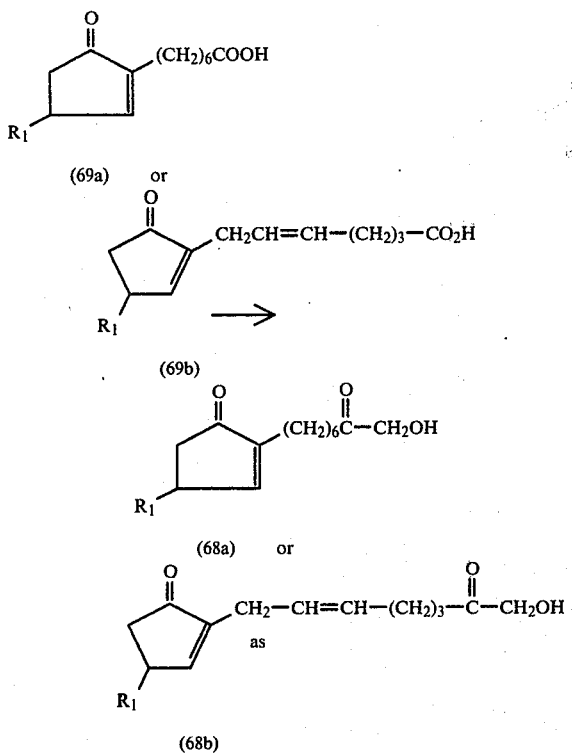

Most of the cyclopentenone carboxylic acids (69 a & b) required for the purposes of this invention have been described in the literature or can be prepared by procedures quite analogous to those already described. Appropriate references are provided herein. The synthesis of certain non-reference requisite cyclopentenone carboxylic acids (69 a & b) is also described herein.

The conversion of the cyclopentenone carboxylic acid (69 a & b) to the respective hydroxyketone analogs and the protection of these compounds for a conjugate addition reaction is described hereinbelow in Flowsheets J and K.

For the preparation of cyclopentenones of the type (79) whereas Z is the group $$-CH_2CH\overset{cis}{=}CH-(CH_2)_3- \text{ or } -(CH_2)_6-,$$

the carboxylic acid (76) is converted to the acid chloride (77) by first forming the sodium salt with sodium hydride in tetrahydrofuran (THF) and then reacting the resulting suspension with oxalyl chloride in the presence of a catalytic amount of dimethylformamide (DMF). The resulting acid chloride (77), dissolved in ether, is then added dropwise to an ether solution containing two to three equivalents of diazomethane to produce the diazoketone (78). The diazoketone can be hydrolyzed to the hydroxy ketone (79) by refluxing an ethereal solution in the presence of a dilute aqueous solution of sulfuric acid.

Alternately, the acid chloride (77) can be heated with two equivalents of a 1,1,2-tris-tri-$C_1$ to $C_4$ alkylsilyloxyethylene, preferably 1,1,2-tris-trimethylsilyloxyethylene at 90°-100° for 2 to 4 hours to produce compound (81). Compound (81) can be readily hydrolyzed and decarboxylated to give the hydroxy-ketone (79) by treatment with dilute hydrochloric acid in tetrahydrofuren.

Protection of the hydroxy ketone function of (79) suitable for a conjugate addition reaction, can be accomplished in two ways. Ketalization of (79) with ethylene glycol is accomplished by refluxing a benzene or toluene solution of (79) and ethylene glycol into a Dean-Stark trap. The resulting ketal (82) is then treated with trimethylsilylchloride (TMSCl) and imidazole in dimethylformamide (DMF) to give (83) which is suitably protected for a conjugate addition reaction.

Alternatively (79) can be protected by reaction with a mixture of 2-methoxy-1-propene (84) and 2,2-dimethoxypropane (85) in benzene in the presence of an acid catalyst such as p-toluenesulfonic acid to give the ketal (86) which is suitably protected for a conjugate addition reaction.

FLOWSHEET J

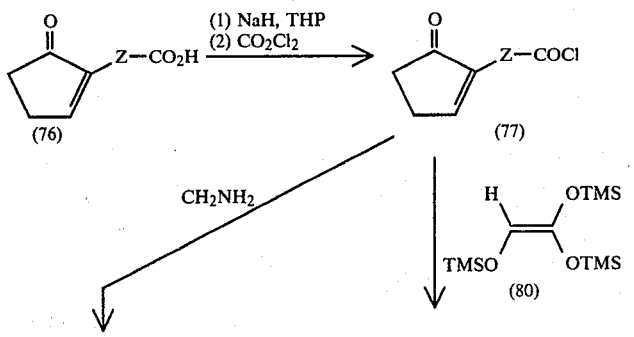

FLOWSHEET J -continued

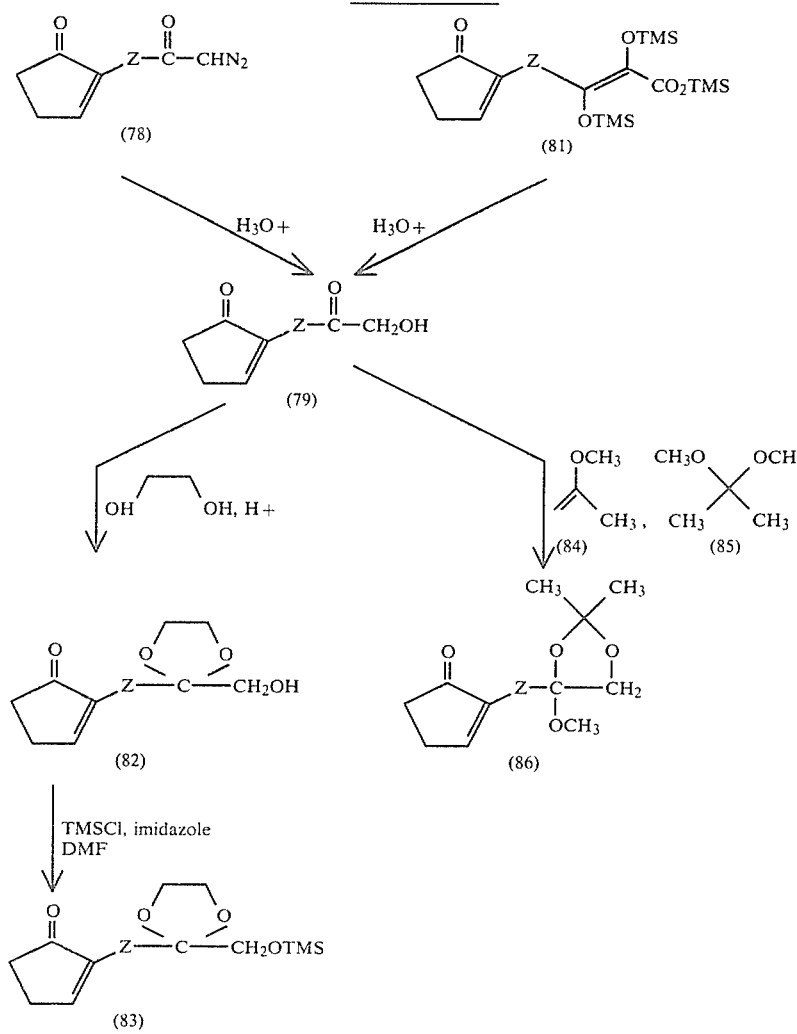

The preparation of the 4-hydroxycyclopentenone intermediates (92) wherein Z is hereinabove defined is outlined in Flowsheet K below. The reaction of the hydroxy acid (87) with at least two equivalents of di-methyl-t-butylsilylchloride in the presence of imidazole in dimethylformamide at 30°–40° C. gives the bis-dimethyl-t-butylsilated compound (88). The carboxylated dimethyl-t-butylsilyl group can be selectively removed by treatment with acetic acid, tetrahydrofuran and water (4:2:1) to give the carboxylic acid (89). The acid chloride (90) is prepared by first treating the acid (89) with sodium hydride in tetrahydrofuran to give the sodium salt. The resulting suspension of the sodium salt is then treated with oxalyl chloride in the presence of a catalytic amount of dimethylformamide. Alternatively the acid chloride (90) can be prepared directly by the reaction of the acid (89) or the dimethyl-t-butylsilyl ester (88) with oxalyl chloride in tetrahydrofuran in the presence of a catalytic amount of dimethylformamide at 0° C. The slow addition of an ethereal solution of the acid chloride (90) to an ethereal solution of two to three equivalents of diazomethane gives the diazoketone (91) which on acid hydrolysis gives the 4-hydroxycyclopentenone (92) containing the hydroxyketone function.

Alternatively the acid chloride (90) can be heated with at least two equivalents of a 1,1,2-tris-tri-$C_1$ to $C_4$ alkylsilyloxyethylene, preferably 1,1,2-tris-trimethylsilyloxyethylene, at 90°–110° C. in the absence of solvent to give (93) which is readily hydrolyzed and decarboxylated to give the 4-hydroxycyclopentenone (92) containing the hydroxyketone feature. Protecting of (92) can be accomplished by treatment with an excess mixture of 2-methoxy-1-propene (84) and 2,2-dimethoxypropane (85) in benzene with an acid catalyst such as p-toluenesulfonic acid to give the bis-ketal (94) which is suitably protected for subsequent conjugate addition reactions.

Alternatively, the two hydroxyl moieties may be protected using 2 equivalents of 2-methoxypropene per equivalent of (92) in the presence of a catalyst such as chloroacetic acid to provide compounds such as (94A). Other useful protecting groups are dihydro-2H-pyran, ethylvinylether and the like.

Other acid sensitive protecting group for the two hydroxyl groups are the tri-$C_1$ to $C_4$-alkylsilyls (from silylchlorides), triphenylmethyl (from tritylchloride or bromide), mono-p-methoxytriphenylmethyl (from mono-p-methoxytriphenylmethylchloride or bromide), methoxymethyl (from chloromethylmethylether) and the like.
Treatment of (88) with an oxalylhalide such as oxalylchloride or oxalylbromide is productive of the acid chloride (90).
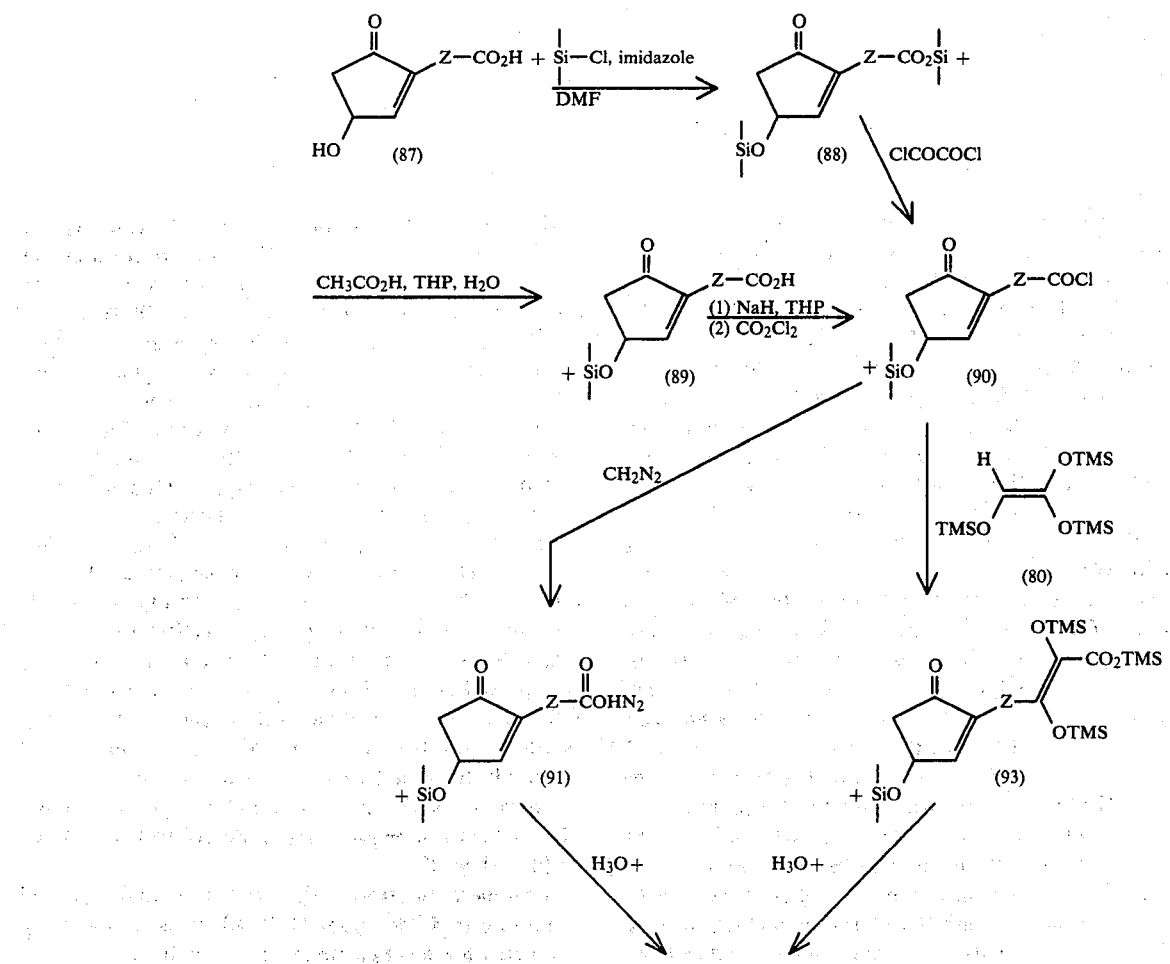

FLOWSHEET K -continued

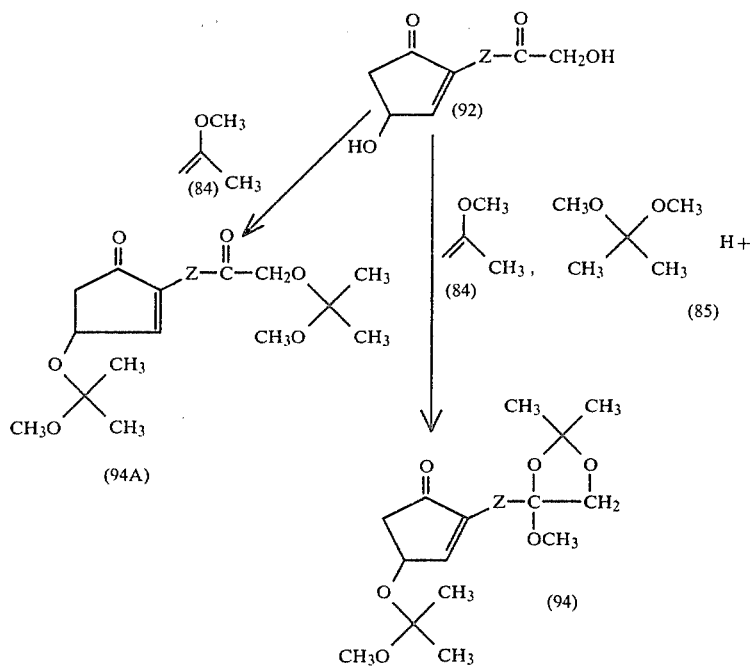

Another preparation of the 4-hydroxycyclopentenone intermediates which contain a cis double bond in the potential a chain (109) is shown hereinbelow in Flowsheet L wherein g is as hereinabove defined. As illustrated in Flowsheet L there are three methods available to prepare the important intermediate (98). The reaction of the ω-bromo carboxylic acid (95) with oxalyl chloride in an inert solvent such as benzene gives the acid chloride (96). Addition of the acid chloride (96) in ether to an ethereal solution of diazomethane (2 to 3 equivalents) yields the diazoketone (97) which can be hydrolized in a two phase system consisting of ether and dilute sulfuric acid to the hydroxyketone (98). Alternatively the acid chloride (96) can be treated with an excess of a 1,1,2-tris-tri-$C_1$ to $C_4$ alkylsilyloxyethylene, preferably 1,1,2-tris-trimethylsilyloxyethylene in the presence of a catalytic amount of stannic chloride in the absence of solvent to give compound (99) which can readily be hydrolized and decarboxylated to the desired hydroxyketone (98) using dilute hydrochloric acid in tetrahydrofuran. An alternate method to prepare (98) involves the reaction of the bromoolefin (100) with aqueous n-bromosuccinimide (NBS) in the presence of a catalytic amount of acetic acid to give a mixture of bromohydrins (101) and (102). Oxidation of the mixture of bromohydrins with an oxidizing agent such as pyridinium chlorochromate in methylene chloride gives a mixture of bromoketone (103) and bromoaldehyde (104). Refluxing this mixture with sodium formate in methanol then gives the desired intermediate (98). Protection of the ketone function of (98) is accomplished using ethylene gycol in refluxing toluene with a catalytic amount of p-toluenesulfonic acid. The ketal (103) is then reacted with dimethyl-t-butylsilylchloride and imidazole in dimethylformamide to give the fully protected compound (104). The phosphonium salt (105) is obtained by refluxing a solution of (104) and triphenylphosphine in acetonitrile. Treatment of the phosphonium salt (105) with sodium methylsulfinylmethide in dimethylsulfoxide generates a phosphonium ylid which on reaction with aldehyde (106) gives (107). Refluxing a water-dioxane solution of (107) in the presence of a phosphate buffer (pH 5 to 6) gives the cyclopentenone (108). Treatment of (108) with chloral and triethylamine in ether gives (109) which on hydrolysis in a mixture of tetrahydrofuran and dilute hydrochloric acid at 50°–70° C. then gives the desired 4-hydroxycyclopentenone (110) which can be protected as described hereinabove in Flowsheet K.

Treatment of (109) with trimethylsilylchloride and imidazole in DMF gives (111) which is also suitably protected for a conjugate addition reaction.

FLOWSHEET L
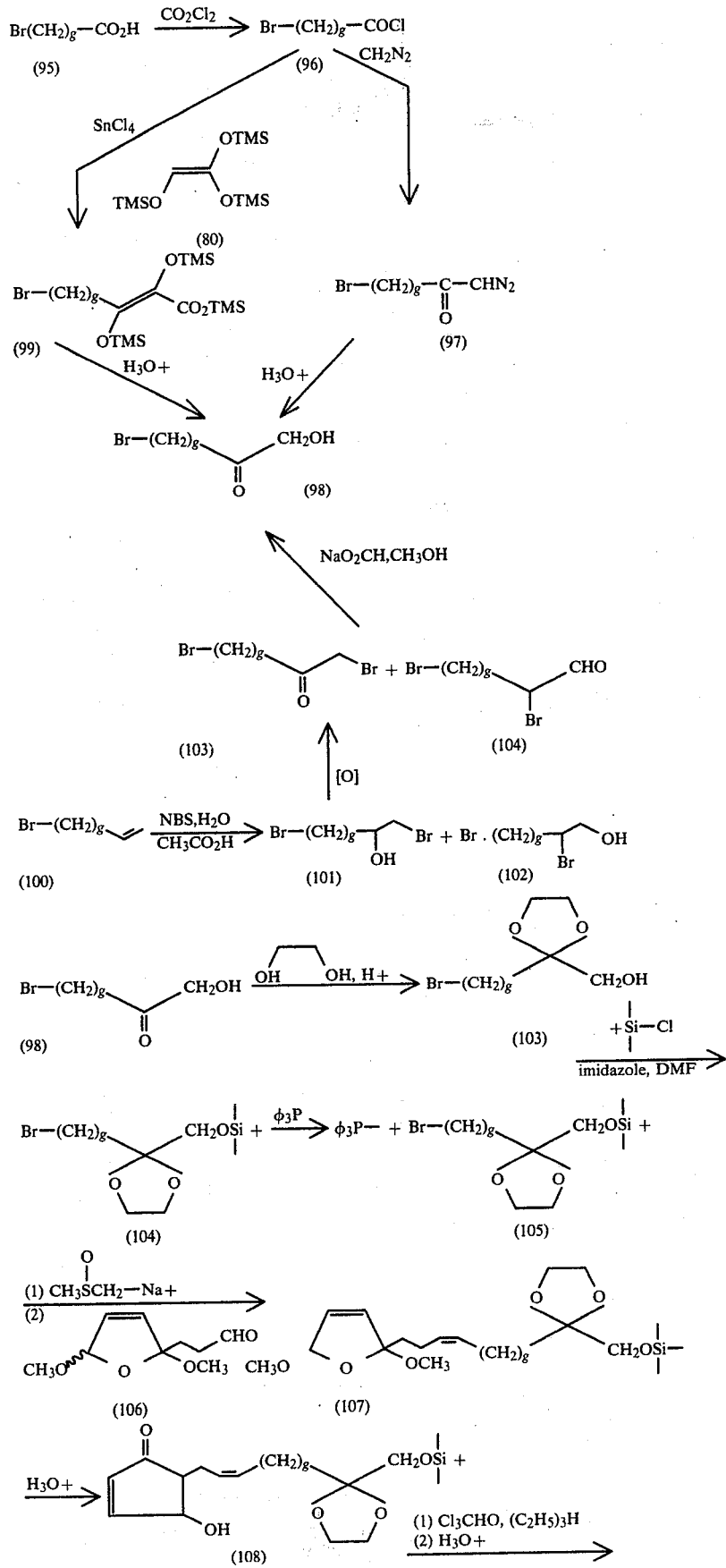

-continued
FLOWSHEET L

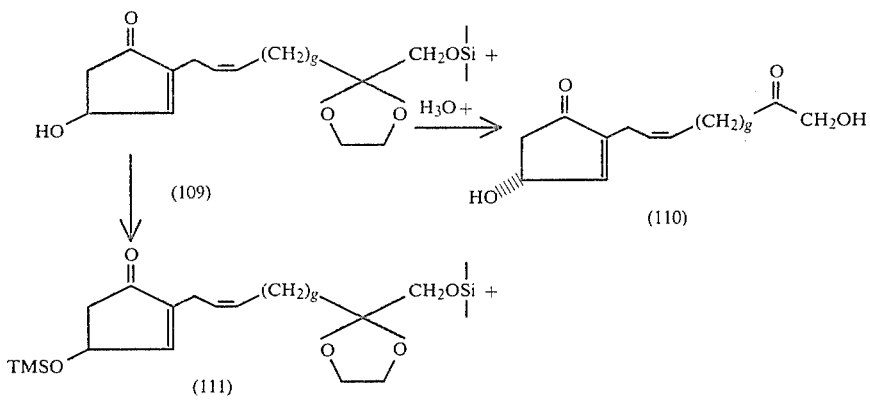

The preparation of the reagent 1,1,2-tris-tri-$C_1$ to $C_4$ alkylsilyloxyethylene is described below using, as the illustrative compound 1,1,2-tris-tri-methylsilyloxyethylene (80). The reaction of glycolic acid with 1,1,1,3,3,3-hexamethyldisilazane and trimethylsilylchloride in pyridine gives bis-trimethylsilated glycolic acid (113), see Flowsheet M. Addition of (113) to a tetrahydrofuran solution of one equivalent of lithium 1,1,1,3,3,3-hexamethyldisilazane amide at −78° C. generates a lithium enolate which is trapped with trimethylsilylchloride to produce the desired reagent (80).

FLOWSHEET M

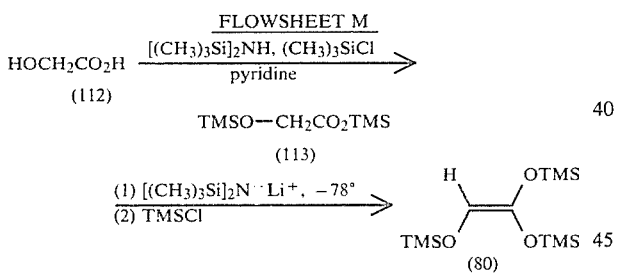

The preparation of the prostaglandin congeners of this invention are described hereinbelow in Flowsheet N where in Z is as hereinabove defined; $R_3''$ is hydrogen, 2-methoxypropyl-2-oxy (—OC(CH$_3$)$_2$OCH$_3$) or trimethylsilyloxy; $R_3'''$ is hydrogen or hydroxy; T' is the radical

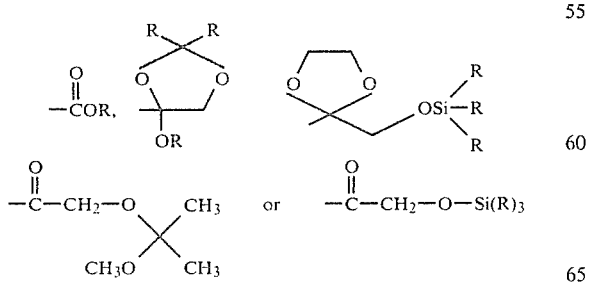

wherein R is as hereinabove defined. R' is selected from the group consisting of:

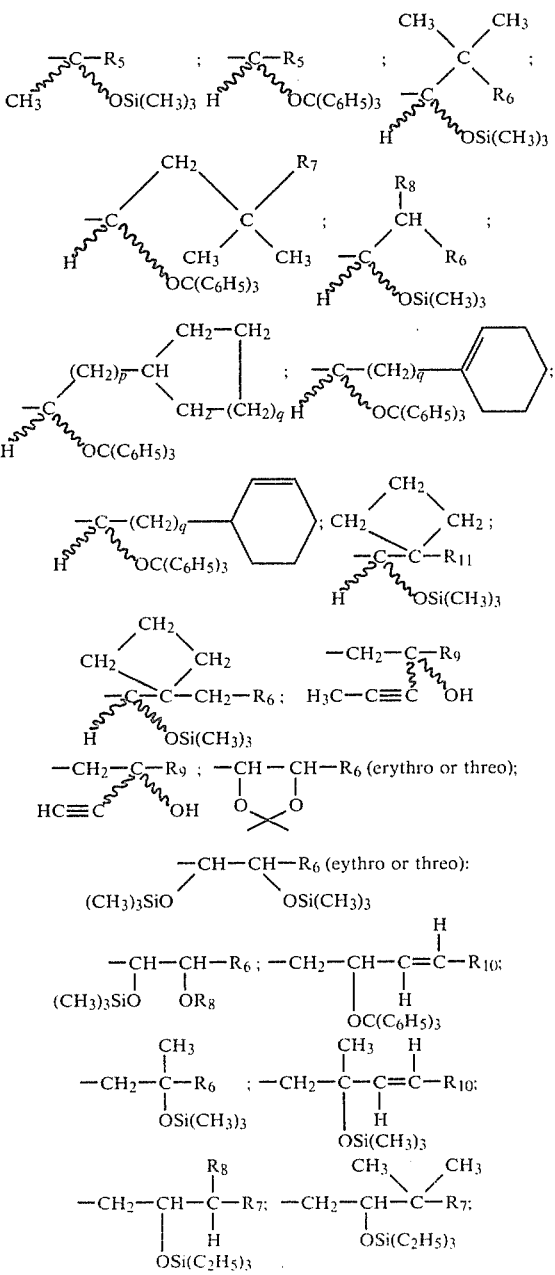

-continued

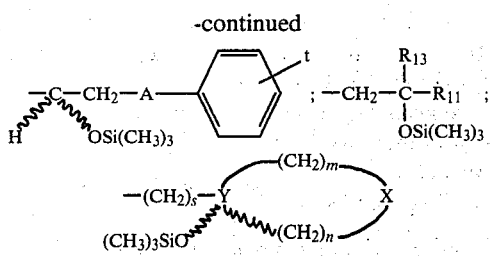

wherein $R_5$, $R_6$, $R_7$, $R_8$, $R_9$, $R_{10}$, $R_{11}$, $R_{13}$, A, p, q, t, s, m, n, Y, and X are as hereinabove defined.

In accordance with Flowsheet N the vinyliodine (114) is treated with either one equivalent of n-butyllithium or 2 equivalents of t-butyllithium at low temperature, preferably $-30°$ to $-70°$ C. in an inert solvent, eg. hexane, ether or toluene to provide the trans alkenyllithium reagent (116).

Alternatively, the vinyllithium reagent (116) can be prepared by treatment of a vinylstannyl derivative such as (115) with n-butyllithium at $-10°$ to $-78°$ C. in ether or THF.

For the preparation of the asymmetrical lithio cuprate (117) or the like, a solution of one molar equivalent of copper (I)-1-alkyne, preferably copper (I)-1-pentyne in anhydrous hexamethylphosphorous triamide preferably one to five molar equivalents, and anhydrous ether is added to one molar equivalent of the aforementioned vinyllithium solution cooled to about $-78°$ C. After about one hour at this temperature, a molar equivalent of the requisite cyclopentenone (120) is added. After several hours at $-78°$ C. to $-20°$ C. the reaction mixture is quenched with aqueous ammonium chloride solution and the blocked product (121) is isolated in the usual manner.

It is also possible to effect conjugate 1,4-addition with the asymmetrical lithio cuprate (119) derived from vinyllithium (116) and cuprous thiophenoxide. A solution of vinyllithium (116) in ether at $-78°$ C. is reacted with an equimolar amount of a reagent prepared by admixture, in ether at a temperature of $0°$ C. to $-78°$ C., of equimolar amounts of cuprous thiophenoxide and copper (I) iodide tributylphosphonium complex. After about 30 minutes at this temperature, the lithio cuprate (119) is treated with the requisite cyclopentenone (120) as described hereinabove for the conjugate addition with 1-alkynyl lithio cuprate (117).

For the preparation of the symmetrical lithio cuprate (118) one molar equivalent of copper (I) iodide tributylphosphine complex, dissolved in anhydrous ether, is added at about $-78°$ C. to two molar equivalents of the aforementioned vinyl lithium (116) solution in hexanes, cooled to $-78°$ C. After about one hour at this temperature, the lithio cuprate (118) is treated with the requisite cyclopentenone (120) as describe hereinabove for the conjugate addition with the 1-alkynyl lithio cuprate (117).

The procedures for conjugate addition involving organocopper reagents are well known in the art, see for example, C. J. Sih, et al., J. A. C. S., 97, 865 (1975).

All available evidence leads us to believe that the $-CH=CH-R'_2$ function introduced by the cuprate process occupies a position trans to the 11-oxy function.

Similarly, we are led to the conclusion that in the product (121) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8e. In order to ensure a trans-relationship in (121) these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

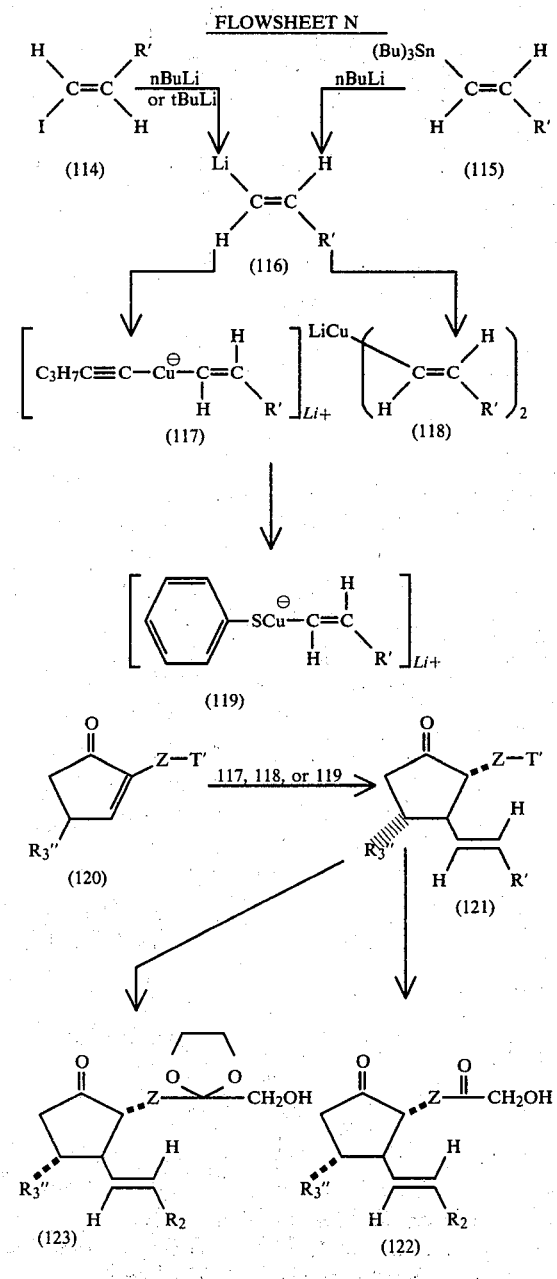

FLOWSHEET N

When T' is

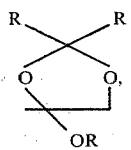

removal of the blocking groups from (121) to give the prostaglandin congener (122) is accomplished by treatment of (121) with a mixture of acetic acid, tetrahydrofuran and water (4:2:1) at 25° to 55° C.

When T' is

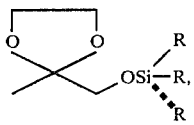

(121) can be partially deblocked to give ketal (123) by treatment of (121) with 0.6 N hydrochloric acid in tetrahydrofuran at room temperature for 4 to 7 hours.

The compounds of the present invention of formula I where G is

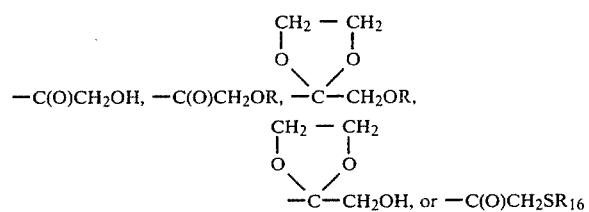

and where V is bromo, chloro or iodo are conveniently prepared by the iodine catalyzed oxidation of a 9α,11α-dihydroxy-1-ethylenedioxy-1-hydroxymethyl (or alkoxymethyl)-5-cis-13-trans-prostadiene (151) or (152) in an inert organic solvent, at about −10° to about 20° is contacted with a solution of iodine, (or bromine and chlorine) also in an inert organic solvent, for time sufficient to complete the epoxidation reaction, i.e., from about 15 minutes to about 48 hours. The mole ratios of (151): iodine are in the range of 10:1 to 1:1, preferable 8:1 to 3:1. The reaction proceeds favorably in the presence of basic organic or inorganic catalysts, preferably sodium bicarbonate. Inert organic solvents useful in the above reaction include diethylether, tetrahydrofuran, dimethylformamide, and the like.

The compounds of formula (151a) are converted to the compounds of formula (151b) by a reaction in acid media. The reaction is conveniently carried out in an aqueous inert organic solvent solution, such as the organic ether solvents illustrated previously, at temperatures and times familiar to those skilled in the art of hydrolysis of ketals, typically about room temperature to about 75° for about 1 hour to about 48 hours.

Compounds (151a) may be converted to their analogous dehalogenated compounds (151c) by treatment with a trialkystannane such as tributylstannane and a free radical source such as azobisisobutyronitrile. The reaction is typically carried out at room temperature to about 75° for about 15 minutes to about 48 hours. The product is obtained by conventional separation procedures such as extraction or chromatography. The hydrolysis of the ketal moiety of (151c) as described hereinabove gives the dehalogenated compounds (151d).

As a further embodiment for the preparation of the compounds of formula I, in the cases of the compounds where G is —C(O)OR, or C(O)OH, a 1,4-dihydroxy-2-(5-cisoctenoate)-3—$C_{13}C_{14}$—$R_2$ substituted cyclopentane (152, Flowsheet S) is epoxidized in an inert organic solvent at about −10° to about 20° for time sufficient to complete the epoxidation reaction, i.e., from 15 minutes to about 48 hours. The mole ratios of octenoate:iodine, are in the range of 10:1 to about 1:1, preferably about 8:1 to about 3:1. The compounds of the present invention formed from this reaction, compounds (151e) where $R_1$ is $C_1$-$C_6$ alkyl are dehalogenated as described earlier for the compounds (151b) to compounds (151c), i.e., with a free radical source in the presence of a trialkylsilane, forming the compounds of the present invention (151f). Compounds (151e)i can be hydrolyzed to remove the group $R_1$ where such is $C_1$-$C_6$ alkyl giving the free carboxylic acid, compounds (151e)ii. The hydrolysis reaction is preferably conducted in a protic solvent such as methanol, ethanol and the like using a strong base, for example, sodium hydroxide, at −10° to about 30° for about from 15 minutes to about 48 hours. Conventional techniques such as extractive or chromatographic techniques can be used to isolate the desired product.

Alternately, compounds (151e)ii can be prepared from an analogous 1,4-dihydroxy-4-cis-1-heptenoic acid by first protecting the hydroxyl functionality at position 4 with a suitable protecting group such illustrated by the group tetrahydropyran-2-yl or trimethylsilyloxy. Protection of the hydroxyl functionality in the chain $C_{13}$-$C_{14}$-$R_2$ must also be effected such preferably by tritiation of such hydroxyl functionality. The starting compound in such cases is illustrated as seen in Flowsheet T by Intermediate compound C, 9α-hydroxy-11α-tetrahydropyranyloxy-16-tritlyloxy-17-methyl-5-cis,13-trans-prostadienoic acid.

The preparation of the precursors to the intermediates used in the preparation of the compounds of formula I is illustrated by Flowsheet U. In Reaction Step 1,2-[8-hydroxy-7-(ethylenedioxy)-2-cis-octenyl]-4-hydroxycyclopent-2-en-1-one (151h) is prepared by treatment of 2-(8-hydroxy-7-oxo-2-cis-octenyl)-4-hydroxycyclopent-2-en-1-one (151g) with ethylene glycol and Amberlyst resin, preferably Amberlyst 15 resin. This reaction, is set forth herein in the examples. The aforementioned ketal is then treated with chlorotrimethylsilane to effect reaction of the free hydroxy groups at the 4-position of the cyclopentane nucleus and at the 8-position of the octenyl ketal giving (151i). Such reaction, forming the trimethylsilyloxy substituent at these positions is well known to those skilled in the art as affecting a protecting reaction of free hydroxyl groups, such being readily removed when desired at a later time. In Reaction Step 3, the 3-position of the cyclopentenolone nucleus is substituted with a desired hydrocarbon chain by a cuprate conjugate addition reaction as described hereinabove to give (151j) after removal of the protecting groups as described hereinabove and in the examples to follow.

The 2,3-cyclopentanolone of Reaction Step 3, (151j) is then converted to the cyclopentane-1,4-diol (151) by treatment of the product from Reaction Step 3 with lithium selectride at reduced temperature, thus forming (151) Intermediate A. This reaction path is known to those skilled in the art and is described in the preparations herein. The product of Reaction Step 3 may also be treated in a dehydrolysis reaction to remove the ketal group incorporated in the side chain at the 2-position of the cyclopentane nucleus. This reaction, shown as Reaction Step 5, in a manner to that described earlier for the preparation of compounds (151b) from the compounds (151a), and is set forth with particularity in the examples herein.

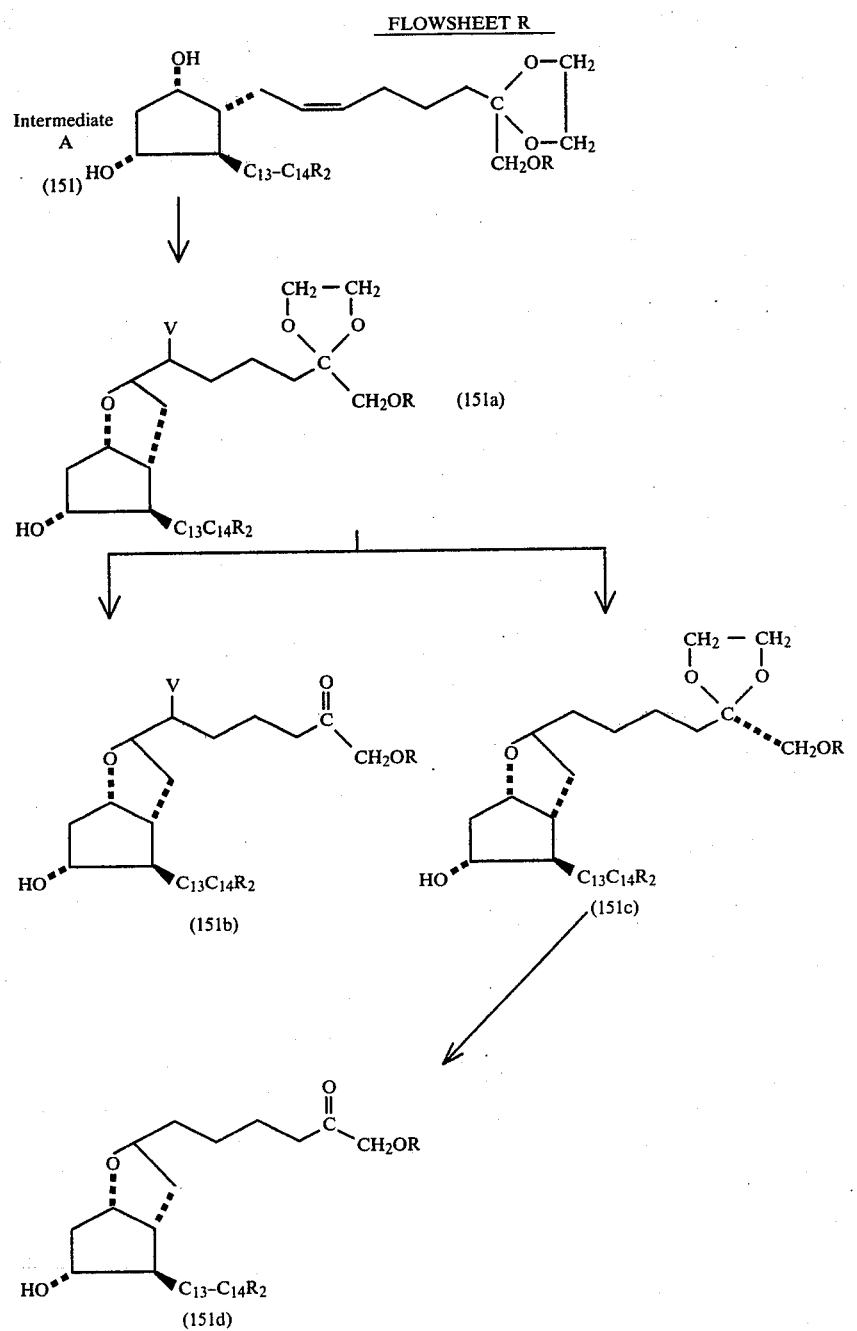

4,235,924
47 48
FLOWSHEET S
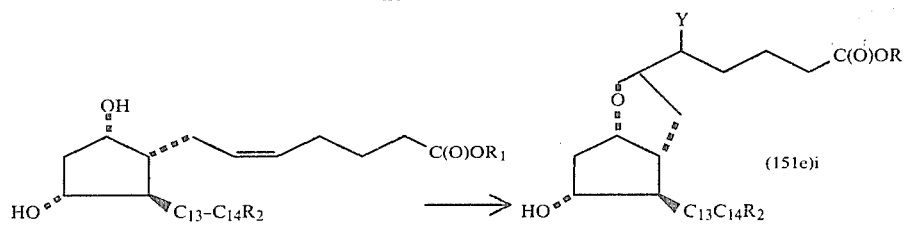
Intermediate B
(152)
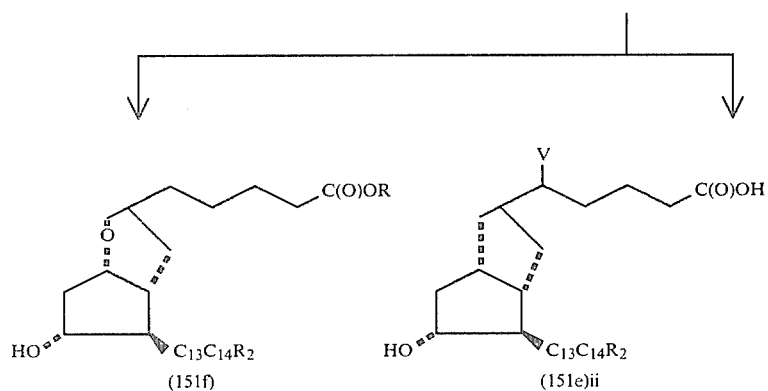
FLOWSHEET T
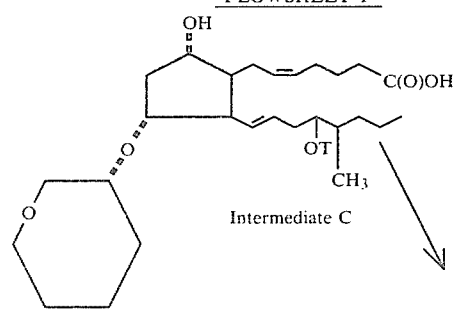
Intermediate C
-continued
FLOWSHEET T
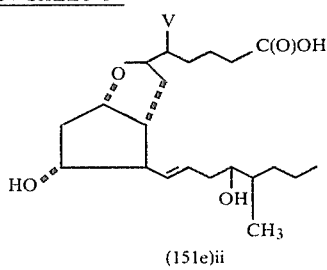
(151e)ii
FLOWSHEET U
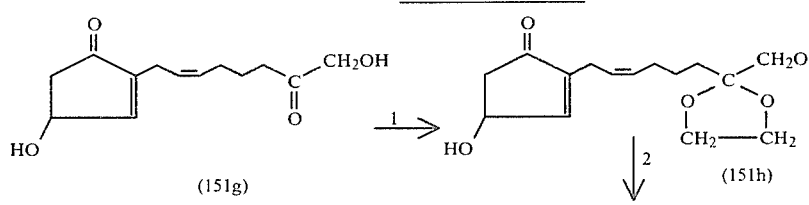
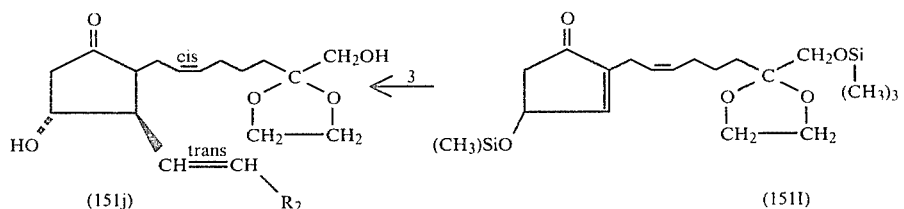

-continued
FLOWSHEET U

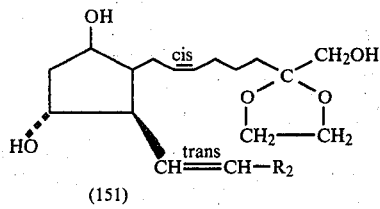
(151)

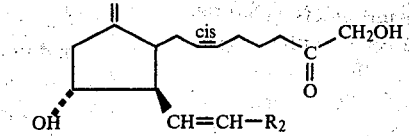

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See G. Fallick, American Laboratory, 19–27 (August, 1973) as well as references cited therein. Additional information concerning high speed liquid chromatography and the instruments necessary for its application is available from Waters Associate, Inc., 30 Maple Street, Milford, Mass.]

It is also possible to prepare the compounds of this invention in their optically active forms by the conversion of the optically active 4-hydroxycyclopent-2-en-1-one carboxylic acids (128) to the optically active protected hydroxy ketone analog (129) using the methods outlined hereabove in Flowsheet K.

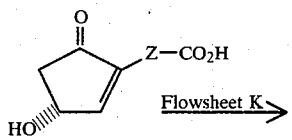

R configuration at $C_{11}$
(128)

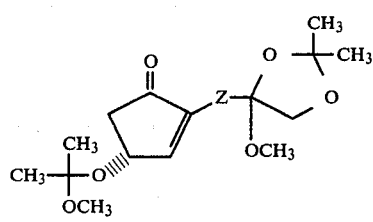

R configuration at $C_{11}$

In accordance with the following reaction scheme prostanoids are prepared as described by Stork in J.A.C.S. 97, 4 (1975) and J.A.C.S. 97 6260 (1975).

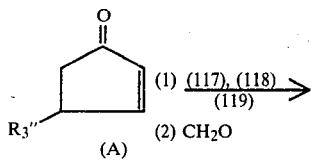

-continued (B)

(C)

(D)

Treatment of the protected 4-oxycylcylopentenone (A) with a cuprate such as (117), (118) or (119) as hereinabove defined, followed by quenching with formaldehyde to provide the hydroxymethyl analog (B) which is dehydrated with reagents such as excess methansulfonyl chloride in pyridine followed by treatment of the crude mesylate with diissopropylethylamine in ether overnight. $R_3''$, $R_3'''$ and $R_2$ are as previously defined. Addition of the methylenecyclopentanone (C) to a solution of the grignard $Mg(CH_2)_fR_1$ wherein f is as previously defined and $R_1$ is protected by a suitable blocking group such as 2-methoxy-propyl-2-oxy, and a catalytic amount of $Bu_3P.CuI$ ($Bu_3$ is tertiary butyl) followed by mild hydrolysis of the adduct provides the product prostanoid (D) wherein f, $R_3'''$ and $R_2$ are as previously defined.

The bromide precursor to the Grignard described above is prepared in accordance with the procedure of Flowsheet L.

Conjugate addition of the vinyl cuprates to (129) followed by deblocking as described hereinabove in Flowsheet N then gives the compounds of this invention in their optically active forms. Although in some cases two diastereoisomers will be formed, each optically active, they can be separated by chromatographic procedures as described hereinabove.

The preparation of optically active 4-hydroxy-cyclopent-2-en-1-ones such as (128) is described hereinbelow.

The 4-hydroxycyclopentenone racemates may be resolved into their component enantiomers (130) and (131) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride [to give (132)], (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (130) and (131). A useful procedure for the resolution of a 4-hydroxycyclopentenone racemate via an oxime such as (132) is described in the art [R. Pappo, P. Collins and C. Jung, Tetrahedron Letters, 943 (1973)].

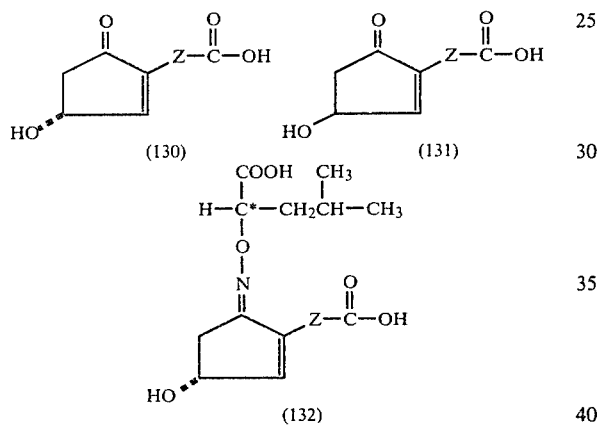

An alternate procedure for the preparation of the 4(R)-hydroxycyclopentenone enantiomers such as (130) involves as a key step the selective microbiological or chemical reduction of trione (133) to the 4(R)-hydroxycyclopentanedione (134). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate in the presence of one equivalent of organic base, such as triethylamine.

Conversion of hydroxycyclopentanedione (134) to an enol ether or enol ester, (135, Z=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (135) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (136). The ester (136), can then be hydrolyzed to acid (130).

For a description of these procedures in the art see: C. J. Sih, et al, J. A. C. S., 95, 1676 (1973); J. B. Heather, et al., Tetrahedron Letters, 2213 (1973); R. Pappo and P. W. Collins, Tetrahedron Letters, 2627 (1972); and R. Pappo, P. Collins, and C. Jung, Ann. N.Y. Acad. Sci., 180, 64 (1971).

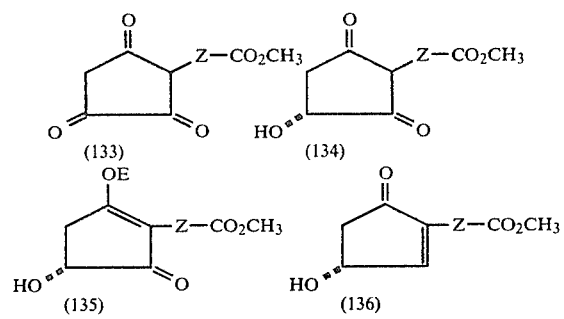

Procedures for the preparation of the requisite cyclopentanetriones (133) are well-established in the art and generally involve the treatment of an ω-1-oxo long chain ester (137) with methyl or ethyl oxalate and a base such as sodium methoxide in methanol, followed by treatment with dilute hydrochloric acid in aqueous methanol to effect the dealkoxalylation of the intermediate (138). See J. Kutsube and M. Matsui, Agr. Biol. Chem., 33 1078 (1969); P. Collins, C. J. Jung and R. Pappo, Israel Journal of Chemistry, 6, 839 (1968); R. Pappo, P. Collins and C. Jung, Ann. N.Y. Acad. Sci., 180, 64 (1971); C. J. Sih, et al., J. A. C. S., 95, 1676 (1973) (see reference 7); and J. B. Heather, et al., Tetrahedron Letters, 2313 (1973) for pertinent background literature.

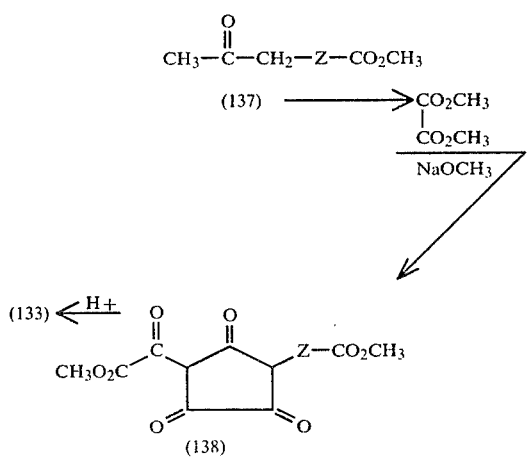

The intermediate keto esters (137) may be prepared by a variety of methods known to the art. One useful procedure is outlined below and involves alkylation of ethyl sodium salt (139) in the usual manner with the appropriate side-chain precursor (140, X=Cl, Br, I, preferably Br or I) followed by decarbethoxylation and reesterification, all in the usual manner.

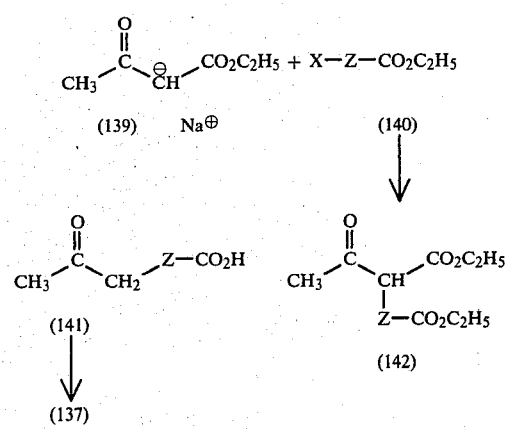

The side-chain precursors (140) are commercially available where Z is —(CH$_2$)$_p$—, and can be prepared as described in Belgian Patent 786,215 (opened to inspection January 15, 1973).

It is also possible to resolve the 4-hydroxycyclopentenone racemate (143) by microbiological means. Thus, treatment of the 4-O-alkanoyl or aroyl derivatives (144, R$_{18}$=aryl or alky) of racemate (143) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (145), which is then separated from the unreacted 4(S)-O-acyl enantiomer (146) by chromatographic procedures. After separation, mild hydrolysis of the 4(S) derivative (149) provides the 4(S)hydroxycyclopentenone (147). [See N. J. Marsheck and M. Miyano, Biochima et Biphysica Acta, 316, 363 (1973) for related examples.]

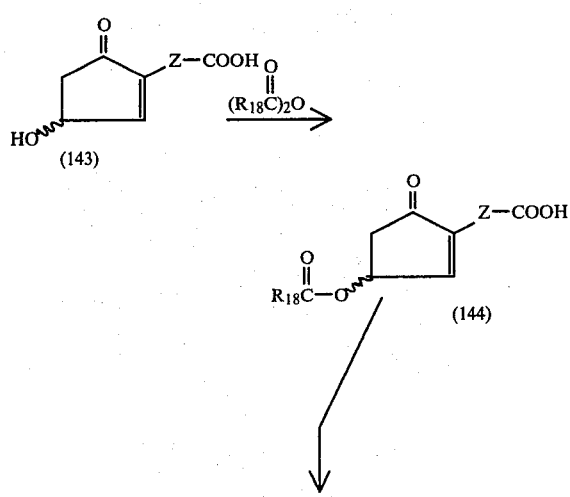

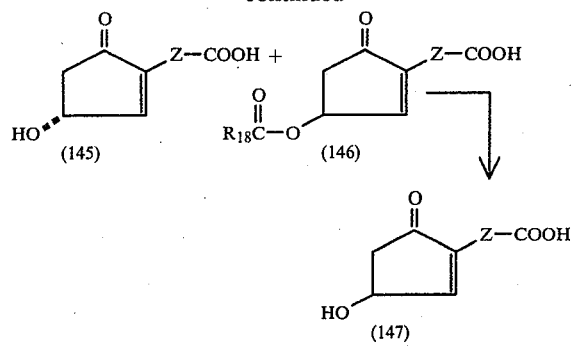

It is also possible to prepare the individual 4-hydroxycyclopentenones (145) and (147) directly by selective microbial hydroxylations of the corresponding 4-unsubstituted cyclopentenone (148). For example, with Aspergillus niger ATCC 9142; a selective 4(R)-hydroxylation of [148,Z=(CH$_2$)$_6$] has been reported; see S. Kurozumi, T. Tora and S. Ishimoto, Tetrahedron Letters, 4959 (1973). Other microorganisms can also accomplish this hydroxylation.

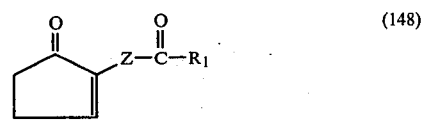

The 9α-hydroxy PGF precursor compounds are prepared by a conjugate addition reaction as described hereinabove in Flowsheet N. The initial conjugate addition product (121) (wherein Z, T', R$_3$" and R' are as hereinabove defined) is not deblocked but dissolved in tetrahydrofuran. An excess of lithium perhydro-9b-boro-phenalyhydride (PBPH) in tetrahydrofuran is added at −78° C. After warming to 0° C., the reaction mixture is quenched with saturated ammonium chloride solution. The product is isolated and deblocked with acetic acid-tetrahydrofuran-water 4:2:1 at 40° C. in the cases where T' is

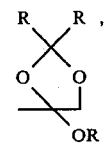

and with dilute hydrochloric acid in the cases where T' is

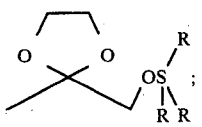

to give the precursor 9α-hydroxy compounds. See Flowsheet P hereinbelow wherein Z, T', R$_3$" are as hereinabove defined.

FLOWSHEET P

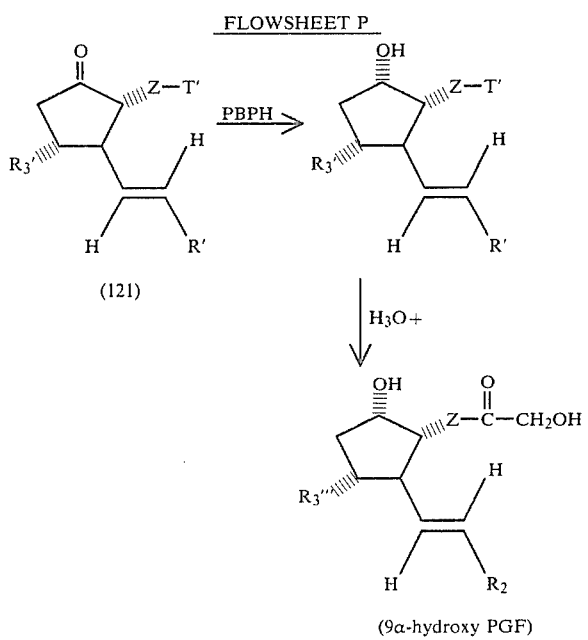

The 1-hydroxymethyl group of the compounds of Formula Ia can be selectively esterified by dissolving the free hydroxy compounds in pyridine and adding one equivalent of an anhydride $(R_{15}$—$CO)_2O$ or the acid chloride

and allowing the mixture to stand overnight to give the desired esters (153).

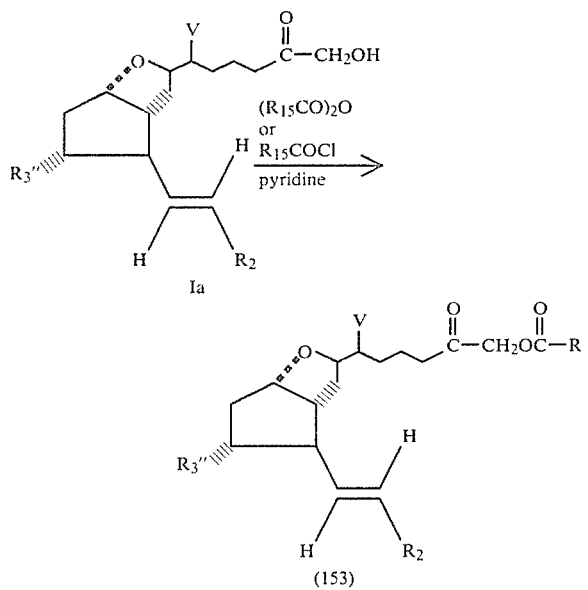

$R_{15}$ is phenyl substituted with one or more groups such as alkyl $(C_1$–$C_4)$, OR, SR, F, Cl, dialkylamino or $C_2$–$C_4$ alkyl, wherein R is $C_1$–$C_4$ alkyl. The E-Series compounds (122) may also be esterified by this procedure.

The novel prostacyclin compounds of the present invention have potential utility as hypotensive agents, vasodilators, anit-ulcer agents, agents for the treatment of gastric hypersecretion and gastric erosion, agents to provide protection against the ulcerogenic and other gastric difficulties associated with the use of various non-steroidal anti-inflammatory agents (e.g., indomethacin, aspirin, and phenylbutazone), and bronchodilators. Members of the 16-aryloxy-17-20-tetranor and 17-aryl-18,-20 triner series are expected to have utility as abortifacients, agents for the induction of labor, agents for the induction of menses, fertility-controlling agents, oestrus regulators for use in animal husbandry with cattle and other domestic animals. They also are useful as inhibitors of platelet aggregation and as agents to contain ischemia during myocardial infarction. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, PGFα, PGF, PGA and PGD compounds are all potent in causing multiple biological responses even at low doses. For example, $PGE_1$, $PGE_2$, $PGA_1$ and $PGA_2$ are extremely potent in causing vasodepression and smooth muscle stimulation, and also are potent as antipolytic agents. Moreover, for many applications, these known prostaglandins have an inconveniently short duration of biological activity. In striking contrast, the prostacyclin analogs of this invention are substantially more specific with regard to potency in causing prostaglandin-like biological responses, and/or having a substantially longer duration of biological activity. For example, the 11-deoxy-prostacyclin compounds of this invention are selective in that they are at most relatively weak stimulents of smooth muscle. A further advantage of these novel compounds lies in their increased stabilities and lengthened shelf-lives.

Each of these novel prostacyclin analogs of this invention is surprisingly and unexpectedly more useful than one of the corresponding known prostaglandins and prostacyclins for at least one of the pharmacological purposes indicated below, either because it has a different and narrower spectrum of biological activity than the known prostaglandins and therefore is more specific in its activity and causes smaller and fewer undesired side effects than the known prostaglandins, or because of its prolonged activity, fewer and smaller doses of the novel prostacyclin analog can frequently be used to attain the desired result. They also possess greater chemical stability than the natural prostacyclin, $PGI_2$.

Another advantage of the novel compounds of this invention compared with the known prostaglandins and prostacyclins, is that these novel compounds are administered effectively orally, topically, sublingually, intravaginally, bucally, or rectally, in addition to the usual intravenous, intramuscular, aerosol, or subcutaneous injection or infusion methods indicated for the uses of the known prostaglandins. Of particular interest is the topical vasodilator activity of the 16-hydroxy-16-vinyl derivatives of this invention. These These qualities are advantageous because they facilitate maintaining uniform levels of these compounds in the body with fewer, shorter, or smaller doses, and make possible self-administration by the patient.

The novel prostacyclin of this invention are useful as bronchodilators for the treatment of asthma and chronic bronchitis. As such they may be conveniently administered by inhalation of aerosol sprays prepared in a dose range of about 10 ug to about 10 mg/ml of a pharmacologically suitable liquid vehicle. The prostacyclin compounds are also useful in mammals, including man and certain useful animals, e.g., dogs and pigs to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, on intramuscularly in an infusion dose range of about 0.1 mg to about 500 mg per Kg of body weight per minute, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The prostacyclin compounds of this invention are also useful as topical vasodilators. The prostacycline compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

As noted earlier, the compounds of Formula I may possess a chiral center. Accordingly, the compounds of this invention may be prepared in either their optically active form or as a racemic mixture. Unless otherwise specified, the compounds described herein are all in their racemic form. However, the scope of the subject invention is not to be considered limited to the racemic form, but to encompass the individual optical isomers of the compounds of the present invention.

When desired, the individual diastereomeric and optically isomeric compounds can be isolated by conventional separation and purification procedures in the case of diastereo isomers and by conventional resolution procedures in the case of optical isomers. Optima physical, or physical chemical, separation procedures and resolution procedures can be obtained, by routine trial and error procedures well within the scope of those skilled in the art.

A further understanding of the invention can be had from the following non-limiting preparations and examples. As used hereinabove and below, unless expressly stated to the contrary, all temperatures and temperature ranges referred to the centigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that preparation or example, in terms of moles of finite weight or volume. As noted earlier, compounds having asymmetric centers and optical activity are isolated in their racemic form (+) unless otherwise indicated.

EXAMPLE 1

I. Preparative procedure using a vinyl tin reaction product (a)

2-[8-Trimethylsilyloxy-7-(ethylenedioxy)-2-cis-octenyl]-4-trimethylsilyloxycyclopent-2-en-1-one To a stirred solution of 2.5 g. of 2-[8-hydroxy-7-(ethylenedioxy)-2-cis-octenyl]-4-hydroxycyclopent-2-en-1-one, 21 ml. of pyridine and 7 ml. of hexamethyldisilazane, cooled in an ice-water bath, is added dropwise via a syringe 3.5 ml. of chlorotrimethylsilane. The mixture is stirred at room temperature overnight, diluted with toluene and evaporated to dryness. The residue is treated with toluene and again evaporated to dryness. This residue is treated with hexane, filtered through diatomaceous earth and concentrated in vacuo giving 3.5 g. of the desired product as a yellow liquid. The residue is treated with toluene and evaporated to dryness. This residue is applied to 15 g. of silica gel and washed with 200 ml. of hexane followed by 200 ml. of ethyl acetate. The ethyl acetate extract is evaporated to a residue which is purified by dry column (2"×60") chromatography on 720 g. of silica gel, eluting with ethyl acetate. The solvent is evaporated in vacuo giving 510 mg. of the desired product.

(b) dl-11α,16-Dihydroxy-1-(ethylenedioxy)-1-hydroxymethyl-9-oxo-16-vinyl-5-cis, 13-trans-prostadiene To a stirred solution of 3.36 g. of E-1-tributylstannyl-3-trimethylsilyloxy-4-vinyl-1-octene in 3 ml. of tetrahydrofuran, cooled in a dry ice-acetone bath, is added 2.9 ml. of 2.5 M n-butyllithium in hexane during 20 minutes. The mixture is stirred at −70° C. for 15 minutes, then at −50° to −40° C. for one hour and finally at −40° to −30° C. for 30 minutes. The mixture is cooled to −78° C. and a solution of 0.93 g. of cooperpentyne in 2.4 ml. of hexamethyl phosphortriamide and 8 ml. of ether is added during 15 minutes. This mixture is stirred at −78° C. for 1.5 hours. A solution of 1.32 g. of 2-[8-trimethylsilyloxy-7-(ethylenedioxy)-2-cis-octenyl]-4-trimethylsilyloxycyclopent-2-en-1-one in 5 ml. of ether is added during 15 minutes. This mixture is stirred at −78° C. for 15 minutes, then at −50° to −40° C. for one hour and finally at −40° to −30° C. for 30 minutes. The mixture is recooled to −78° C. and quenched by pouring into a cold mixture of 200 ml. of saturated ammonium chloride solution, 100 ml. of ether and 3 ml. of acetic acid. After stirring vigorously for 20 minutes, the aqueous layer is separated and extracted with two 100 ml. portions of ethyl acetate. The organic extracts are combined, washed with dilute hydrochloric acid, water, then brine and evaporated to dryness. The residue is treated with 20 ml. of acetic acid, 10 ml. of tetrahydrofuran and 5 ml. of water and stirred at room temperature for 40 minutes. This mixture is diluted with toluene and evaporated to dryness.

By substituting E-1-iodo-3,4-isopropylidine-1-octene for the above tributylstannyl compound, using identical reaction, the identical product, product b, is also isolated.

(c) dl-9α,11α,16-Trihydroxy-1-(ethylenedioxy)-1-hydroxymethyl-16-vinyl-5-cis, 13-trans-prostadiene To a stirred solution of 410 mg. of dl-11α,16-dihydroxy-1-(ethylenedioxy)-1-hydroxymethyl-9-oxo-16-vinyl-5-cis, 13-trans-prostadiene in 15 ml. of tetrahydrofuran, cooled in a dry ice-acetone bath, is added 6.5 ml. of 1 M lithium selectride in tetrahydrofuran, dropwise during 15 minutes. The mixture is stirred in the same bath for one hour, then 3.7 ml. of 2.5 N sodium hydroxide is added dropwise through a dropping funnel. The mixture is allowed to warm to 0° C., gradually during 20 minutes. The mixture is then cooled in an ice-water bath and 3 ml. of 30% hydrogen peroxide is cautiously (very exothermic) added dropwise. The mixture is stirred in the ice-water bath for 20 minutes, then diluted with water and concentrated to remove the tetrahydrofuran. The concentrate is diluted with ethyl acetate. The aqueous phase is separated and extracted with ethyl acetate. The ethyl acetate layers are combined, washed with partially saturated sodium chloride solution, then saturated sodium chloride solution and dried. The solvent is evaporated in vacuo to dryness giving 400 mg. of the desired product.

(d) 1-(Ethylenedioxy)-11α,16-dihydroxy-6,9α(epoxy)-1-hydroxymethyl-16-vinyl-5-iodo-13-trans-prostene To a stirred mixture of 190 mg. of dl-9α,11α,16-trihydroxy-1-(ethylenedioxy)-1-hydroxymethyl-16-vinyl-5-cis, 13-trans-prostadiene and 10 ml. of saturated sodium bicarbonate in 10 ml. of ether, cooled in an ice-water bath, is addded a solution of 255 mg. of iodine in 15 ml. of ether, very slowly during 1.5 hours. The mixture is stirred in the bath for 30 minutes and then at room temperature for 2 hours. The mixture is diluted with ether, poured into 5% sodium thiosulfate solution and extracted with ethyl acetate. The combined ether-ethyl acetate extract is washed with water and brine and the solvent is evaporated in vacuo to an oily residue. This residue is purified by preparative thin layer chromatography (1×200μ silica gel), developing with pure ethyl acetate. The product band is washed with ethyl acetate followed by 20% methanol in chloroform giving a total of 200 mg. of the desired product.

(e) 1-(Ethylenedioxa-1-hydroxymethyl-6,9α-epoxy-11α,16-vinyl-13-trans-prostene The mixture of 150 mg of 1-ethylenedioxa-1-hydroxymethyl-5-iodo-6,9α-epoxy-11α,16-dihydroxy-16-vinyl-13-trans-prostene in 0.5 ml of ether and 0.25 ml of toluene, 1.5 mg of azobisisobutyronitrile and 0.15 ml of tributyltin hydride was heated and stirred under an inert atmosphere at 50° C. for 1 hr. After concentration in vacuo, the residue was applied to 2.5 g of silica gel (SilicAR CC-7) and washed with 30 ml of hexane followed by 10 ml of ether, then 30 ml of 20% MeOH in CHCl$_3$. The MeOH/CHCl$_3$ solution was evaporated to give 150 mg of product which was further purified by silica gel prep. tlc developing with ethyl acetate to give 130 mg of pure product; IR $\nu$ 3400 (OH), 1064, 1000 (HC=CH$_2$), 975 (trans C=C), 920 (HC=CH$_2$); MS m/e 420 (M-H$_2$O, calcd for C$_{25}$H$_{40}$O$_5$: 420,2875, Found: 420.2865), 407 (M—CH$_2$OH), 420, 389, 381, 363, 345, 326, 308, 277, 113.

(f) 1-Oxo-1-hydroxymethyl-6,9α-epoxy-11α,16-dihydroxy-16-vinyl-13-trans-prostene The mixture of 85 mg of 1-ethylenedioxa-1-hydroxymethyl-6,9α-epoxy-11α,16-dihydroxy-16-vinyl-13-trans-prostene, 4 ml of acetic acid, 2 ml of THF, 1 ml of water and one drop of 4 NHCl was heated and stirred at 50° C. for 3 hr. Work up by concentration, dilution with ethyl acetate and washing with satd. NaHCO$_3$, water and brine to give 70 mg of oily residue which was purified by silica gel prep. tlc developing with 1% acetic acid in ethyl acetate to give 50 mg of product; IR $\nu$ 3400 (OH), 1724 (C=O), 1000 (HC=CH$_2$), 975 (trans C=C), 920 (HC=CH$_2$); MS m/e 376 (M—H$_2$O, calcd for C$_{23}$H$_{36}$O$_4$: 376.2613, Found: 376.2608), 363 (M—CH$_2$OH), 358, 345, 337, 327, 319, 282, 264, 246, 113.

(g)
4-Hydroxy-2-[7'-ethylenedioxa-8'-hydroxy-2'-Z-octenyl]-cyclopent-2-ene-1-one A mixture of 3.9 g of 4-hydroxy-2-[7'-oxo-8'-hydroxy-2'-Z-octenyl]-cyclopent-2-ene-1-one, 33 ml of ethylene glycol and 2.0 g of Amberlyst-15 (Rohm & Hass Company) was stirred vigorously for 10 hr. The mixture was diluted with ethyl acetate and filtered. The ethylacetate solution was diluted with toluene and washed with water and brine. The aqueous phase was extracted with ethyl acetate and this procedure was repeated several times until the ethyl acetate extract contained no product. The combined organic extract was dried over anhy. $Na_2SO_4$ and concentrated in vacuo to give 4.3 g of product as a colorless oil; PMR $\delta$ 7.16 (m, C-3H), 5.50 (m, olefin), 4.95 (m, C-4H), 4.00 (s, ketal), 3.52 (s, C$\underline{H}_2$OH).

(h)
1-Oxo-1-hydroxymethyl-5-iodo-6,9α-epoxy-11α,16-dihydroxy-16-vinyl-13-trans-prostene To a 0° C., stirred mixture of 135 mg of 1-oxo-1-hydroxymethyl-9α,11α,16-trihydroxy-16-vinyl-5-cis-13-trans-prostadiene, 6.75 ml of ether, 0.9 ml of methylene chloride, and 6.75 ml of saturated sodium bicarbonate was added a solution of 170 mg of iodine in 9 ml of ether during 1.5 hour. After stirring at 5° C. for 2 hours, then at room temperature overnight, the mixture was diluted with ether and poured into 5% sodium thiosulfate solution. The organic extract was separated and washed with water and brine, and dried. After solvent evaporation to dryness, the residue was purified by silica gel prep. tlc plate developing with ethyl acetate to give 110 mg of pure product.

(i)
5-Iodo-6,9α-epoxy-11,16-dihydroxy-16-vinyl-13-trans-prostene methyl ester To a stirred, 0° C. mixture of 120 mg of 9α,11α,16-vinyl-PGF$_{2α}$ methyl ester in 4.5 ml of ether and 4.5 ml of saturated sodium bicarbonate was added a solution of 109 mg of iodine in 6.0 ml of ether very slowly during 1 hour. After stirring at 5° C. for 2 hour, then at room temperature, the mixture was diluted with ether and poured into 5% sodium thiosulfate solution. The organic extract was separated and washed with water and brine and dried. After solvent evaporation to dryness, the residue was purified by silica gel preparative tlc developing with 60% ethyl acetate, 0.5% acetic acid in hexane to give 140 mg of pure product.

(j)
6,9α-Epoxy-11α,16-dihydroxy-16-vinyl-13-trans-prostene methyl ester

The mixture of 105 mg of 5-iodo-6,9α-epoxy-11α,16-dihydroxy-16-vinyl-13-trans-prostene methyl ester in 0.1 ml of toluene and 0.2 ml of ether, 1 mg of azobisisobutyronitrile, and 0.1 ml of tributyltin hydride was heated and stirred under an inert atmosphere at 50° C. for 1 hour. After concentration in vacuo, the residue was applied to 2.5 g of silica gel (SilicAR CC-7) and washed with 35 ml of hexane followed by 50 ml of ethyl acetate. The ethyl acetate solution was evaporated to give 95 mg of product which was further purified by silica gel preparative tlc developing with 70% ethyl acetate, 1% acetic acid in hexane to give 65 mg of pure product.

(k)
6,9α-Epoxy-11α,16-dihydroxy-16-vinyl-13-trans-prostene

To a stirred solution of 530 mg of 6,9α-epoxy-11α,16-vinyl-13-trans-prostene methyl ester in 7 ml of methanol was added 8.5 ml of 1 N NaOH. After stirring at room temperature for 1 hour, the mixture was concentrated in vacuo, diluted with water, acidified with 4 N HCl and extracted with ethyl acetate. The combined organic extract was washed with water and brine and dried over anhydrous sodium sulfate. Solvent evaporation in vacuo to dryness furnished 485 mg of pure product.

It is understood that the 5-iodo analogs which are intermediates for the preparation of the PGI analogs listed herein below and which also have useful biological properties are also claimed in this invention.

By the method described in the previous Example 1, Examples 2–435 illustrate the reaction of the vinyl iodide or vinyl tin compounds with cyclopentene compounds to form the prostaglandin of the PGI$_1$ series.

| EXAMPLE | VINYL IODIDE | CYCLOPENTENONE | PRODUCT PROSTAGLANDIN OF THE PGI1 SERIES |
|---|---|---|---|
| 2 | 1-trans-iodo-3-methyl-3-trimethylsilyloxy-1-heptene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-15-methyl-20-nor-2-nor-13-trans prostene |
| 3 | 1-trans-iodo-4,4-dimethyl-3-trimethylsilyloxy-1-heptene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16,16-dimethyl-20-nor-2-nor-13-trans prostene |
| 4 | 1-trans-iodo-5,5-dimethyl-3-trimethylsilyloxy-1-heptene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-17,17-dimethyl-2-nor-13-trans prostene |
| 5 | 1-trans-iodo-4-methyl-3-triphenylmethoxy-1-octene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-methyl-2-nor-13-trans prostene |
| 6 | 1-trans-iodo-4,4-trimethyl-3-trimethylsilyloxy-1-octene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16,16-trimethylene-20-nor-2-nor-13-trans prostene |

| EXAMPLE | VINYL TIN | CYCLOPENTENONE | PRODUCT PROSTAGLANDIN OF THE PGI1 SERIES |
|---|---|---|---|
| 7 | 1-trans-tri-n-butylstannyl-3-vinyl-3-trimethylsilyloxy-1-heptene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-15-vinyl-20-nor-2-nor-13-trans prostene |
| 8 | 1-trans-tri-n-butylstannyl-4-phenoxy-3-triethylsilyloxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-phenoxy-17-phenyl-2-nor-18-20-tetranor-13-trans prostene |
| 9 | 1-trans-tri-n-butylstannyl-4-(p-fluorophenoxy)-3-triethylsilyloxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-(p-fluorophenoxy)-2-nor-17-20-tetranor-13-trans prostene |
| 10 | 1-trans-tri-n-butylstannyl-4-(m-chlorophenoxy)-3-triethylsilyloxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-(m-chlorophenoxy)-2-nor-17-20-tetranor-13-trans prostene |
| 11 | 1-trans-tri-n-butylstannyl-4-(m-trifluoromethylphenoxy)-3-triethylsilyloxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE PGI1 SERIES |
|---|---|---|---|
| 12 | 1-trans-iodo-5-phenyl-3-triethylsilyloxy-1-pentene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-15-17-phenyl-2-nor-18-20-trinor-13-trans prostene |
| 13 | 1-trans-iodo-4,4-dimethyl-5-phenyl-3-triethylsilyloxy-1-pentene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16,16-dimethyl-17-phenyl-2-nor-18-20-trinor-13-trans prostene |
| 14 | 1-trans-iodo-4-cyclopentyl-3-triethylsilyloxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-cyclopentyl-2-nor-17-20-tetranor-13-trans prostene |
| 15 | 1-trans-iodo-4-cyclohexyl-3-triphenylmethoxy-1-butene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-16-cyclohexyl-2-nor-17-20-tetranor-13-trans prostene |
| 33 | 1-trans-iodo-3-triphenylmethoxy-1-octene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-2-nor-13-trans prostene |
| 34 | 1-trans-iodo-3-methyl-3-trimethylsilyloxy-1-octene | 2-[5-(2-(trimethylsilyloxymethyl)-1,3-dioxolan-2-yl)pent-2-cis-enyl]-4-trimethylsiloxy cyclopent-2-en-1-one | dl-11α,15α-dihydroxy-1-hydroxymethyl-1-oxo-6,9α-epoxy-15-methyl-2-nor-13-trans prostene |

| EXAMPLE | VINYL IODIDE / VINYL TIN | CYCLOPENTENONE | PRODUCT PROSTAGLANDIN |
|---|---|---|---|
| 35 | 1-trans-iodo-4,4-dimethyl-3-trimethylsilyloxy-1-octene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-dimethyl-2-nor-13-trans prostene |
| 36 | 1-trans-iodo-4,4-trimethylene-3-trimethylsilyloxy-1-octene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-trimethylene-2-nor-13-trans prostene |
| EXAMPLE | VINYL TIN | CYCLOPENTENONE | PRODUCT PROSTAGLANDIN OF THE PGI1 SERIES |
| 37 | 1-trans-tri-n-butylstannyl-3-vinyl-3-trimethylsilyloxy-1-octene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-15-vinyl-2-nor-13-trans prostene |
| EXAMPLE | VINYL IODIDE | CYCLOPENTENONE | PRODUCT PROSTAGLANDIN OF THE PGI1 SERIES |
| 51 | 1-trans-iodo-3-triphenylmethoxy-1-nonene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-20-methyl-2-nor-13-trans prostene |
| 52 | 1-trans-iodo-3-methyl-3-trimethylsilyloxy-1-nonene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-15-methyl-20-methyl-2-nor-13-trans prostene |
| 53 | 1-trans-iodo-4,4-dimethyl-3-trimethylsilyloxy-1-nonene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-dimethyl-20-methyl-2-nor-13-trans prostene |
| 54 | 1-trans-iodo-4,4-trimethylene-3-trimethylsilyloxy-1-nonene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-trimethylene-20-methyl-2-nor-13-trans prostene |
| EXAMPLE | VINYL TIN | CYCLOPENTENONE | PRODUCT PROSTAGLANDIN OF THE PGI1 SERIES |
| 55 | 1-trans-tri-n-butylstannyl-3-vinyl-3-trimethylsilyloxy-1-nonene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-15-vinyl-20-methyl-2-nor-13-trans prostene |
| EXAMPLE | VINYL IODIDE | CYCLOPENTENONE | PRODUCT PROSTAGLANDIN OF THE PGI1 SERIES |
| 69 | 1-trans-iodo-3-triphenylmethoxy-1-decene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-20-ethyl-2-nor-13-trans prostene |
| 70 | 1-trans-iodo-3-methyl-3-trimethylsilyloxy-1-decene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-15-methyl-20-ethyl-2-nor-13-trans prostene |
| 71 | 1-trans-iodo-4,4-dimethyl-3-trimethylsilyloxy-1-decene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-dimethyl-20-ethyl-2-nor-13-trans prostene |
| 72 | 1-trans-iodo-4,4-trimethylene-3-trimethylsilyloxy-1-decene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-16,16-trimethylene-20-ethyl-2-nor-13-trans prostene |
| EXAMPLE | VINYL TIN | CYCLOPENTENONE | PRODUCT PROSTAGLANDIN OF THE PGI1 SERIES |
| 73 | 1-trans-tri-n-butylstannyl-3-vinyl-3-trimethylsilyloxy-1-decene | 2-[5(-2-(trimethylsilyloxymethyl)-1,3-dioxolan-2-yl)pent-2-cis-enyl]-4-trimethylsilyloxy-cyclopent-2-en-1-one | dl-11α,15α-dihydroxy-1-hydroxymethyl-1-oxo-6,9α-epoxy-15-vinyl-20-ethyl-2-nor-13-trans prostene |
| EXAMPLE | VINYL IODIDE | CYCLOPENTENONE | PRODUCT PROSTAGLANDIN OF THE PGI1 SERIES |
| 87 | 1-trans-iodo-3-triphenylmethoxy-1-heptene | 2-[6(-2-(trimethylsilyloxymethyl)-1,3-dioxolan-2-yl)hex-2-cis-enyl]-4-trimethylsilyloxy | dl-11α,15α-dihydroxy-1-hydroxymethyl-1-oxo-6,9α-epoxy-20-nor-13-trans prostene |

| EXAMPLE | VINYL TIN | CYCLOPENTENONE | PRODUCT PROSTAGLANDIN OF THE PGI1 SERIES |
|---|---|---|---|
| 88 | 1-trans-iodo-3-methyl-3-trimethylsilyloxy-1-heptene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-15-methyl-20-nor-13-trans prostene |
| 89 | 1-trans-iodo-4,4-dimethyl-3-trimethylsilyloxy-1-heptene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16,16-dimethyl-20-nor-13-trans prostene |
| 90 | 1-trans-iodo-5,5-dimethyl-3-triphenylmethoxy-1-octene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-17,17-dimethyl-13-trans prostene |
| 91 | 1-trans-iodo-4-methyl-3-triphenylmethoxy-1-octene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-methyl-13-trans prostene |
| 92 | 1-trans-iodo-4,4-trimethylene-3-trimethylsilyloxy-1-heptene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16,16-trimethylene-20-nor-13-trans prostene |

| EXAMPLE | VINYL TIN | CYCLOPENTENONE | PRODUCT PROSTAGLANDIN OF THE PGI1 SERIES |
|---|---|---|---|
| 93 | 1-trans-tri-n-butylstannyl-3-vinyl-3-trimethylsilyloxy-1-heptene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-15-vinyl-20-nor-13-trans prostene |
| 94 | 1-trans-tri-n-butylstannyl-4-phenoxy-3-trimethylsilyloxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-phenoxy-17-20-tetranor-13-trans prostene |
| 95 | 1-trans-tri-n-butylstannyl-4-(p-fluorophenoxy-3-triethylsilyloxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-p-fluorophenoxy)-17-20-tetranor-13-trans prostene |
| 96 | 1-trans-tri-n-butylstannyl-4-(m-chlorophenoxy)-3-triethylsilyloxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-m-chlorophenoxy)-17-20-tetranor-13-trans prostene |
| 97 | 1-trans-tri-n-butylstannyl-4-(m-trifluoromethylphenoxy)-3-trimethylsilyloxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGI1 SERIES |
|---|---|---|---|
| 98 | 1-trans-iodo-5-phenyl-3-triethylsilyloxy-1-pentene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-17-phenyl-18-20-trinor-13-trans prostene |
| 99 | 1-trans-iodo-4,4-dimethyl-5-phenyl-3-triethylsilyloxy-1-pentene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16,16-dimethyl-17-phenyl-18-20-trinor-13-trans prostene |
| 100 | 1-trans-iodo-4-cyclopentyl-3-triphenylmethoxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-cyclopentyl-17-20-tetranor-13-trans prostene |
| 101 | 1-trans-iodo-4-cyclohexyl-3-triphenylmethoxy-1-butene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-16-cyclohexyl-17-20-tetranor-13-trans prostene |
| 119 | 1-trans-iodo-3-triphenylsilyloxy-1-octene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-13-trans prostene |
| 120 | 1-trans-iodo-3-methyl-3-trimethylsilyloxy-1-octene | 2-[6(-2-(trimethylsiloxymethyl)-1,3-dioxolan-2-yl)hex-2-cis-enyl]-4-trimethylsilyloxy cyclopent-2-en-1-one | dl-11α,15α-dihydroxy-1-hydroxymethyl-1-oxo-6,9α-epoxy-15-methyl-13-trans prostene |

| | | -continued | |
|---|---|---|---|
| 121 | 1-trans-iodo-4,4-dimethyl-3-trimethylsilyloxy-1-octene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-dimethyl-13-trans prostene |
| 122 | 1-trans-iodo-4,4-trimethylene-3-trimethylsilyloxy-1-octene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-trimethylene-13-trans prostene |
| EXAMPLE | VINYL TIN | CYCLOPENTENONE | PRODUCT PROSTAGLANDIN OF THE PGI1 SERIES |
| 123 | 1-trans-tri-n-butylstannyl-3-vinyl-3-trimethylsilyloxy-1-octene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-15-vinyl-13-trans prostene |
| EXAMPLE | VINYL IODIDE | CYCLOPENTENONE | PRODUCT PROSTAGLANDIN OF THE PGI1 SERIES |
| 137 | 1-trans-iodo-3-triphenylmethoxy-1-nonene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-20-methyl-13-trans prostene |
| 138 | 1-trans-iodo-3-methyl-3-trimethylsilyloxy-1-nonene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-15-methyl-20-methyl-13-trans prostene |
| 139 | 1-trans-iodo-4,4-dimethyl-3-trimethylsilyloxy-1-nonene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-dimethyl-20-methyl-13-trans prostene |
| 140 | 1-trans-iodo-4,4-trimethylene-3-trimethylsilyloxy-1-nonene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-trimethylene-20-methyl-13-trans prostene |
| EXAMPLE | VINYL TIN | CYCLOPENTENONE | PRODUCT PROSTAGLANDIN OF THE PGI1 SERIES |
| 141 | 1-trans-tri-n-butylstannyl-3-vinyl-3-trimethylsilyloxy-1-nonene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-15-vinyl-20-methyl-13-trans prostene |
| EXAMPLE | VINYL IODIDE | CYCLOPENTENONE | PRODUCT PROSTAGLANDIN OF THE PGI1 SERIES |
| 155 | 1-trans-iodo-3-triphenylmethoxy-1-decene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-20-ethyl-13-trans prostene |
| 156 | 1-trans-iodo-3-methyl-3-trimethylsilyloxy-1-decene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-15-methyl-20-ethyl-13-trans prostene |
| 157 | 1-trans-iodo-4,4-dimethyl-3-trimethylsilyloxy-1-decene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-dimethyl-20-ethyl-13-trans prostene |
| 158 | 1-trans-iodo-4,4-trimethylene-3-trimethylsilyloxy-1-decene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-16,16-trimethylene-20-ethyl-13-trans prostene |
| EXAMPLE | VINYL TIN | CYCLOPENTENONE | PRODUCT PROSTAGLANDIN OF THE PGI1 SERIES |
| 159 | 1-trans-tri-n-butylstannyl-3-vinyl-3-trimethylsilyloxy-1-decene | 2-[6(-2-(trimethylsiloxymethyl)-1,3-dioxolan-2-yl)hex-2-cis-enyl]-4-trimethylsiloxy cyclopent-2-en-1-one | dl-11α,15α-dihydroxy-1-hydroxymethyl-1-oxo-6,9α-epoxy-15-vinyl-20-ethyl-13-trans prostene |
| EXAMPLE | VINYL IODIDE | CYCLOPENTENONE | PRODUCT PROSTAGLANDIN OF THE PGI1 SERIES |
| 173 | 1-trans-iodo-3-triphenylmethoxy-1-heptene | 2-[7(-2-(trimethylsiloxymethyl)-1,3-dioxolan-2-yl)hept-2-cis-enyl]-4-trimethylsiloxy | dl-11α,15α-dihydroxy-1-hydroxymethyl-1-oxo-6,9α-epoxy-20-nor-2-homo-13-trans prostene |

| Example | Vinyl tin / Vinyl iodide | Cyclopentenone | Product prostaglandin of the PGI1 series / PGI2 series |
|---|---|---|---|
| 174 | 1-trans-iodo-3-methyl-3-trimethylsilyloxy-1-heptene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-20-nor-2-homo-13-trans prostene-15-methyl- |
| 175 | 1-trans-iodo-4,4-dimethyl-3-trimethylsilyloxy-1-heptene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16,16-dimethyl-20-nor-2-homo-13-trans prostene |
| 176 | 1-trans-iodo-5,5-dimethyl-3-triphenylmethoxy-1-octene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-17,17-dimethyl-2-homo-13-trans prostene |
| 177 | 1-trans-iodo-4-methyl-3-triphenylmethoxy-1-octene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-methyl-2-homo-13-trans prostene |
| 178 | 1-trans-iodo-4,4-trimethylene-3-trimethylsilyloxy-1-heptene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16,16-trimethylene-20-nor-2-homo-13-trans prostene |
| EXAMPLE | VINYL TIN | CYCLOPENTENONE | PRODUCT PROSTAGLANDIN OF THE PGI1 SERIES |
| 179 | 1-trans-tri-n-butylstannyl-3-vinyl-3-trimethylsilyloxy-1-heptene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-15-vinyl-20-nor-2-homo-13-trans prostene |
| 180 | 1-trans-tri-n-butylstannyl-4-phenoxy-3-triethylsilyloxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-phenoxy-2-homo-17-20-tetranor-13-trans prostene |
| 181 | 1-trans-tri-n-butylstannyl-4-(p-fluorophenoxy)-3-triethylsilyloxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-(p-fluorophenoxy)-2-homo-17-20-tetranor-13-trans prostene |
| 182 | 1-trans-tri-n-butylstannyl-4-(m-chlorophenoxy)-3-triethylsilyloxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-(m-chlorophenoxy)-2-homo-17-20-tetranor-13-trans prostene |
| 183 | 1-trans-tri-n-butylstannyl-4-(m-trifluoromethylphenoxy)-3-triethylsilyloxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-(m-trifluoromethylphenoxy)-2-homo-17-20-tetranor-13-trans prostene |
| EXAMPLE | VINYL IODIDE | CYCLOPENTENONE | PRODUCT PROSTAGLANDIN OF THE PGI1 SERIES |
| 184 | 1-trans-iodo-5-phenyl-3-triethylsilyloxy-1-pentene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-17-phenyl-2-homo-18-20-trinor-13-trans prostene |
| 185 | 1-trans-iodo-4,4-dimethyl-5-phenyl-3-triethylsilyloxy-1-pentene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16,16-dimethyl-17-phenyl-2-homo-18-20-trinor-13-trans prostene |
| 186 | 1-trans-iodo-4-cyclopentyl-3-triphenylmethoxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-cyclopentyl-2-homo-17-20-tetranor-13-trans prostene |
| 187 | 1-trans-iodo-4-cyclohexyl-3-triphenylmethoxy-1-butene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-16-cyclohexyl-2-homo-17-20-tetranor-13-trans prostene |
| 205 | 1-trans-iodo-3-triphenylmethoxy-1-octene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-2-homo-13-trans prostene |
| 206 | 1-trans-iodo-3-methyl-3-trimethylsilyloxy-1-octene | 2-[7-(2-(trimethylsiloxymethyl)-1,3-dioxolan-2-yl)hept-2-cis-enyl]-4-trimethylsiloxy cyclopent-2-en-1-one | dl-11α,15α-dihydroxy-1-hydroxymethyl-1-oxo-6,9α-epoxy-15-methyl-2-homo-13-trans prostene |

| | | | |
|---|---|---|---|
| 207 | 1-trans-iodo-4,4-dimethyl-3-trimethylsilyloxy-1-octene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-dimethyl-2-homo-13-trans prostene |
| 208 | 1-trans-iodo-4,4-trimethylene-3-trimethylsilyloxy-1-octene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-trimethylene-2-homo-13-trans prostene |
| EXAMPLE | VINYL TIN | CYCLOPENTENONE | PRODUCT PROSTAGLANDIN OF THE PGII SERIES |
| 209 | 1-trans-tri-n-butylstannyl-3-vinyl-3-trimethylsilyloxy-1-octene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-15-vinyl-2-homo-13-trans prostene |
| EXAMPLE | VINYL IODIDE | CYCLOPENTENONE | PRODUCT PROSTAGLANDIN OF THE PGII SERIES |
| 223 | 1-trans-iodo-3-triphenylmethoxy-1-nonene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-20-methyl-2-homo-13-trans prostene |
| 224 | 1-trans-iodo-3-methyl-3-trimethylsilyloxy-1-nonene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-15-methyl-20-methyl-2-homo-13-trans prostene |
| 225 | 1-trans-iodo-4,4-dimethyl-3-trimethylsilyloxy-1-nonene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-dimethyl-20-methyl-2-homo-13-trans prostene |
| 226 | 1-trans-iodo-4,4-trimethylene-3-trimethylsilyloxy-1-nonene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-trimethylene-20-methyl-2-homo-13-trans prostene |
| EXAMPLE | VINYL TIN | CYCLOPENTENONE | PRODUCT PROSTAGLANDIN OF THE PGII SERIES |
| 227 | 1-trans-tri-n-butylstannyl-3-vinyl-3-trimethylsilyloxy-1-nonene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-15-vinyl-20-methyl-2-homo-13-trans prostene |
| EXAMPLE | VINYL IODIDE | CYCLOPENTENONE | PRODUCT PROSTAGLANDIN OF THE PGII SERIES |
| 241 | 1-trans-iodo-3-triphenylmethoxy-1-decene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-20-ethyl-2-homo-13-trans prostene |
| 242 | 1-trans-iodo-3-methyl-3-trimethylsilyloxy-1-decene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-15-methyl-20-ethyl-2-homo-13-trans prostene |
| 243 | 1-trans-iodo-4,4-dimethyl-3-trimethylsilyloxy-1-decene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-dimethyl-20-ethyl-2-homo-13-trans prostene |
| 244 | 1-trans-iodo-4,4-trimethylene-3-trimethylsilyloxy-1-decene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-16,16-trimethylene-20-ethyl-2-homo-13-trans prostene |
| EXAMPLE | VINYL TIN | CYCLOPENTENONE | PRODUCT PROSTAGLANDIN OF THE PGII SERIES |
| 245 | 1-trans-tri-n-butylstannyl-3-vinyl-3-trimethylsilyloxy-1-decene | 2-[7-(2-(trimethylsiloxymethyl)-1,3-dioxolan-2-yl)hept-2-cis-enyl]-4-trimethylsilyloxy cyclopent-2-en-1-one | dl-11α,15α-dihydroxy-1-hydroxymethyl-1-oxo-6,9α-epoxy-15-vinyl-20-ethyl-2-homo-13-trans prostene |
| EXAMPLE | VINYL IODIDE | CYCLOPENTENONE | PRODUCT PROSTAGLANDIN OF THE PGII SERIES |
| 259 | 1-trans-iodo-3-triphenylmethoxy-1-heptene | 2-[6-(2-(trimethylsiloxymethyl)-1,3-dioxolan-2-yl)hex-2-cis-enyl]-4R-trimethylsilyloxy | nat-11α,15α-dihydroxy-1-hydroxymethyl-1-oxo-6,9α-epoxy-20-nor-13-trans prostene |

| Example | | | |
|---|---|---|---|
| 260 | 1-trans-iodo-3-methyl-3-trimethylsilyloxy-1-heptene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-methyl-20-nor-13-trans prostene |
| 261 | 1-trans-iodo-4,4-dimethyl-3-trimethylsilyloxy-1-heptene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-dimethyl-20-nor-13-trans prostene |
| 262 | 1-trans-iodo-5,5-dimethyl-3-triphenylmethoxy-1-octene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-17,17-dimethyl-13-trans prostene |
| 263 | 1-trans-iodo-4-methyl-3-triphenylmethoxy-1-octene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-methyl-13-trans prostene |
| 264 | 1-trans-iodo-4,4-trimethylene-3-trimethylsilyloxy-1-heptene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-trimethylene-20-nor-13-trans prostene |

| EXAMPLE | VINYL TIN | CYCLOPENTENONE | PRODUCT PROSTAGLANDIN OF THE PGI1 SERIES |
|---|---|---|---|
| 265 | 1-trans-tri-n-butylstannyl-3-vinyl-3-trimethylsilyloxy-1-heptene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-vinyl-20-nor-13-trans prostene |
| 266 | 1-trans-tri-n-butylstannyl-4-phenoxy 3-triethylsilyloxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-phenoxy-17-20-tetranor-13-trans prostene |
| 267 | 1-trans-tri-n-butylstannyl-4-(p-fluorophenoxy) 3-triethylsilyloxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-(p-fluorophenoxy)-17-20-tetranor-13-trans prostene |
| 268 | 1-trans-tri-n-butylstannyl-4-(m-chlorophenoxy) 3-triethylsilyloxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-(m-chlorophenoxy)-17-20-tetranor-13-trans prostene |
| 269 | 1-trans-tri-n-butylstannyl-4-(m-trifluoromethylphenoxy) 3-triethylsilyloxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGI1 SERIES |
|---|---|---|---|
| 270 | 1-trans-iodo-5-phenyl 3-triethylsilyloxy-1-pentene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-17-phenyl-18-20-trinor-13-trans prostene |
| 271 | 1-trans-iodo-4,4-dimethyl-5-phenyl 3-triethylsilyloxy-1-pentene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-dimethyl-17-phenyl-18-20-trinor-13-trans prostene |
| 272 | 1-trans-iodo-4-cyclopentyl 3-triphenylmethoxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-cyclopentyl-17-20-tetranor-13-trans prostene |
| 273 | 1-trans-iodo-4-cyclohexyl 3-triphenylmethoxy-1-butene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16-cyclohexyl-17-20-tetranor-13-trans prostene |
| 291 | 1-trans-iodo-3-triphenylmethoxy-1-octene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-13-trans prostene |
| 292 | 1-trans-iodo-3-methyl-3-trimethylsilyloxy-1-octene | 2-[6(-2-(trimethylsilyloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-methyl-13-trans prostene |

| | | -continued | |
|---|---|---|---|
| 293 | 1-trans-iodo-4,4-dimethyl 3-trimethylsilyloxy-1-octene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-dimethyl-13-trans prostene |
| 294 | 1-trans-iodo-4,4-trimethylene-3-trimethylsilyloxy-1-octene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-trimethylene-13-trans prostene |
| EXAMPLE | VINYL TIN | CYCLOPENTENONE | PRODUCT PROSTAGLANDIN OF THE PGI1 SERIES |
| 295 | 1-trans-tri-n-butylstannyl-3-vinyl-3-trimethylsilyloxy-1-octene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-vinyl-13-trans prostene |
| 331 | 1-trans-tri-n-butylstannyl-3-vinyl-3-trimethylsilyloxy-1-decene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-vinyl-20-ethyl-13-trans prostene |
| EXAMPLE | VINYL IODIDE | CYCLOPENTENONE | PRODUCT PROSTAGLANDIN OF THE PGI1 SERIES |
| 327 | 1-trans-iodo-3-triphenylmethoxy-1-decene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-20-ethyl-13-trans prostene |
| 328 | 1-trans-iodo-3-methyl-3-trimethylsilyloxy-1-decene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-15-methyl-20-ethyl-13-trans prostene |
| 329 | 1-trans-iodo-4,4-dimethyl 3-trimethylsilyloxy-1-decene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-dimethyl-20-ethyl-13-trans prostene |
| 330 | 1-trans-iodo-4,4-trimethylene-3-trimethylsilyloxy-1-decene | 2-[6(-2-(trimethylsiloxymethyl)-1,3-dioxolan-2-yl)hex-2-cis-enyl]-4R-trimethylsiloxy cyclopent-2-en-1-one | nat-11α,15α-dihydroxy-1-hydroxymethyl-1-oxo-6,9α-epoxy-16,16-trimethylene-20-ethyl-13-trans prostene |
| EXAMPLE | VINYL IODIDE | CYCLOPENTENONE | PRODUCT PROSTAGLANDIN OF THE 11-DEOXY PGI1 SERIES |
| 345 | 1-trans-iodo-3-triphenylmethoxy-1-heptene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-20-nor-2-nor-13-trans prostene |
| 346 | 1-trans-iodo-3-methyl-3-trimethylsilyloxy-1-heptene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-15-methyl-20-nor-2-nor-13-trans prostene |
| 347 | 1-trans-iodo-4,4-dimethyl 3-trimethylsilyloxy-1-heptene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16,16-dimethyl-20-nor-2-nor-13-trans prostene |
| 348 | 1-trans-iodo-5,5-dimethyl 3-triphenylmethoxy-1-octene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-17,17-dimethyl-2-nor-13-trans prostene |
| 349 | 1-trans-iodo-4-methyl 3-triphenylmethoxy-1-octene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16-methyl-2-nor-13-trans prostene |
| 350 | 1-trans-iodo-4,4-trimethylene 3-trimethylsilyloxy-1-heptene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16,16-trimethylene-20-nor-2-nor-13-trans prostene |
| EXAMPLE | VINYL TIN | CYCLOPENTENONE | PRODUCT PROSTAGLANDIN OF THE 11-DEOXY PGI1 SERIES |
| 351 | 1-trans-tri-n-butylstannyl-3-vinyl-3-trimethylsilyloxy-1-heptene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-15-vinyl-20-nor-2-nor-13-trans prostene |

| EXAMPLE | VINYL IODIDE | CYCLOPENTENONE | PRODUCT PROSTAGLANDIN OF THE 11-DEOXY PGII SERIES |
|---|---|---|---|
| 352 | 1-trans-tri-n-butylstannyl-4-phenoxy-3-triethylsilyloxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-phenoxy-2-nor-17-20-tetranor-13-trans prostene |
| 353 | 1-trans-tri-n-butylstannyl-4-(p-fluorophenoxy)-3-triethylsilyloxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-(p-fluorophenoxy)-2-nor-17-20-tetranor-13-trans prostene |
| 354 | 1-trans-tri-n-butylstannyl-4-(m-chlorophenoxy)-3-triethylsilyloxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-(m-chlorophenoxy)-2-nor-17-20-tetranor-13-trans prostene |
| 355 | 1-trans-tri-n-butylstannyl-4-(m-trifluoromethylphenoxy)-3-triethylsilyloxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-(m-trifluoromethylphenoxy)-2-nor-17-20-tetranor-13-trans prostene |
| EXAMPLE | VINYL IODIDE | CYCLOPENTENONE | PRODUCT PROSTAGLANDIN OF THE 11-DEOXY PGII SERIES |
| 356 | 1-trans-iodo-5-phenyl-3-triethylsilyloxy-1-pentene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-17-phenyl-2-nor-18-20-trinor-13-trans prostene |
| 357 | 1-trans-iodo-4,4-dimethyl-5-phenyl-3-triethylsilyloxy-1-pentene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16,16-dimethyl-17-phenyl-2-nor-18-20-trinor-13-trans prostene |
| 358 | 1-trans-iodo-4-cyclopentyl-3-triphenylmethoxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-cyclopentyl-2-nor-17-20-tetranor-13-trans prostene |
| 359 | 1-trans-iodo-4-cyclohexyl-3-triphenylmethoxy-1-butene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16-cyclohexyl-2-nor-17-20-tetranor-13-trans prostene |
| 360 | 1-trans-iodo-3-triphenylmethoxy-1-octene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-2-nor-13-trans prostene |
| 361 | 1-trans-iodo-3-methyl-3-trimethylsilyloxy-1-octene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-15-methyl-2-nor-13-trans prostene |
| 362 | 1-trans-iodo-4,4-dimethyl-3-trimethylsilyloxy-1-octene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16,16-dimethyl-2-nor-13-trans prostene |
| 363 | 1-trans-iodo-4,4-trimethylene-3-trimethylsilyloxy-1-octene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16,16-trimethylene-2-nor-13-trans prostene |
| EXAMPLE | VINYL TIN | CYCLOPENTENONE | PRODUCT PROSTAGLANDIN OF THE 11-DEOXY PGII SERIES |
| 364 | 1-trans-tri-n-butylstannyl-3-vinyl-3-trimethylsilyloxy-1-octene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-2-nor-13-trans prostene |
| EXAMPLE | VINYL IODIDE | CYCLOPENTENONE | PRODUCT PROSTAGLANDIN OF THE 11-DEOXY PGII SERIES |
| 365 | 1-trans-iodo-3-triphenylmethoxy-1-nonene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-20-methyl-2-nor-13-trans prostene |
| 366 | 1-trans-iodo-3-methyl-3-trimethylsilyloxy-1-nonene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-15-methyl-20-methyl-2-nor-13-trans prostene |
| 367 | 1-trans-iodo-4,4-dimethyl-3-trimethylsilyloxy-1-nonene | 2-[5(c-2-(trimethylsilyloxymethyl)-1,3-dioxolan-2-yl]pent-2-cis-enyl] cyclopent-2-en-1-one | dl-15α-hydroxy-1-hydroxymethyl-1-oxo-6,9α-epoxy-16,16-dimethyl-20-methyl-2-nor-13-trans prostene |

| | | -continued | |
|---|---|---|---|
| 368 | 1-trans-iodo-4,4-trimethylene-3-trimethylsilyloxy-1-nonene | cyclopent-2-en-1-one 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16,16-trimethylene-20-methyl-2-nor-13-trans prostene |
| EXAMPLE | VINYL TIN | CYCLOPENTENONE | PRODUCT PROSTAGLANDIN OF THE 11-DEOXY PGI1 SERIES |
| 369 | 1-trans-tri-n-butylstannyl-3-vinyl-3-trimethylsilyloxy-1-nonene | 2-[5(-2-((trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-15-vinyl-20-methyl-2-nor-13-trans prostene |
| EXAMPLE | VINYL IODIDE | CYCLOPENTENONE | PRODUCT PROSTAGLANDIN OF THE 11-DEOXY PGI1 SERIES |
| 370 | 1-trans-iodo-3-triphenylmethoxy-1-decene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-20-ethyl-2-nor-13-trans prostene |
| 371 | 1-trans-iodo-3-methyl-3-trimethylsilyloxy-1-decene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-15-methyl-20-ethyl-2-nor-13-trans prostene |
| 372 | 1-trans-iodo-4,4-dimethyl-3-trimethylsilyloxy-1-decene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16,16-dimethyl-20-ethyl-2-nor-13-trans prostene |
| 373 | 1-trans-iodo-4,4-trimethylene-3-trimethylsilyloxy-1-decene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-16,16-trimethylene-20-ethyl-2-nor-13-trans prostene |
| EXAMPLE | VINYL TIN | CYCLOPENTENONE | PRODUCT PROSTAGLANDIN OF THE 11-DEOXY PGI1 SERIES |
| 374 | 1-trans-tri-n-butylstannyl-3-vinyl-3-trimethylsilyloxy-1-decene | 2-[5(-2-(trimethylsiloxymethyl)-1,3-dioxolan-2-yl)pent-2-cis-enyl] cyclopent-2-en-1-one | dl-15α-hydroxy-1-hydroxymethyl-1-oxo-6,9α-epoxy-15-vinyl-20-ethyl-2-nor-13-trans prostene |
| EXAMPLE | VINYL IODIDE | CYCLOPENTENONE | PRODUCT PROSTAGLANDIN OF THE 11-DEOXY PGI1 SERIES |
| 375 | 1-trans-iodo-3-triphenylmethoxy-1-heptene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-20-nor-13-trans prostene |
| 376 | 1-trans-iodo-3-methyl-3-trimethylsilyloxy-1-heptene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-15-methyl-20-nor-13-trans prostene |
| 377 | 1-trans-iodo-4,5-dimethyl-3-trimethylsilyloxy-1-heptene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-16,16-dimethyl-20-nor-13-trans prostene |
| 378 | 1-trans-iodo-5,5-dimethyl-3-triphenylmethoxy-1-octene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-17,17-dimethyl-13-trans prostene |
| 379 | 1-trans-iodo-4-methyl-3-triphenylmethoxy-1-octene | 22-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-16-methyl-13-trans prostene |
| 380 | 1-trans-iodo-4,4-trimethylene-3-trimethylsilyloxy-1-heptene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-16,16-trimethylene-20-nor-13-trans prostene |
| EXAMPLE | VINYL TIN | CYCLOPENTENONE | PRODUCT PROSTAGLANDIN OF THE 11-DEOXY PGI1 SERIES |
| 381 | 1-trans-tri-n-butylstannyl-3-vinyl-3-trimethylsilyloxy-1-heptene | 2-[6(-2-(trimethylsiloxymethyl)-1,3-dioxolan-2-yl)hex-2-cis-enyl] cyclopent-2-en-1-one | dl-15α-hydroxy-1-hydroxymethyl-1-oxo-6,9α-epoxy-15-vinyl-20-nor-13-trans prostene |

| Example | | | -continued | |
|---|---|---|---|---|
| 382 | | 1-trans-tri-n-butylstannyl-4-phenoxy-3-triethylsilyloxy-1-butene | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-phenoxy-17-20-tetranor-13-trans prostene |
| 383 | | 1-trans-tri-n-butylstannyl-4-(p-fluorophenoxy)-3-triethylsilyloxy-1-butene | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-(p-fluorophenoxy)-17-20-tetranor-13-trans prostene |
| 384 | | 1-trans-tri-n-butylstannyl-4-(m-chlorophenoxy)-3-triethylsilyloxy-1-butene | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-(m-chlorophenoxy)-17-20-tetranor-13-trans prostene |
| 385 | | 1-trans-tri-n-butylstannyl-4-(m-trifluoromethylphenoxy)-3-triethylsilyloxy-1-butene | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-(m-trifluoromethylphenoxy)-17-20-tetranor-13-trans prostene |
| EXAMPLE | VINYL IODIDE | | CYCLOPENTENONE | PRODUCT PROSTAGLANDIN OF THE 11-DEOXY PGI1 SERIES |
| 386 | 1-trans-iodo-5-phenyl-3-triethylsilyloxy-1-pentene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-17-phenyl-18-20-trinor-13-trans prostene |
| 387 | 1-trans-iodo-4,4-dimethyl-5-phenyl-3-triethylsilyloxy-1-pentene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-dimethyl-17-phenyl-18-20-trinor-13-trans prostene |
| 388 | 1-trans-iodo-4-cyclopentyl-3-triphenylmethoxy-1-butene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-cyclopentyl-17-20-tetranor-13-trans prostene |
| 389 | 1-trans-iodo-4-cyclohexyl-3-triphenylmethoxy-1-butene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16-cyclohexyl-17-20-tetranor-13-trans prostene |
| 390 | 1-trans-iodo-3-triphenylmethoxy-1-octene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-13-trans prostene |
| 391 | 1-trans-iodo-3-methyl-3-trimethylsilyloxy-1-octene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-methyl-13-trans prostene |
| 392 | 1-trans-iodo-4,4-dimethyl-3-trimethylsilyloxy-1-octene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-dimethyl-13-trans prostene |
| 393 | 1-trans-iodo-4,4-trimethylene-3-trimethylsilyloxy-1-octene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-trimethylene-13-trans prostene |
| EXAMPLE | VINYL TIN | | CYCLOPENTENONE | PRODUCT PROSTAGLANDIN OF THE 11-DEOXY PGI1 SERIES |
| 394 | 1-trans-tri-n-butylstannyl-3-vinyl-3-trimethylsilyloxy-1-octene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-vinyl-13-trans prostene |
| EXAMPLE | VINYL IODIDE | | CYCLOPENTENONE | PRODUCT PROSTAGLANDIN OF THE 11-DEOXY PGI1 SERIES |
| 395 | 1-trans-iodo-3-triphenylmethoxy-1-nonene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-20-methyl-13-trans prostene |
| 396 | 1-trans-iodo-3-methyl-3-trimethylsilyloxy-1-nonene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-methyl-20-methyl-13-trans prostene |
| 397 | 1-trans-iodo-4,4-dimethyl-3-trimethylsilyloxy-1-nonene | | 2-[6-(2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-dimethyl-20-methyl-13-trans prostene |

| | | -continued | |
|---|---|---|---|
| 398 | | 1-trans-iodo-4,4-trimethylene-3-trimethylsilyloxy-1-nonene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-trimethylene-20-methyl-13-trans prostene |
| EXAMPLE | VINYL TIN | CYCLOPENTENONE | PRODUCT PROSTAGLANDIN OF THE 11-DEOXY PGI1 SERIES |
| 399 | | 1-trans-tri-n-butylstannyl-3-vinyl-3-trimethylsilyloxy-1-nonene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-vinyl-20-methyl-13-trans prostene |
| EXAMPLE | VINYL IODIDE | CYCLOPENTENONE | PRODUCT PROSTAGLANDIN OF THE 11-DEOXY PGI1 SERIES |
| 400 | | 1-trans-iodo-3-triphenylmethoxy-1-decene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-20-ethyl-13-trans prostene |
| 401 | | 1-trans-iodo-3-methyl-3-trimethylsilyloxy-1-decene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-methyl-20-ethyl-13-trans prostene |
| 402 | | 1-trans-iodo-4,4-dimethyl-3-trimethylsilyloxy-1-decene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-dimethyl-20-ethyl-13-trans prostene |
| 403 | | 1-trans-iodo-4,4-trimethylene-3-trimethylsilyloxy-1-decene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-16,16-trimethylene-20-ethyl-13-trans prostene |
| EXAMPLE | VINYL TIN | CYCLOPENTENONE | PRODUCT PROSTAGLANDIN OF THE 11-DEOXY PGI1 SERIES |
| 404 | | 1-trans-tri-n-butylstannyl-3-vinyl-3-trimethylsilyloxy-1-decene | 2-[6(-2-(trimethylsiloxymethyl)-1,3-dioxolan-2-yl)hex-2-cis-enyl]cyclopent-2-en-1-one | dl-15α-hydroxy-1-hydroxymethyl-1-oxo-6,9α-epoxy-15-vinyl-20-ethyl-13-trans prostene |
| EXAMPLE | VINYL IODIDE | CYCLOPENTENONE | PRODUCT PROSTAGLANDIN OF THE 11-DEOXY PGI1 SERIES |
| 405 | | 1-trans-iodo-3-triphenylmethoxy-1-heptene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-20-nor-2-homo-13-trans prostene |
| 406 | | 1-trans-iodo-3-methyl-3-trimethylsilyloxy-1-heptene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-15-methyl-20-nor-2-homo-13-trans prostene |
| 407 | | 1-trans-iodo-4,4-dimethyl-3-trimethylsilyloxy-1-heptene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16,16-dimethyl-20-nor-2-homo-13-trans prostene |
| 408 | | 1-trans-iodo-5,5-dimethyl-3-triphenylmethoxy-1-octene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-17,17-dimethyl-2-homo-13-trans prostene |
| 409 | | 1-trans-iodo-4-methyl-3-triphenylmethoxy-1-octene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16-methyl-2-homo-13-trans prostene |
| 410 | | 1-trans-iodo-4,4-trimethylene-3-trimethylsilyloxy-1-heptene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16,16-trimethylene-20-nor-2-homo-13-trans prostene |
| EXAMPLE | VINYL TIN | CYCLOPENTENONE | PRODUCT PROSTAGLANDIN OF THE 11-DEOXY PGI1 SERIES |
| 411 | | 1-trans-tri-n-butylstannyl-3-vinyl-3-trimethylsilyloxy-1-heptene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-15-vinyl-20-nor-2-homo-13-trans prostene |

| EXAMPLE | VINYL IODIDE | CYCLOPENTENONE | PRODUCT PROSTAGLANDIN OF THE 11-DEOXY PGI1 SERIES |
|---|---|---|---|
| 412 | 1-trans-tri-n-butylstannyl-4-phenoxy-3-trimethylsilyloxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-phenoxy-2-homo-17-20-tetranor-13-trans prostene |
| 413 | 1-trans-tri-n-butylstannyl-4-(p-fluorophenoxy)-3-triethylsilyloxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-(p-fluorophenoxy)-2-homo-17-20-tetranor-13-trans prostene |
| 414 | 1-trans-tri-n-butylstannyl-4-(m-chlorophenoxy)-3-triethylsilyloxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-(m-chlorophenoxy)-2-homo-17-20-tetranor-13-trans prostene |
| 415 | 1-trans-tri-n-butylstannyl-4-(m-trifluoromethylphenoxy)-3-triethylsilyloxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-(m-trifluoromethylphenoxy)-2-homo-17-20-tetranor-13-trans prostene |
| EXAMPLE | VINYL IODIDE | CYCLOPENTENONE | PRODUCT PROSTAGLANDIN OF THE 11-DEOXY PGI1 SERIES |
| 416 | 1-trans-iodo-5-phenyl-3-triethylsilyloxy-1-pentene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-17-phenyl-2-homo-18-20-trinor-13-trans prostene |
| 417 | 1-trans-iodo-4,4-dimethyl-5-phenyl-3-triethylsilyloxy-1-pentene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16,16-dimethyl-17-phenyl-2-homo-18-20-trinor-13-trans prostene |
| 418 | 1-trans-iodo-4-cyclopentyl-3-triphenylmethoxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-cyclopentyl-2-homo-17-20-tetranor-13-trans prostene |
| 419 | 1-trans-iodo-4-cyclohexyl-3-triphenylmethoxy-1-butene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16-cyclohexyl-2-homo-17-20-tetranor-13-trans prostene |
| 420 | 1-trans-iodo-3-triphenylmethoxy-1-octene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-2-homo-13-trans prostene |
| 421 | 1-trans-iodo-3-methyl-3-trimethylsilyloxy-1-octene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-15-methyl-2-homo-13-trans prostene |
| 422 | 1-trans-iodo-4,4-dimethyl-3-trimethylsilyloxy-1-octene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16,16-dimethyl-2-homo-13-trans prostene |
| 423 | 1-trans-iodo-4,4-trimethylene-3-trimethylsilyloxy-1-octene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16,16-trimethylene-2-homo-13-trans prostene |
| EXAMPLE | VINYL TIN | CYCLOPENTENONE | PRODUCT PROSTAGLANDIN OF THE 11-DEOXY PGI1 SERIES |
| 424 | 1-trans-tri-n-butylstannyl-3-vinyl-3-trimethylsilyloxy-1-octene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-15-vinyl-2-homo-13-trans prostene |
| EXAMPLE | VINYL IODIDE | CYCLOPENTENONE | PRODUCT PROSTAGLANDIN OF THE 11-DEOXY PGI1 SERIES |
| 425 | 1-trans-iodo-3-triphenylmethoxy-1-nonene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-20-methyl-2-homo-13-trans prostene |
| 426 | 1-trans-iodo-3-methyl-3-trimethylsilyloxy-1-nonene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-15-methyl-20-methyl-2-homo-13-trans prostene |
| 427 | 1-trans-iodo-4,4-dimethyl-3-trimethylsilyloxy-1-nonene | 2-[7-(-2-(trimethylsiloxymethyl)-1,3-dioxolan-2-yl)hept-2-cis-enyl] cyclopent-2-en-1-one | dl-15α-hydroxy-1-hydroxymethyl-1-oxo-6,9α-epoxy-16,16-dimethyl-20-methyl-2-homo-13-trans prostene |

| | | -continued | |
|---|---|---|---|
| 428 | 1-trans-iodo-4,4-trimethylene-3-trimethylsilyloxy-1-nonene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16,16-trimethylene-20-methyl-2-homo-13-trans prostene |

| EXAMPLE | VINYL TIN | CYCLOPENTENONE | PRODUCT PROSTAGLANDIN OF THE 11-DEOXY PGII SERIES |
|---|---|---|---|
| 429 | 1-trans-tri-n-butylstannyl-3-vinyl-3-trimethylsilyloxy-1-nonene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-15-vinyl-20-methyl-2-homo-13-trans prostene |

| EXAMPLE | VINYL IODIDE | CYCLOPENTENONE | PRODUCT PROSTAGLANDIN OF THE 11-DEOXY PGII SERIES |
|---|---|---|---|
| 430 | 1-trans-iodo-4-triphenylmethoxy-1-nonene | 2-[7(-2-(trimethylsiloxymethyl)-1,3-dioxolan-2-yl)hept-2-cis-enyl]cyclopent-2-en-1-one | dl-16-hydroxy-1-hydroxymethyl-1-oxo-6,9α-epoxy-20-methyl-2-homo-13-trans prostene |
| 431 | 1-trans-iodo-3-triphenylmethoxy-1-decene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-20-ethyl-2-homo-13-trans prostene |
| 432 | 1-trans-iodo-3-methyl-3-trimethylsilyloxy-1-decene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-15-methyl-20-ethyl-2-homo-13-trans prostene |
| 433 | 1-trans-iodo-4,4-dimethyl-3-trimethylsilyloxy-1-decene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16,16-dimethyl-20-ethyl-2-homo-13-trans prostene |
| 434 | 1-trans-iodo-4,4-trimethylene-3-trimethylsilyloxy-1-decene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-16,16-trimethylene-20-ethyl-2-homo-13-trans prostene |

| EXAMPLE | VINYL TIN | CYCLOPENTENONE | PRODUCT PROSTAGLANDIN OF THE 11-DEOXY PGII SERIES |
|---|---|---|---|
| 435 | 1-trans-tri-n-butylstannyl-3-vinyl-3-trimethylsilyloxy-1-decene | 2-[7(-2-(trimethylsiloxymethyl)-1,3-dioxolan-2-yl)hept-2-cis-enyl]cyclopent-2-en-1-one | dl-15α-hydroxy-1-hydroxymethyl-1-oxo-6,9α-epoxy-15-vinyl-20-ethyl-2-homo-13-trans prostene |

EXAMPLE 438 nat.
11α,15α-Dihydroxy-5(R)-iodo-6R,9α-epoxy-13-trans-prostenoic acid methyl ester To a stirred mixture of 600 mg. of 1-PGF$_2$ methyl ester of 20 ml. of ether and 20 ml. of saturated aqueous sodium bicarbonate, cooled in an ice-water bath, is added very slowly during 2 hours, a solution of 490 mg. of iodine in 20 ml. of ether. The mixture is stirred vigorously at room temperature overnight, then diluted with ether, washed with 5% sodium thio-sulfate solution, water, brine and evaporated to an oil. This oil is purified by dry column chromatography (340 g. of silica gel, 1⅝"×42" column), eluting with 70% ethyl acetate, 1% acetic acid in hexane. This product fractions are washed with pure ethyl acetate and concentrated in the presence of toluene giving the desired product.

EXAMPLE 439 nat.
11α,15α-Dihydroxy-6,9α-epoxy-6S-13-trans-prostenoic acid methyl ester and the corresponding 6R-isomer A mixture of 150 mg. of nat. 11α,15α-dihydroxy-5(R)-iodo-6R,9α-epoxy-13-trans-prostenoic acid methyl ester in 0.1 ml. of toluene containing 0.2% ether, one mg. of azobisisobutyrnitrile and 0.12 ml. of tributylstannane is heated and stirred at 60°–70° C. for 2 hours. The mixture is concentrated to a pale yellow oil which is purified through a dry column (1"×38") of 100 g. of silica gel, eluting with 80% ethyl acetate and 1% acetic acid in hexane. The product fractions are washed with ethyl acetate and evaporated to dryness in the presence of toluene giving 50 mg. of 6β-isomer and 10 mg. of 6α-isomer.

EXAMPLE 440 nat.
11α,15α-Dihydroxy-6,9α-epoxy-6(S)-13-trans-prostenoic acid

A mixture comprising 148 mg. of nat. 11α,15α-dihydroxy-5(R)-iodo-6R,9α-epoxy-13-trans-prostenoic acid methyl ester in 0.1 ml. of toluene and 0.2 ml. of ether, 0.12 ml. of tributylstannane and one mg. of azobisisobutyrnitrile is heated and stirred at 60°–70° C. for 2 hours, cooled and concentrated in vacuo to dryness. The residue is passed through a 2.5 g. pad of silica gel (Silicar CC-77) and washed with 35 ml. of hexane, 50 ml. of ether, then 30 ml. of ethyl acetate. The ether and ethyl acetate extracts are combined and saponified by dissolving in 1.2 ml. of methanol and 1.5 ml. of 1 N sodium hydroxide and stirring at room temperature for 1.5 hours. This mixture is concentrated, diluted with ether and acidified with 4 N hydrochloric acid. The ehter layer is washed with water and brine and concentrated to dryness giving the desired product as 90 mg. of an oil which solidifies on standing.

We claim:

1. A compound of the formula:

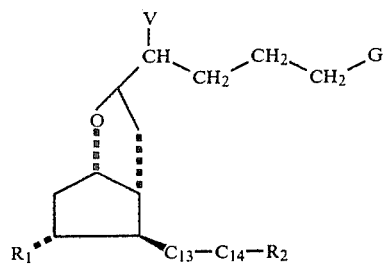

wherein V is selected from the group hydrogen, bromo, chloro and iodo, G is selected from the group

—C(O)CH$_2$OH, C(O)CH$_2$OR,

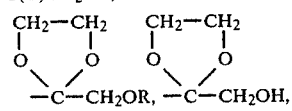

and —C(O)—CH$_2$SR$_{16}$, wherein R is C$_1$ to C$_6$ alkyl, or optionally substituted phenyl, the substituents selected from the group C$_1$ to C$_4$ alkyl, C$_1$ to C$_4$ alkoxy, halo and trifluoromethyl, R$_1$ is hydrogen or hydroxy and R$_{16}$ is C$_1$ to C$_6$ alkyl; C$_{13}$ to C$_{14}$ is selected from the group —CH=CH—(trans) and —CH$_2$CH$_2$—, R$_2$ is selected from the group

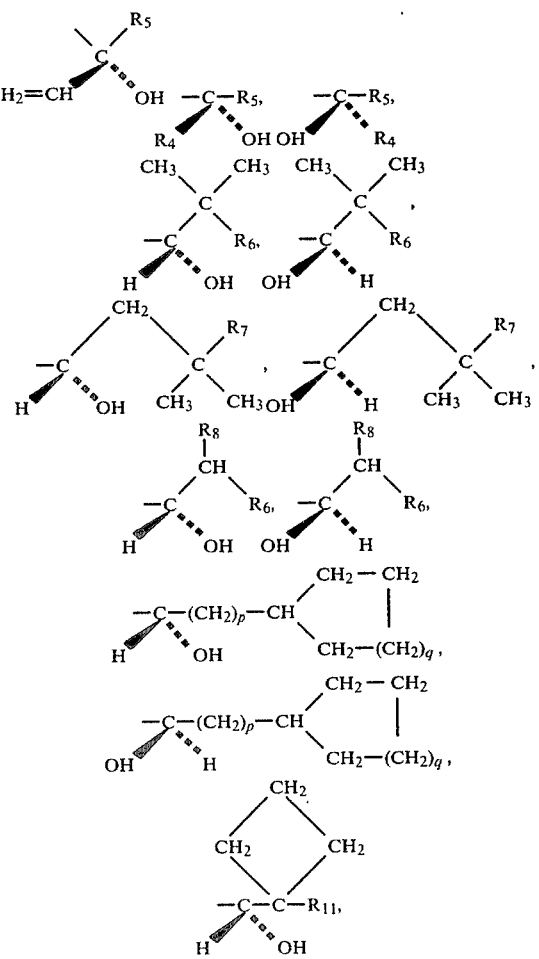

-continued

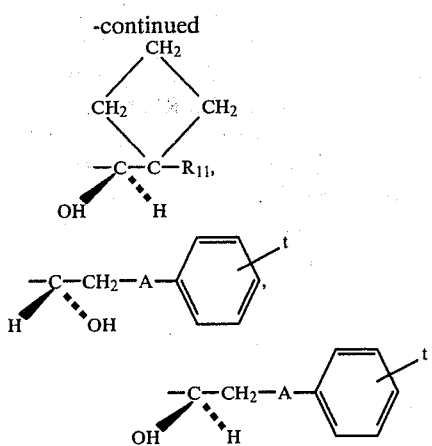

A is a divalent radical selected from —CH$_2$— and —O—, R$_4$ is hydrogen or methyl; R$_5$ is selected from the group consisting of C$_4$-C$_7$ alkyl; R$_6$ is selected from the group consisting of C$_3$-C$_6$ alkyl; R$_7$ is selected from the group consisting of C$_2$-C$_4$ alkyl; R$_8$ is selected from the group consisting of C$_1$-C$_2$ alkyl; R$_{11}$ is selected from the group consisting of C$_3$-C$_7$ alkyl; p is an integer from 0 to 3; q is 1 or 2 and t is selected from the group hydrogen, chloro, fluoro, dichloro, trifluoro-methyl and methoxy, the racemic mixtures thereof; the mirror images thereof, and the pharmaceutically acceptable, non-toxic salts thereof.

2. The optically active compound of claim 1 wherein G is selected from the group —C(O)CH$_2$OH, —C(O)CH$_2$OR

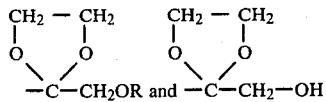

and V and R, are as previously defined and the racemic mixture thereof.

3. The optically active compound of claim 2 wherein V is hydrogen, or iodo and the racemic mixture thereof.

4. The optically active compounds of claim 3 wherein R$_2$ is selected from the group

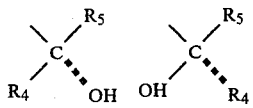

where R$_4$ and R$_5$ are previously defined and the racemix mixture thereof.

5. A racemic compound according to claim 4, dl-11a,15a-DIHYDROXY-1-HYDROXYMETHYL-1-OXO-6,9a-EPOXY-13-trans PROSTENE.

6. A optically active compound according to claim 4, nat-11a,15a-DIHYDROXY-1-HYDROXYMETHYL-1-OXO-6,9a-EPOXY-13-trans PROSTENE.

7. A racemic compound according to claim 4, dl-11a,15a-DIHYDROXY-1-HYDROXYMETHYL-1-OXO-6,9a-EPOXY-15-METHYL-13-trans PROSTENE.

8. A optically active compound according to claim 4, nat-11a,15a-DIHYDROXY-1-HYDROXYMETHYL-1-OXO-6,9a-EPOXY-15-METHYL-13-trans PROSTENE.

9. The optically active compound according to claim 3 wherein R$_5$ is selected from the group

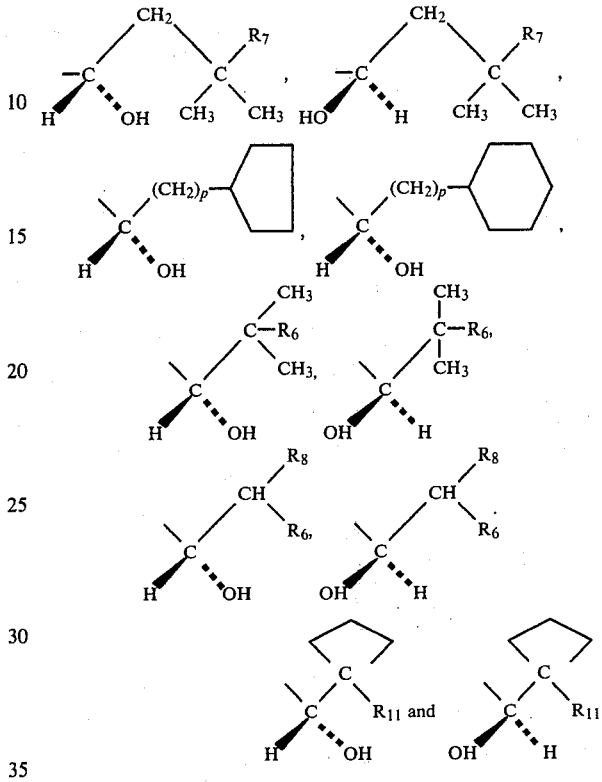

wherein R$_{11}$, R$_6$, R$_8$ and p are as previously defined.

10. A racemic compound according to claim 9, dl-11a,15a-DIHYDROXY-1-HYDROXYMETHYL-1-OXO-6,9a-EPOXY-16,16-DIMETHYL-13-trans PROSTENE.

11. A optically active compound according to claim 9, nat-11a,15a-DIHYDROXY-1-HYDROXYMETHYL-1-OXO-6,9a-EPOXY-16,16-DIMETHYL-13-trans PROSTENE.

12. A racemic compound according to claim 9, dl-11a,15a-DIHYDROXY-1-HYDROXYMETHYL-1-OXO-6,9a-EPOXY-17,17-DIMETHYL-13-trans PROSTENE.

13. A optically active compound according to claim 9, nat-11a,15a-DIHYDROXY-1-HYDROXYMETHYL-1-OXO-6,9a-EPOXY-17,17-DIMETHYL-13-trans PROSTENE.

14. A racemic compound according to claim 9, dl-11a,15a-DIHYDROXY-1-HYDROXYMETHYL-1-OXO-6,9a-EPOXY-16-METHYL-13-trans PROSTENE.

15. A optically active compound according to claim 9, nat-11a,15a-DIHYDROXY-1-HYDROXYMETHYL-1-OXO-6,9a-EPOXY-16-METHYL-13-trans PROSTENE.

16. A racemic compound according to claim 9, dl-11a,15a-DIHYDROXY-1-HYDROXYMETHYL-1-OXO-6,9a-EPOXY-16,16-TRIMETHYLENE-13-trans PROSTENE.

17. A optically active compound according to claim 9, nat-11a,15a-DIHYDROXY-1-HYDROXYMETHYL-1-OXO-6,9a-EPOXY-16,16-TRIMETHYLENE-13-trans PROSTENE.

18. A racemic compound according to claim 9, dl-11a,15a-DIHYDROXY-1-HYDROXYMETHYL-1-OXO-6,9a-EPOXY-16,CYCLOPENTYL-17,18,19,20-tetranor-13-trans PROSTENE.

19. An optically active compound according to claim 9, nat-11a,15a-DIHYDROXY-1-HYDROXYMETHYL-1-OXO-6,9a-EPOXY-16-CYCLOPENTYL-17,18,19,20-tetranor-13-trans PROSTENE.

20. A racemic compound according to claim 9, dl-11a,15-DIHYDROXY-1-HYDROXYMETHYL-1-OXO-6,9a-EPOXY-16-CYCLOHEXYL-17,18,19,20-tetranor-13-trans PROSTENE.

21. A optically active compound according to claim 9, nat-11a,15a-DIHYDROXY-1-HYDROXYMETHYL-1-OXO-6,9a-EPOXY-16-CYCLOHEXYL-17,18,19,20-tetranor-13-trans PROSTENE.

22. The optically active compound of claim 3 where $R_2$ is selected from the group

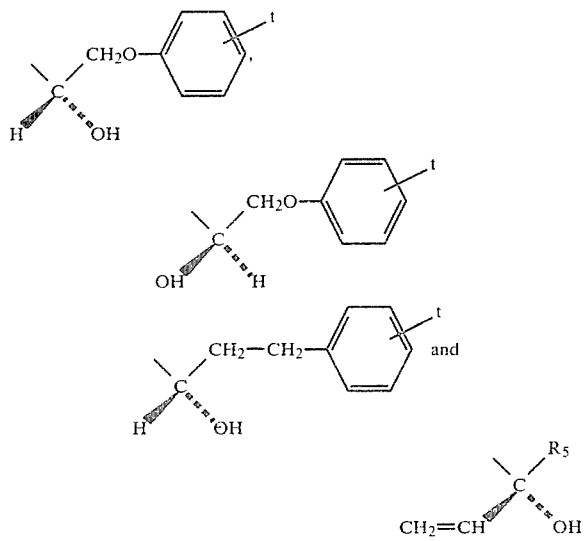

wherein $R_5$ and t are as previously defined and the racemic mixture thereof.

23. A racemic compound according to claim 22, dl-11a,15a-DIHYDROXY-1-HYDROXYMETHYL-1-OXO-6,9a-EPOXY-15-vinyl-13-trans PROSTENE.

24. A optically active compound according to claim 22, nat-11a,15a-DIHYDROXY-1-HYDROXYMETHYL-1-OXO-6,9a-EPOXY-15-VINYL-13-trans PROSTENE.

25. A racemic compound according to claim 22, dl-11a,15a-DIHYDROXY-1-HYDROXYMETHYL-1-OXO-6,9a-EPOXY-16-PHENOXY-17,18,19,20-tetranor-13-trans PROSTENE.

26. A optically active compound according to claim 22, nat-11a,15a-DIHYDROXY-1-HYDROXYMETHYL-1-OXO-6,9a-EPOXY-16-PHENOXY-17,18,19,20-tetranor-13-trans PROSTENE.

27. A racemic compound according to claim 22, dl-11a,15a-DIHYDROXY-1-HYDROXYMETHYL-1-OXO-6,9a-EPOXY-16-(p-FLUOROPHENOXY)-17,18,19,20-tetranor-13-trans PROSTENE.

28. A optically active compound according to claim 22, nat-11a,15a-DIHYDROXY-1-HYDROXYMETHYL-1-OXO-6,9a-EPOXY-16-(p-FLUOROPHENOXY)-17,18,19,20-tetranor-13-trans PROSTENE.

29. A racemic compound according to claim 22, dl-11a,15a-DIHYDROXY-1-HYDROXYMETHYL-1-OXO-6,9a-EPOXY-16-(m-CHLOROPHENOXY)-17,18,19,20-tetranor-13-trans PROSTENE.

30. A optically active compound according to claim 22, nat-11a,15a-DIHYDROXY-1-HYDROXYMETHYL-1-OXO-6,9a-EPOXY-16-(m-CHLOROPHENOXY)-17,18,19,20-tetranor-13-trans PROSTENE.

31. A racemic compound according to claim 22, dl-11a,15a-DIHYDROXY-1-HYDROXYMETHYL-1-OXO-6,9a-EPOXY-16-(m-TRIFLUOROMETHYLPHENOXY)-17,18,19,20-tetranor-13-trans PROSTENE.

32. A optically active compound according to claim 22, nat-11a,15a-DIHYDROXY-1-HYDROXYMETHYL-1-OXO-6,9a-EPOXY-16-(m-TRIFLUOROMETHYLPHENOXY)-17,18,19,20-tetranor-13-trans PROSTENE.

33. A racemic compound according to claim 22, dl-11a,15a-DIHYDROXY-1-HYDROXYMETHYL-1-OXO-6,9a-EPOXY-17-PHENYL-18,20-trinor-13-trans PROSTENE.

34. A optically active compound according to claim 22, nat-11a,15a-DIHYDROXY-1-HYDROXYMETHYL-1-OXO-6,9a-EPOXY-17-PHENYL-18,19,20-trinor-13-trans PROSTENE.

35. A racemic compound according to claim 22, dl-11a,15a-DIHYDROXY-1-HYDROXYMETHYL-1-OXO-6,9a-EPOXY-16,16-DIMETHYL-17-PHENYL-18,19,20-trinor-13-trans PROSTENE.

36. A optically active compound according to claim 22, nat-11a,15a-DIHYDROXY-1-HYDROXYMETHYL-1-OXO-6,9a-EPOXY-16,16-DIMETHYL-17-PHENYL-18,20-trinor-13-trans PROSTENE.

37. The racemic compound according to claim 2 wherein V is hydrogen, chloro or iodo and $R_1$ is hydrogen.

38. A racemic compound according to claim 37, dl-15a-HYDROXY-1-HYDROXYMETHYL-1-OXO-6,9a-EPOXY-13-trans PROSTENE.

39. A racemic compound according to claim 37, dl-15a-HYDROXY-1-HYDROXYMETHYL-1-OXO-6,9a-EPOXY-15-METHYL-13-trans PROSTENE.

40. A racemic compound according to claim 37, dl-15a-HYDROXY-1-HYDROXYMETHYL-1-OXO-6,9a-EPOXY-16,16-DIMETHYL-13-trans PROSTENE.

41. A racemic compound according to claim 37, dl-15a-HYDROXY-1-HYDROXYMETHYL-1-OXO-6,9a-EPOXY-17,17-DIMETHYL-13-trans PROSTENE.

42. A racemic compound according to claim 37, dl-15a-HYDROXYMETHYL-1-OXO-6,9a-EPOXY-16-METHYL-13-trans PROSTENE.

43. A racemic compound according to claim 3, dl-15a-HYDROXY-1-HYDROXYMETHYL-1-OXO-6,9a-EPOXY-16,16-TRIMETHYLENE-13-trans PROSTENE.

44. A racemic compound according to claim 37, dl-15a-HYDROXY-1-HYDROXYMETHYL-1-OXO-6,9a-EPOXY-15-VINYL-13-trans PROSTENE.

45. A racemic compound according to claim 37, dl-15a-HYDROXY-1-HYDROXYMETHYL-1-OXO-6,9a-EPOXY-16-PHENOXY-17,18,19,20-tetranor-13-trans PROSTENE 46. A racemic compound according to claim 37, dl-15a-HYDROXY-1-HYDROXYMETHYL-1-OXO-6,9a-EPOXY-16-(p-FLUOROPHENOXY)-17,18,19,20-tetranor-13-trans PROSTENE.

47. A racemic compound according to claim 37, dl-15a-HYDROXY-1-HYDROXYMETHYL-1-OXO-6,9a-EPOXY-16-(m-CHLOROPHENOXY)-17,18,19,20-tetranor-13-trans PROSTENE.

48. A racemic compound according to claim 37, dl-15a-HYDROXY-1-HYDROXYMETHYL-1-OXO-6,9a-EPOXY-16-(m-TRIFLUOROMETHYL-PHENOXY)-17,18,19,20-tetranor-13-trans PROSTENE.

49. A racemic compound according to claim 37, dl-15a-HYDROXY-1-HYDROXYMETHYL-1-OXO-6,9a-EPOXY-17-PHENYL-18,19,20-trinor-13-trans PROSTENE.

50. A racemic compound according to claim 37, dl-15a-HYDROXY-1-HYDROXYMETHYL-1-OXO-6,9a-EPOXY-16,16-DIMETHYL-17-PHENYL-18,19,20-trinor-13-trans PROSTENE.

51. A racemic compound according to claim 37, dl-15a-HYDROXY-1-HYDROXYMETHYL-1-OXO-6,9a-EPOXY-16-CYCLOPENTYL-17,18,19,20-tetranor-13-trans PROSTENE.

52. A racemic compound according to claim 37, dl-15a-HYDROXY-1-HYDROXYMETHYL-1-OXO-6,9a-EPOXY-16-CYCLOHEXYL-17,18,19,20-tetranor-13-trans PROSTENE.

53. A method for causing bronchodilation in mammals which comprises administering an effective amount of an optically active compound of the formula

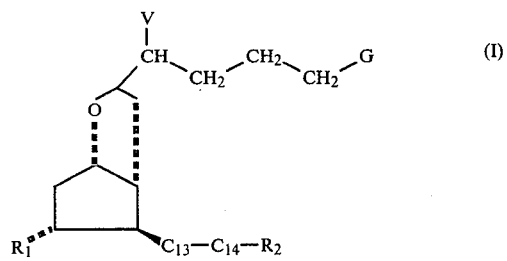

wherein V is selected from the group hydrogen, bromo, chloro and iodo, G is selected from the group

—C(O)CH$_2$OH, C(O)CH$_2$OR, —C—CH$_2$OR,

-continued
—C—CH$_2$OH, and —C(O)—CH$_2$SR$_{16}$, wherein R is C$_1$ to C$_6$ alkyl, or optionally substituted phenyl, the substituents selected from the group C$_1$ to C$_4$ alkyl, C$_1$ to C$_4$ alkoxy, halo and trifluoromethyl, R$_1$ is hydrogen or hydroxy and R$_{16}$ is C$_1$ to C$_6$ alkyl; C$_{13}$ to C$_{14}$ is selected from the group —CH=CH—(trans) and —CH$_2$CH$_2$—, R$_2$ is selected from the group

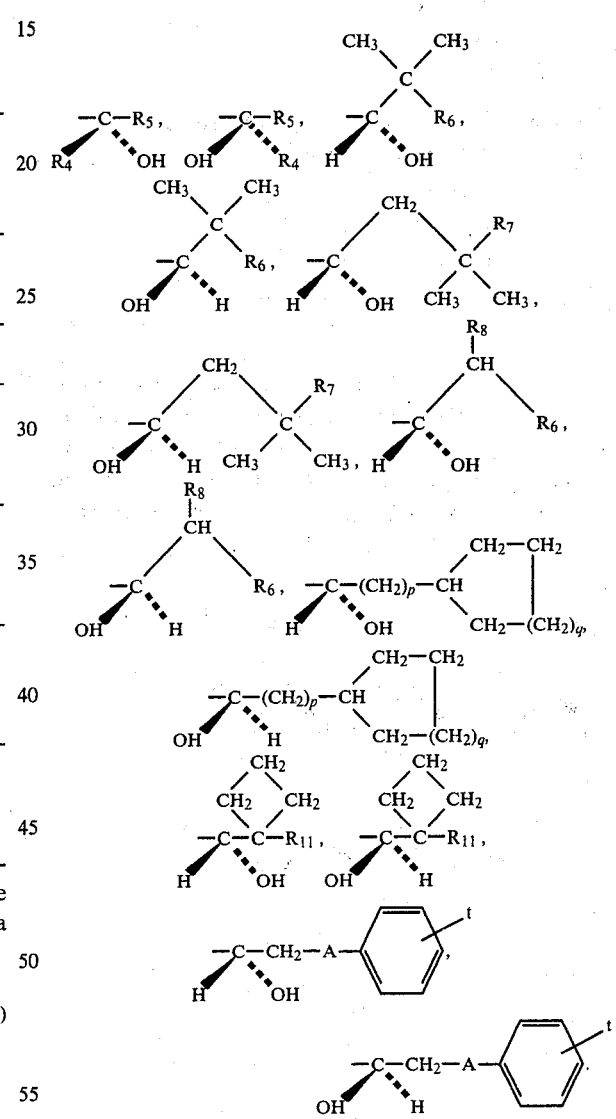

A is a divalent radical selected from —CH$_2$— and —O—, R$_4$ is hydrogen or methyl; R$_5$ is selected from the group consisting of C$_4$–C$_7$ alkyl; R$_6$ is selected from the group consisting of C$_3$–C$_6$ alkyl; R$_7$ is selected from the group consisting of C$_2$–C$_4$ alkyl; R$_8$ is selected from the group consisting of C$_1$–C$_2$ alkyl; R$_{11}$ is selected from the group consisting of C$_3$–C$_7$ alkyl; p is an integer from 0 to 3; q is 1 or 2 and t is selected from the group hydrogen, chloro, fluoro, dichloro, trifluoro-methyl and methoxy, the racemic mixtures thereof; the mirror images thereof, and the pharmaceutically acceptable, non-toxic salts thereof.

54. A composition effective in causing bronchodilation in mammals which comprises a bronchodilatory effective amount of compounds of the formula:

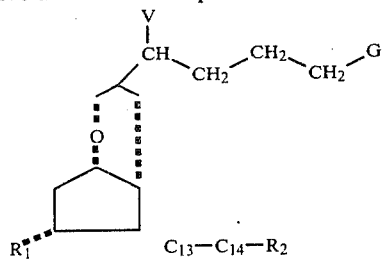

wherein V is selected from the group hydrogen, bromo, chloro and iodo, G is selected from the group

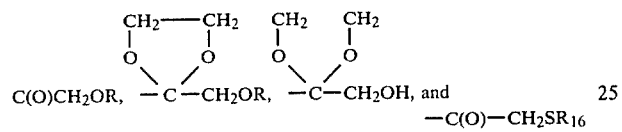

wherein R is $C_1$ to $C_6$ alkyl, or optionally substituted phenyl, the substituents selected from the group $C_1$ to $C_4$ alkyl, $C_1$ to $C_4$ alkoxy, halo and trifluoromethyl, $R_1$ is hydrogen or hydroxy and $R_{16}$ is $C_1$ to $C_6$ alkyl; $C_{13}$ to $C_{14}$ is selected from the group —CH=CH—(trans) and —CH$_2$CH$_2$—, $R_2$ is selected from the group

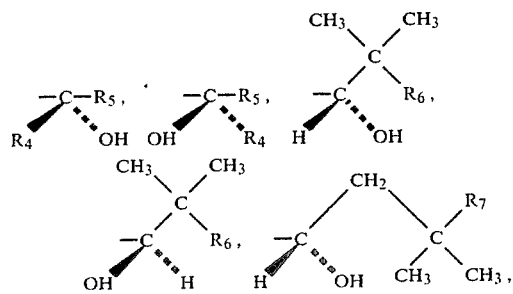

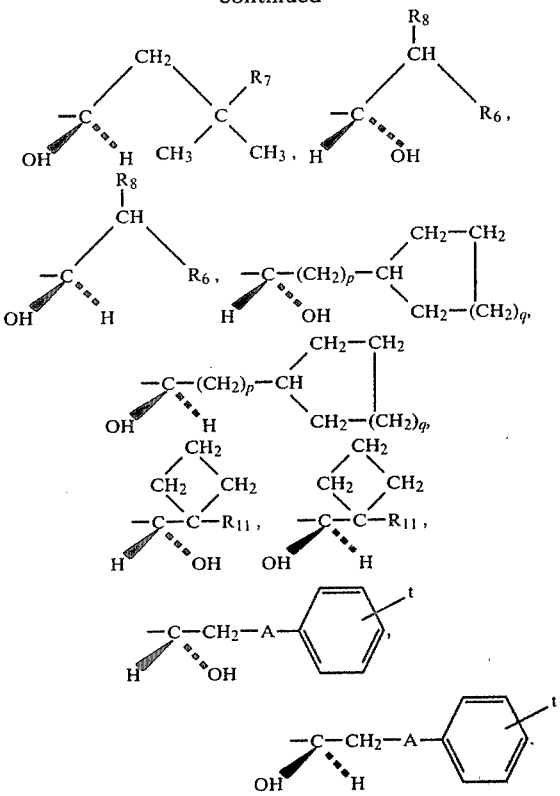

A is a divalent radical selected from —CH$_2$— and —O—, $R_4$ is hydrogen or methyl; $R_5$ is selected from the group consisting of $C_4$–$C_7$ alkyl; $R_6$ is selected from the group consisting of $C_3$–$C_6$ alkyl; $R_7$ is selected from the group consisting of $C_2$–$C_4$ alkyl; $R_8$ is selected from the group consisting of $C_1$–$C_2$ alkyl; $R_{11}$ is selected from the group consisting of $C_3$–$C_7$ alkyl; p is an integer from 0 to 3; q is 1 or 2 and t is selected from the group hydrogen, chloro, fluoro, dichloro, trifluoro, methyl and methoxy, the racemic mixtures thereof; the mirror images thereof, and the pharmaceutically acceptable, non-toxic salts thereof in a pharmacologically suitable carrier.

* * * * *